US007364904B2

(12) United States Patent
Boyd et al.

(10) Patent No.: US 7,364,904 B2
(45) **Date of Patent: *Apr. 29, 2008**

(54) **METHODS AND COMPOSITION FOR DIAGNOSING AND TREATING *PSEUDOXANTHOMA ELASTICUM* AND RELATED CONDITIONS**

(75) Inventors: Charles D. Boyd, Honolulu, HI (US); Katalin Csiszar, Honolulu, HI (US); Olivier LeSaux, Honolulu, HI (US); Zsolt Urban, Honolulu, HI (US); Sharon Terry, Potomac, MD (US)

(73) Assignees: PXE International, Inc., Washington, DC (US); The University of Hawaii, Honolulu, HI (US)

( * ) Notice: Subject to any disclaimer, the term of this patent is extended or adjusted under 35 U.S.C. 154(b) by 522 days.

This patent is subject to a terminal disclaimer.

(21) Appl. No.: 10/764,328

(22) Filed: Jan. 23, 2004

(65) Prior Publication Data

US 2004/0166521 A1 Aug. 26, 2004

Related U.S. Application Data

(63) Continuation of application No. 09/792,616, filed on Feb. 23, 2001, now Pat. No. 6,780,587.

(60) Provisional application No. 60/184,269, filed on Feb. 23, 2000.

(51) Int. Cl.
*C12Q 1/68* (2006.01)

(52) U.S. Cl. .......................................................... 436/6

(58) Field of Classification Search ..................... 435/6
See application file for complete search history.

(56) References Cited

FOREIGN PATENT DOCUMENTS

WO WO 98/37764 9/1998

OTHER PUBLICATIONS

Le Saux et al. (Genomics (1999) vol. 62, pp. 1-10).*

Phendner et al. J. Med. Genet. Online, Jul. 6, 2007, pp. 1-16 [Epub prior to print].*

Hu et al. Investigative Ophthalmology and Visual Science, vol. 44, No. 5, pp. 1824-1829, May 2003.*

Cotton, (1993), "Current methods of mutation detection," *Mutation Research*, 285:125-144.

Le Saux et al., (1999), "*Pseudoxanthoma elasticum* Maps to an 820-kb Region of the p13.1 Region of Chromosome 16," *Genomics*, 62:1-10.

Le Saux et al., (2000), "Mutations in a gene encoding an ABC transporter cause *Pseudoxanthoma elasticum,*" *Nature Genetics*, 25:2:223-227, abstract only.

Ringpfeil et al., (2000), "*Pseudoxanthoma elasticum*: Mutations in the *MRP6* gene encoding a transmembrane ATP-binding cassette (ABC) transporter," *Proc. Natl. Acad. Sci.*, 97:11:6001-6006.

International Search Report for International Patent Application Serial No. PCT/US01/05741, dated Jul. 18, 2002, 3 pages.

Bacchelli et al., (1999), "Identification of Heterozygote Carriers in Families with a Recessive Form of *Pseudoxanthoma elasticum* (PXE)," *Modern Pathology*, 12(12):1112-1123.

Bergen et al. (2000), "Mutations in ABCC6 cause *Pseudoxanthoma elasticum,*" *Nature Genetics*, 25(2):228-231.

Cai et al., (2000), "A 500-kb region on chromosome 16p13.1 contains the *Pseudoxanthoma elasticum* locus: high-resolution mapping and genomic structure," *Journal of Molecular Medicine*, 78(1):36-46.

Germain et al., (2000), "Homozygosity for the R1268Q Mutation in MRP6, the *Pseudoxanthoma elasticum* Gene, Is Not Disease-Causing," *Biochemical and Biophysical Research Communications*, 274(2):297-301.

Germain et al., (2000), "Identification of Two Polymorphisms (c189G>C; c190T>C) in Exon 2 of the Human MRP6 Gene (ABCC6) by Screening of *Pseudoxanthoma elasticum* Patients: Possible Sequence Correction?" *Human Mutation*, Mutation and Polymorphism Report #174, Online (3 pages).

Hopper et al., (2001), "Analysis of the structure and expression pattern of MRP7 (ABCC10), a new member of the MRP subfamily," *Cancer Letters*, 162(2):181-191.

Kool et al., (1999), "Expression of Human MRP6, a Homologue of the Multidrug Resistance Protein Gene MRP1, in Tissues and Cancer Cells," *Cancer Research*, 59:175-182.

Le Saux et al., (2000), "Mutations in gene encoding an ABC Transporter cause *Pseudoxanthoma elasticum,*" *Nature Genetics*, 25: 223-227.

Le Saux et al., (2001), "A Spectrum of ABCC6 Mutations Is Responsible for *Pseudoxanthoma elasticum,*" *American Journal of Human Genetics*, 69: 749-764.

Mao et al., (1999), "ATPase activity of purified and reconstituted multidrug resistance protein MRP1 from drug-selected H69AR cells," *Biochimica et Biophysica Acta*, 1461:69-82.

Perdu et al., (2000), "Identification of Novel Polymorphisms in the pM5 and MRP1 (ABCC1) Genes at Locus 16p13.1 and Exclusion of Both Genes as Responsible for *Pseudoxanthoma elasticum,*" *Human Mutation*, Mutation in Brief #388, Online (5 pages).

Quaglino et al., (2000), "Abnormal phenotype of in vitro dermal fibroblasts from patients with *Pseudoxanthoma elasticum* (PXE)," *Biochimica et Biophysica Acta*, 1501:51-62.

Renie et al., (1984), "*Pseudoxanthoma elasticum*: High Calcium Intake in Early Life Correlates With Severity," *American Journal of Medical Genetics*, 19:235-244.

(Continued)

*Primary Examiner*—Gary Benzion
*Assistant Examiner*—Cynthia B Wilder
(74) *Attorney, Agent, or Firm*—Kirkpatrick & Lockhart Preston Gates Ellis LLP

(57) ABSTRACT

Methods and compositions are provided for diagnosing and treating *Pseudoxanthoma elasticum* (PXE) patients and PXE carriers. Methods and compositions are based on the discovery that PXE mutations are located in the MRP6 (ABCC6) gene.

7 Claims, 6 Drawing Sheets

OTHER PUBLICATIONS

Ringpfeil et al., (2000), "Mutations in the MRP6 Gene Cause *Pseudoxanthoma elasticum," The Journal of Investigative Dermatology*, 115(2):332, Abstract HB1.

Sapadin et al., (1998), "Periumbilical *Pseudoxanthoma elasticum* associated with chronic renal failure and angioid streaks—apparent regression with hemodialysis," *Journal of the American Academy of Dermatology*, 39(2):338-344.

Struk et al., (2000), "Mutations of the gene encoding the transmembrane transporter protein ABC-C6 cause *Pseudoxanthoma elasticum," Journal of Molecular Medicine*, 78(5):282-286.

Tybulewicz et al., (1991), "Neonatal Lethality and Lymphopenia in Mice with a Homozygous Disruption of the c-*abl* Proto-Oncogene," *Cell*, 65:1153-1163.

* cited by examiner

MAAPAEPCAGQGVWNQTEPEPAATSLLSLCFLRTAGVWVPPMYLWVLGPIYLLFIHHHGR
GYLWMSPLFKAKMVLGFALIVLCTSSVAVALWKIQQGTPEAPEFLIHPTVWLTTMSFAVF
LIHTERKKGVQSSGVLFGYWLLCFVLPATNAAQQASGAGFQSDPVRHLSTYLCLSLVVAQ
FVLSCLADQPPFFPEDPQQSNPCPETGAAFPSKATFWWVSGLVWRGYRRPLRPKDLWSLG
RENSSEELVSRLEKEWMRNRSAARRHNKAIAFKRKGGSGMKAPETEPFLRQEGSQWRPLL
KAIWQVFHSTFLLGTLSLIISDVFRFTVPKLLSLFLEFIGDPKPPAWKGYLLAVLMFLSA
CLQTLFEQQNMYRLKVLQMRLRSAITGLVYRKVLALSSGSRKASAVGDVVNLVSVDVQRL
TESVLYLNGLWLPLVWIVVCFVYLWQLLGPSALTAIAVFLSLLPLNFFISKKRNHHQEEQ
MRQKDSRARLTSSILRNSKTIKFHGWEGAFLDRVLGIRGQELGALRTSGLLFSVSLVSFQ
VSTFLVALVVFAVHTLVAENAMNAEKAFVTLTVLNILNKAQAFLPFSIHSLVQARVSFDR
LVTFLCLEEVDPGVVDSSSSGSAAGKDCITIHSATFAWSQESPPCLHRINLTVPQGCLLA
VVGPVGAGKSSLLSALLGELSKVEGFVSIEGAVAYVPQEAWVQNTSVVENVCFGQELDPP
WLERVLEACALQPDVDSFPEGIHTSIGEQGMNLSGGQKQRLSLARAVYRKAAVYLLDDPL
AALDAHVGQHVFNQVIGPGGLLQGTTRILVTHALHILPQADWIIVLANGAIAEMGSYQEL
LQRKGALVCLLDQARQPGDRGEGETEPGTSTKDPRGTSAGRRPELRRERSIKSVPEKDRT
TSEAQTEVPLDDPDRAGWPAGKDSIQYGRVKATVHLAYLRAVGTPLCLYALFLFLCQQVA
SFCRGYWLSLWADDPAVGGQQTQAALRGGIFGLLGCLQAIGLFASMAAVLLGGARASRLL
FQRLLWDVVRSPISFFERTPIGHLLNRFSKETDTVDVDIPDKLRSLLMYAFGLLEVSLVV
AVATPLATVAILPLFLLYAGFQSLYVVSSCQLRRLESASYSSVCSHMAETFQGSTVVRAF
RTQAPFVAQNNARVDESQRISFPRLVADRWLAANVELLGNGLVFAAATCAVLSKAHLSAG
LVGFSVSAALQVTQTLQWVVRNWTDLENSIVSVERMQDYAWTPKEAPWRLPTCAAQPPWP
QGGQIEFRDFGLRYRPELPLAVQGVSFKIHAGEKVGIVGRTGAGKSSLASGLLRLQEAAE
GGIWIDGVPIAHVGLHTLRSRISIIPQDPILFPGSLRMNLDLLQEHSDEAIWAALETVQL
KALVASLPGQLQYKCADRGEDLSVGQKQLLCLARALLRKTQILILDEATAAVDPGTELQM
QAMLGSWFAQCTVLLIAHRLRSVMDCARVLVMDKGQVAESGSPAQLLAQKGLFYRLAQES
GLV

Figure 3

METHODS AND COMPOSITION FOR DIAGNOSING AND TREATING *PSEUDOXANTHOMA ELASTICUM* AND RELATED CONDITIONS

RELATED APPLICATIONS

This application is a continuation of U.S. Ser. No. 09/792,616, filed Feb. 23, 2001, now U.S. Pat. No. 6,780,587 and claims priority to, and the benefit of U.S. Ser. No. 60/184,269, filed Feb. 23, 2000, the entire disclosures of which are incorporated by reference herein in their entireties.

GOVERNMENT SUPPORT

Work described herein was supported in part by Federal Grant No. EY 13019. The U.S. Government has certain rights in the invention.

FIELD OF THE INVENTION

The present invention relates generally to the field of physiological dysfunctions associated with *Pseudoxanthoma elasticum.* More particularly, the invention is concerned with the identification of a gene associated with *Pseudoxanthoma elasticum,* as well as mutations in the gene that cause the disease. The present invention also relates to methods for detecting and diagnosing *Pseudoxanthoma elasticum,* to methods for identifying carriers of mutant and normal alleles of the gene associated with *Pseudoxanthoma elasticum,* to methods for screening compounds to identify potential therapeutics for *Pseudoxanthoma elasticum,* to treatment methods for *Pseudoxanthoma elasticum,* and to useful cell lines and animal models of the disease.

BACKGROUND OF THE INVENTION

*Pseudoxanthoma elasticum* (PXE) is a heritable disorder characterized by mineralization of elastic fibers in skin, arteries and the retina, that result in dermal lesions with associated laxity and loss of elasticity, arterial insufficiency, cardiovascular disease and retinal hemorrhages leading to macular degeneration.

The skin manifestations are among the most common characteristics of PXE, but the ocular and cardiovascular symptoms are responsible for the morbidity of the disease. Characteristic skin lesions are generally an early sign of PXE and were first described by a French dermatologist in 1896. Skin lesions are usually detected during childhood or adolescence and progress slowly and often unpredictably. Therefore, the initial diagnosis of PXE is sometimes made by a dermatologist. The skin lesions consist of yellowish papules and plaques and laxity with loss of elasticity, and result from an accumulation of abnormal mineralized elastic fibers in the mid-dermis. Lesions are typically seen on the face, neck, axilla, antecubital fossa, popliteal fossa, groin and periumbilical areas. A PXE diagnosis can be confirmed by a skin biopsy that shows calcification of fragmented elastic fibers in the mid- and lower dermis.

Another characteristic of PXE is the presence of ocular lesions due to the accumulation of abnormal elastic fibers in the Bruch's membrane, resulting in angioid streaks. Doyne was the first to describe these ocular streaks in 1889, and Knapp introduced the term "angioid streaks" for their resemblance to blood vessels. The combination of PXE and ocular manifestations was initially referred to as the Gronblad-Strandberg syndrome, after the names of two ophthalmologists who independently related the occurrence of angioid streaks to PXE in 1929. The majority of PXE patients (approximately 85%) develop ocular manifestations during their second decade of life. Bilateral angioid streaks are normally seen as linear gray or dark red lines with irregular serrated edges lying beneath normal retinal blood vessels and represent breaks in the Bruch's membrane. The Bruch's membrane is not in a true sense a "membrane" but rather a heterogeneous elastin-rich layer separating the chorioid from the retina. The elastic laminae of the Bruch's membrane is located between two layers of collagen (type I, III and IV) which lie in direct contact with the basement membranes of the retinal pigmented epithelium (RPE) and the capillaries in the choriocapillary layer of the chorioid As a consequence of angioid streaks, a PXE patient progressively develops a chorioidal neovascularization with a subsequent hemorrhagic detachment of the fovea and later scarring. Optic nerve drusen may also be associated with angioid streaks and results in visual field deficits and even advanced visual impairment.

Common cardiovascular complications of PXE are due to the presence of abnormal calcified elastic fibers in the internal elastic lamina of medium-sized arteries. The broad spectrum of phenotypes includes premature atherosclerotic changes, intimal fibroplasia causing angina or intermittent claudication or both, early myocardial infarction and hypertension Fibrous thickening of the endocardium and atrioventricular valves can also result in restrictive cardiomyopathy. Approximately 10% of PXE patients also develop gastrointestinal bleedings and central nervous system complications (such as stroke and dementia) as a consequence of systemic arterial wall mineralization. In addition, renovascular hypertension and atrial septal aneurysm can be seen in PXE patients.

Strikingly, lung abnormalities are not a significant phenotypic feature of PXE, even though pulmonary tissues are rich in elastic fibers. Mineralization of pulmonary elastic fibers has only been noted in a few patients.

PXE is usually found as a sporadic disorder but examples of both autosomal recessive and autosomal dominant forms of PXE have been reported. Partial manifestations of the PXE phenotype have also been described in presumed carriers in PXE families. Recent reports have linked both the dominant and recessive forms of PXE to a 5 cM domain on chromosome 16P13.1 However, the mechanisms underlying the physiological defects characteristic of PXE are not understood.

Therefore, there is a need in the art for methods and compositions for diagnosing and treating PXE and PXE associated phenotypes.

SUMMARY OF THE INVENTION

The invention provides methods and compositions for diagnosing and treating PXE and PXE associated physiological dysfunctions. According to the invention, mutations associated with PXE are located in the (MRP6) ABCC6 gene. Therefore, methods for detecting the presence of a mutation associated with PXE involve interrogating the (MRP6) ABCC6 gene, or a portion thereof, for the presence of one or more mutations that are associated with PXE. Accordingly, one aspect of the invention provides methods for identifying individuals that have one or two mutant alleles at the PXE locus. PXE is most often an autosomal recessive disease. Therefore, an individual with two mutant (MRP6) ABCC6 alleles associated with PXE will develop symptoms characteristic of the disease. In contrast, an individual with one mutant (MRP6) ABCC6 allele associated with PXE is a carrier of the disease and does not develop full-blown PXE. However, according to one embodiment of the invention, a PXE carrier may develop mild forms of the characteristic manifestations. Accordingly, a PXE carrier status can be indicative of a predisposition to PXE related symptoms such as eye, skin, or cardiovascular problems. In a preferred embodiment of the invention, genetic counseling is provided to an individual identified as having a mutation associated with PXE in one or both alleles of the PXE ((MRP6) ABCC6) locus.

In another aspect, the invention provides compositions for detecting the presence of a mutation associated with PXE at the (MRP6) ABCC6 locus. In a preferred embodiment, an oligonucleotide that hybridizes to the (MRP6) ABCC6 locus is used in a diagnostic assay. In a more preferred embodiment, the oligonucleotide includes a sequence complementary to a mutation that is associated with PXE. Alternatively, an antibody-based diagnostic assay is used to detect the presence of a mutation associated with PXE at the (MRP6) ABCC6 locus.

Other aspects of the invention include therapeutic uses of the (MRP6) ABCC6 gene or protein, drug screening, the identification of (MRP6) ABCC6 homologues in other organisms (including mammalian organisms), cellular and animal models of PXE, the identification of (MRP6) ABCC6 functional domains related to the PXE phenotype, the identification of regulators of (MRP6) ABCC6 expression (mutations in these regulators can also result in PXE related symptoms), the identification of genes/proteins that interact with (MRP6) ABCC6 (alterations in these interacting molecules can also cause PXE related symptoms).

Thus, in one series of embodiments the invention provides methods for screening for the presence of a PXE mutation by interrogating an MRP6 nucleic acid obtained from a patient for the presence of a PXE mutation. The screen is positive is the presence of a PXE associated mutation is detected. A PXE associated mutation is a mutation that causes the PXE phenotype in an individual that is homozygous for the mutation. PXE associated mutations also causes the PXE phenotype in an individual that is a compound heterozygote with two different mutant alleles at the MRP6 locus, wherein each allele is a PXE associated allele. Nucleic acid is isolated from a patient biological sample, and the biological sample is preferably blood, saliva, amniotic fluid, or tissue such as a biopsy tissue. According to the invention, an MRP6 nucleic acid is a nucleic acid obtained from the MRP6 locus. An MRP6 nucleic acid can be mRNA, genomic DNA or cDNA from the MRP6 locus, or a PCR product of any of the above. According to the invention, the MRP6 locus includes the MRP6 exons, introns, and associated promoter and regulatory sequences in the genome surrounding the MRP6 exons.

In one series of embodiments, a PXE associated mutation is detected in MRP6 using a nucleic acid based detection assay. Preferred nucleic acid based detection assays include hybridization assays, primer extension assays, SSCP, DGGE, RFLP, LCR, DIHPLC, and enzymatic cleavage assays. In another series of embodiments, a PXE associated mutation is detected in a protein based detection assay. Preferred protein based detection assays include ELISA and a Western blot assays. In one embodiment of the invention, mutation detection assays are provided to screen the MRP6 locus or a portion thereof to determine whether a mutation is present. The lack of MRP6 expression or the expression of a physically aberrant form of MRP6 may be sufficient to determine that an individual has a PXE associated mutation at the MRP6 locus. Alternatively, the determination that a mutation is present in the MRP6 locus may not be sufficient to determine the PXE status of an individual in the absence of information concerning the specific identity of the mutation. If such a mutation is present, it may be identified according to methods of the invention, for example by sequencing the region of the MRP6 locus that contains the mutation. Once a mutation is identified in a patient sample, the PXE status of the patient can be determined according to methods of the invention. In an alternative embodiment of the invention, specific mutation detection assays are provided to detect a known PXE associated MRP6 mutation in a patient sample.

In another series of embodiments, the invention provides oligonucleotide probes or primers and antibodies for use in mutation detection assays or screens according to the invention.

In another series of embodiments, the invention provides methods for screening candidate drug compounds to identify therapeutic compounds for treating PXE patients (individuals that have PXE due to the presence of two recessive PXE associated MRP6 alleles, or one apparently dominant PXE allele) or PXE carriers (individuals with one normal MRP6 allele and one allele with a PXE associated mutation).

In another series of embodiments, the invention provides methods for treating PXE patients or carriers using a normal MNP6 nucleic acid or protein to restore normal MRP6 function to the individual or to specific cells or tissues or the individual.

In another series of embodiments, the invention provides methods for creating transgenic or knockout cell lines and animals in order to provide a model system for PXE.

In another series of embodiments, the invention provides methods for identifying compounds such as other intracellular proteins that interact with MRP6 thereby to identify additional therapeutic targets for PXE treatment.

Accordingly, the invention provides methods and compositions for unambiguously determining the PXE status of an individual. The invention provides methods for detecting deletions, substitutions, insertions, and rearrangements in the MRP6 locus that are associated with PXE. In preferred embodiments, the invention provides methods for identifying mutations known to be associated with PXE. Preferred mutations include mutations that affect one or more of the bases in codons 1114, 1138, 1141, 1298, 1302, 1303, 1314, 1321 and other codons identified herein as being important for normal MRP6 function. Alternatively, the invention provides methods to identify mutations that result in non-conservative substitutions in the MRP6 locus. In a further embodiment, the invention provides assays to detect PXE associated mutations at intron/exon splice sites of the MRP6 gene. The invention also provides methods to detect mutations that affect one or more regulatory elements of the MRP6 gene, including the promoter, the polyA site and other transcriptional or translational control sequences.

Methods of the invention are also useful to screen a population in order to identify individuals with one or more PXE associated MRP6 alleles. According to the invention, these individuals are provided with appropriate genetic counseling in view of their PXE status.

BRIEF DESCRIPTION OF THE DRAWINGS

FIG. 3 shows conserved amino acids in the human MRP6 protein.

DETAILED DESCRIPTION OF THE INVENTION

The invention provides methods and compositions for diagnosing and treating PXE and PXE related symptoms. Methods and compositions of the invention rely in part on the discovery that mutations associated with PXE map to the (MRP6) ABCC6 gene locus on chromosome 16. Accordingly, the invention provides useful PXE related diagnostic and therapeutic methods and compositions by exploiting wild-type and mutant (MRP6) ABCC6 genes and proteins.

Figure 1:
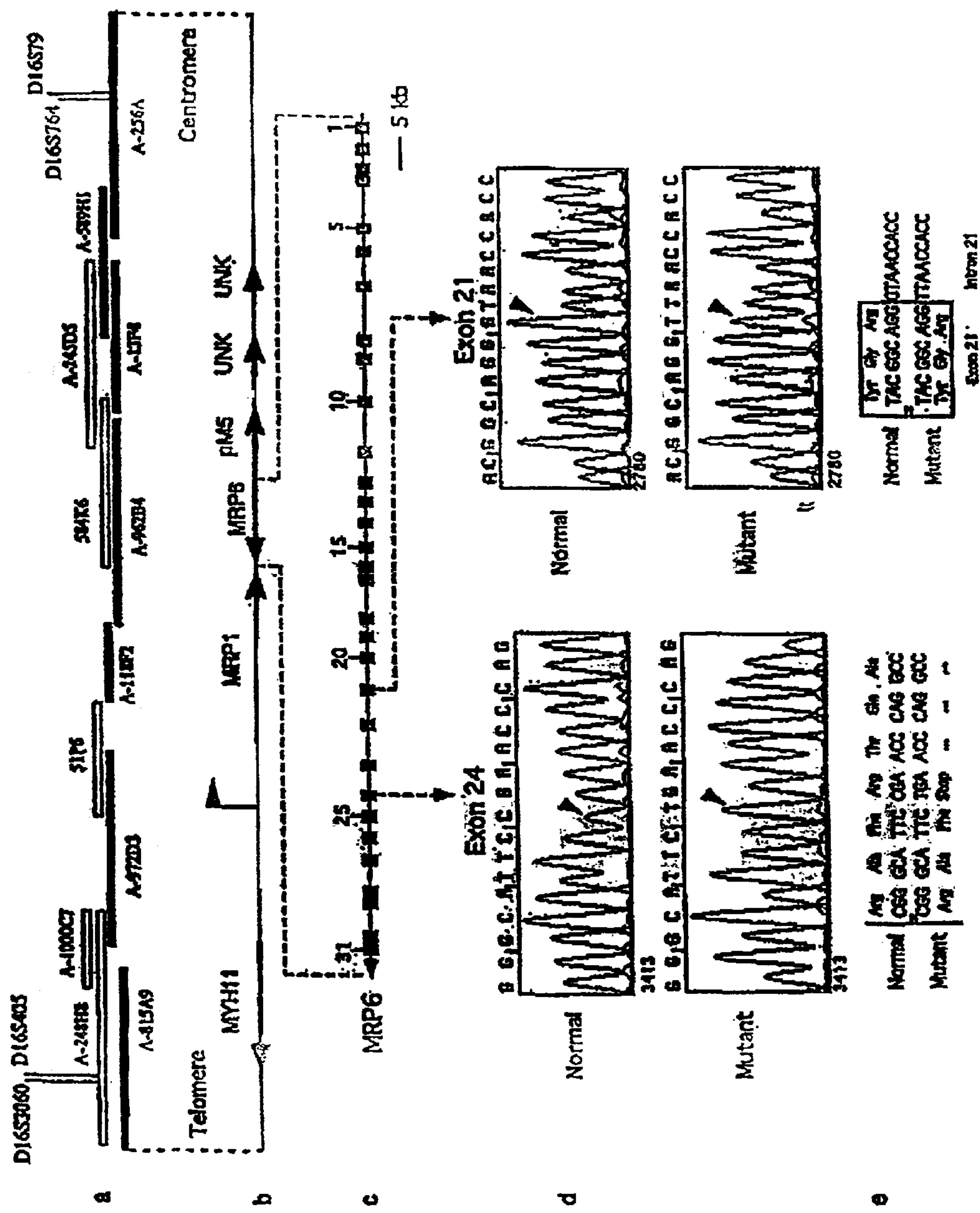
FIG. 1 shows the structure of the MRP6 gene and the surrounding genomic regions. Two (MRP6) ABCC6 mutations that cause PXE are indicated.

I. PXE Associated Mutations in the (MRP6) ABCC6 Gene a) Mapping of PXE Associated Mutations to the (MRP6) ABCC6 Genetic Locus Although the first case of PXE was reported by Darier in 1896, most PXE cases have been reported since the 1970s. In most reports, PXE is inherited as an autosomal recessive (AR) phenotype or appears as a sporadic phenotype. However, kindreds showing apparent autosomal dominant (AD) inheritance have also been reported. Using DNA from patients and unaffected family members from 21 unrelated PXE families, the PXE phenotype was linked to the short arm of chromosome 16. A very significant linkage with an 8 cM region was demonstrated with a maximum lod score of 8.07. A subsequent haplotype analysis and recombination mapping reduced the locus from 8 cM to 820 kb where six candidate genes were identified. The locus was later reduced to less than 600 kb and one candidate gene was excluded. All 109 exons of the five remaining candidate genes were screened by a combination of single-strand conformation polymorphism (SSCP), heteroduplex analysis (HA) or direct sequencing using genomic DNA from a cohort of 17 unrelated PXE patients and three unrelated normal individuals. The first six mutations, clearly associated with the PXE phenotype, were found in the (MRP6) ABCC6 gene (also known as the ABCC-6 gene). This analysis is described in further detail in Example 2. According to the invention, the MRP6 gene has 31 exons as shown in FIG. 1. A 107.7 kb genomic sequence that includes the MRP6 locus is shown in SEQ ID NO: 1. The sequence of SEQ ID NO: 1 shows the complementary strand of the MRP6 gene. The intron/exon boundaries are as follows (on the complementary strand of SEQ ID NO: 1): Ex1: 102783-102748; Ex2: 101180-100998; Ex3: 99296-99171; Ex4: 99031-98903; Ex5: 93798-93676; Ex6: 91594-91533; Ex7: 88207-88076; Ex8: 82954-82757; Ex9: 81524-81347; Ex10: 77528-77367; Ex11: 72268-72176; Ex12: 69718-69515; Ex13: 68325-68182; Ex14: 66562-66475; Ex15: 64385-64310; Ex16: 62282-62156; Ex17: 61940-61764; Ex18: 58324-58457; Ex19: 56985-56811; Ex20: 55345-55270; Ex21: 52757-52637; Ex22: 49588-49381; Ex23: 45578-45268; Ex24: 42837-42638; Ex25: 41209-41083; Ex26: 39226-39125; Ex27: 37453-37307; Ex28: 34674-34516; Ex29: 34437-34271; Ex30: 30412-30218; Ex31: 29881-29773. The mRNA coding sequence for human MRP6 is shown in SEQ ID NO: 2, and the encoded protein sequence is shown in SEQ ID NO: 3.

b) Identifying PXE Associated Mutations in the (MRP6) ABCC6 Locus

According to methods of the invention, additional PXE associated mutations were identified in the (MRP6) ABCC6 locus using a combination of single strand conformation polymorphism (SSCP), heteroduplex analysis (HA) and direct sequencing. Single nucleotide mutations in the (MRP6) ABCC6 gene were identified in several cohorts of individuals originating from the United States, South Africa and several European countries (Belgium, Germany, Holland, Italy and United Kingdom). To confirm the causative or polymorphic nature of new variants, a control panel of 300 alleles (150 normal individuals) was screened and the co-segregation of the identified variant and the PXE phenotype was verified. It is noteworthy that two single-allele mutations (R1141X, R1339C) were found in control panels of normal individuals indicating that heterozygote mutant (MRP6) ABCC6 alleles can be found in the normal population. However, the missense mutation (R1339C) was identified in the genetically distinct Afrikaners of South Africa. The frequency of heterozygote carriers deduced only from the appearance of these heterozygote mutations is 1.3 percent and is consistent with the commonly accepted figures of 0.6 to 2.5%. Indeed, while most mutations appeared to be private, a few have been clearly identified as recurrent (R1141X, R518Q, 3775delT, 16.5 kb deletion between exon 22 and 29. Most of the mutations (63%) were missense substitutions, 17% were nonsense mutations (5), 13% were frameshift mutations (4 deletions or an insertions of a single nucleotide) and 7% were likely to affect splicing (2).

Twenty-seven of the mutations (90%) affected the C-terminal half of the (MRP6) ABCC6 protein and particularly the various domains of the C-terminal ATP-binding site, which are encoded by exons 28 to 30, where 12 (40%) mutations were clustered. Remarkably, 10 mutations (33%) affected arginyl residues. Eight of these were missense substitutions, suggesting an essential structural or functional role for these arginyl residues in (MRP6) ABCC6.

Large deletions, which are not detected by SSCP or HA, can be identified by the loss of heterozygosity of informative polymorphic markers. Seven highly informative microsatellites present in a 300 kb region encompassing both ABCC1 and ABCC6, have been successfully used to detect large deletions involving parts or the entire ABCC6 gene. The loss of heterozygosity can also be efficiently implemented by using several highly polymorphic variants present in the ABCC6 gene. The latter approach was used to detect a partial deletion of the (MRP6) ABCC6 gene, in a compound heterozygous state, in a family with an apparent dominant form of PXE, as discussed in Example 3. A non-limiting list of known PXE associated mutations at the MRP6 locus are shown in Table 1.

TABLE 1

Known PXE associated mutations at the human MRP6 locus.

| Mutations | | Status | | |
|---|---|---|---|---|
| Effect | Nt change | Status | Origin | Exons |
| — | 938-939insT | ch, ht | A | 8 |
| R518Q | 1553G > A | ch, ht | a, u | 12 |
| F568S | 1703T > C | ht | U | 13 |
| L673P | 2018T > C | ch | A | 16 |

TABLE 1-continued

Known PXE associated mutations at the human MRP6 locus.

| Mutations | | Status | | |
|---|---|---|---|---|
| Effect | Nt change | Status | Origin | Exons |
| — | 1995delG | ch | G | 16 |
| — | 2322delC | ht | U | 18 |
| Y768X | 2204C > A | ch, ht | A | 18 |
| — | IVS21 + 1G > T | ch | U | Intron 21 |
| R1030X | 3088C > T | ht | A | 23 |
| R1114P | 3341G > C | hm | Uk | 24 |
| S1121W | 3362C > G | ch | G | 24 |
| R1138P | 3413G > C | ch | G | 24 |
| R1138Q | 3413G > A | ch | Uk | 24 |
| R1141X | 3421C > T | all | All | 24 |
| G1203D | 3608G > A | | | 25 |
| — | IVS26 − 1G > A | ch | B | Intron 26 |
| W1241C | 3723G > C | | | 26 |
| Q1237X | 3709C > T | ch | B | 26 |
| — | 3775delT | ht, hm | a, u, h | 27 |
| V1298F | 3892G > T | ht | U | 28 |
| T1301I | 3902C > T | ch | B | 28 |
| G1302R | 3904G > A | ht | U | 28 |
| A1303P | 3907G > C | ch | B | 28 |
| R1314W | 3940C > T | hm | U | 28 |
| R1314Q | 3941G > A | ht | G | 28 |
| G1321S | 3961G > A | ht | U | 28 |
| R1339C | 4015C > T | all | a, u | 28 |
| Q1347H | 4041G > C | ht | U | 28 |
| D1361N | 4081G > A | ch | G | 29 |
| R1398X | 4192C > T | ch | B | 29 |
| I1424T | 4271T > C | ht | U | 30 |

ch = compound heterozygote;
ht = heterozygote;
hm = homozygote;
ivs = intervening sequence According to methods of the invention, additional PXE associated mutations can be identified in the (MRP6) ABCC6 locus according to methods of the invention. For example, single strand conformation polymorphism (SSCP), heteroduplex analysis (HA), or direct sequence analysis can be used to identify additional mutations at the MRP6 locus. In one embodiment, the analysis is performed on genomic DNA. Alternatively, the analysis is performed on cDNA or on exon containing DNA amplification products such as exon containing PCR products. Deletion mutations are preferably detected using diagnostic PCR assays of genomic DNA and by Southern hybridization according to methods known in the art. In addition, fluorescent in situ hybridization (FISH) analysis of human chromosome preparations can be used to identify a deletion at the MRP6 locus or a deletion that encompasses all or part of the MRP6 locus. Specific mutations are preferably identified using DNA arrays including mutation specific oligonucleotide probes. Alternatively, mutation-specific antibodies can be used to detect mutations that alter an existing epitope or create a new specific epitope on the MRP6 protein. Preferably, specific antibodies are used on proteomic chips to detect protein altering mutations in the MRP6 gene. Mutations can also be detected using mass spectrometry, and mutation-specific mass spectrometer profiles can be generated for MRP6 nucleic acid or protein analysis according to methods known in the art.

c) PXE Associated Mutations at the (MRP6) ABCC6 Locus i) The (MRP6) ABCC6 Gene and Protein The (MRP6) ABCC6 gene, also known as the ABBC6 gene, encodes an ATP-binding cassette transporter (an ABC transporter) belonging to sub-family "C" which includes genes involved in drug-resistance such as MRP1 to 6 (ABCC1-6). (MRP6) ABCC6/ABCC6 encodes a 165 kDa protein that is located in the plasma membrane and has 17 membrane-spanning helices grouped into three transmembrane domains. MRP6 is highly homologous to MRP1 and may act as an efflux pump of amphipathic anion conjugates. Accordingly, in one aspect of the invention, MRP6 transports glutathione anion conjugates and also anionic drugs. Therefore, an individual that is a PXE carrier or a PXE homozygote or compound heterozygote may have reduced transport of anionic drugs and may be more receptive to chemotherapy using such drugs. The ABCC family of genes also includes the cystic fibrosis transmembrane conductance regulator gene (ABCC7 or CFTR) and the sulfonylurea receptor genes (ABCC8 and 9 or SUR).

Therefore, in contrast to genetic changes involved in other elastic fiber diseases such as Supravalvular Aortic Stenosis (SVAS), Marfan syndrome, and *Cutis laxa,* PXE associated mutations in the (MRP6) ABCC6 gene are not directly related to elastic fibers. The (MRP6) ABCC6/ABCC6 gene is expressed at relatively high levels in a limited range of tissues, notably in kidney and liver. However, low levels of expression are also observed in smooth muscle cells and macrophages. According to the invention, this tissue distribution suggests that (MRP6) ABCC6 has a function-related to cellular detoxification which may affect the calcification of elastic fibers in skin, arteries and the retina. Alternatively, calcification of elastic fibers in skin, arteries, and the retina may result from MRP6 functional deficiencies in those tissues.

Figure 2:
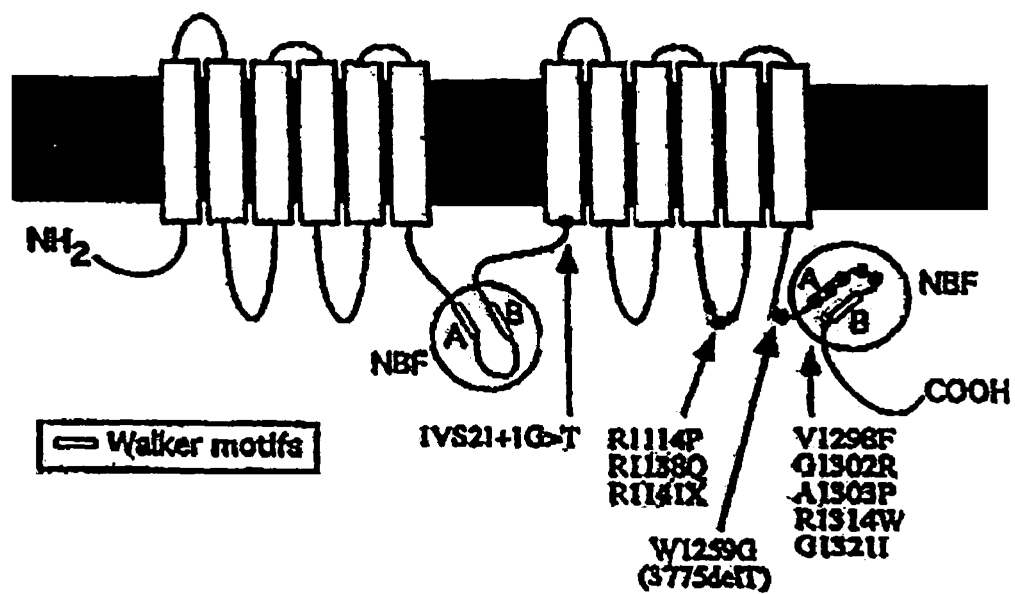
FIG. 2 shows the predicted topology of the MRP6 protein and the location of ten mutations causing PXE.

The predicted structure of the MRP6 protein is shown in FIG. 2. Transmembrane domains (unshaded rectangles), nucleotide-binding fold regions (NBF) and Walker motifs are indicated and were identified by amino acid sequence homology with similar transporters. Arrows indicate the positions of several PXE associated mutations. The large shaded rectangle represents the cell membrane.

According to the invention, the transmembrane domains of the MRP6 protein shown in FIG. 2 are hydrophobic stretches of amino acids identified via transmembrane domain predictions (SOSUI and DAS transmembrane prediction programs). Regions of MRP6/ABCC6 with a high degree of conservation when compared with similar proteins (ABC transporters) include the regions involved in the binding and hydrolysis of ATP also known as nucleotide binding folds (NBF). According to the invention, the MRP6 protein has two nucleotide-binding fold regions (NBF1 and NBF2) as shown in FIG. 2. These regions correspond to the following amino acid segments of the human MRP6 protein: NBF1 residues 656-679, 747-768, and 775-784 of SEQ ID NO: 3; and NBF2 residues 1292-1307, 1321-1327, and 1403-1433 of SEQ ID NO: 3.

According to one embodiment of the invention, conserved amino acids in the MRP6 protein are amino acids identified by comparing 1.2 ABC transporter proteins from Human, Rat, Mouse, *C. elegans,* Yeast (*S. cerevisiae*) and *A. thaliana.* Preferred conserved amino acids are shown in FIG. 3 (conserved amino acids are underlined). According to the invention, conserved domains are concentrated in the C-terminal portion of the protein, where over 90% of the PXE causing mutations have been identified.

ii) Mutations in the (MRP6) ABCC6 Gene

According to one aspect of the invention, PXE is caused by a mutation at the (MRP6) ABCC6 locus that results in reduced MRP6 protein function. PXE associated mutations include mutations that affect the level of MRP6 protein expression in addition to mutations that alter the functional properties of an expressed MRP6 protein PXE associated mutations at the (MRP6) ABCC6 locus include chain-terminating mutations. Such mutations are typically recessive and account for the autosomal recessive nature of the associated PXE phenotype. However, PXE associated mutations identified at the (MRP6) ABCC6 locus include chain terminating mutations at different positions in the (MRP6) ABCC6 gene, and several substitution, deletion and insertion mutations. According to the invention, the C-terminal half of the MRP6 protein is functionally important. Indeed, many of the PXE associated mutations were identified in exons 23-29. However, even a I to T substitution at position 1424 (out of 1503 amino acid residues) results in a PXE associated phenotype. Accordingly, a chain terminating or frameshift mutation in any one of exons 1-29, even up to position 1424 in exon 30, and maybe even beyond is expected to be associated with PXE. According to the invention, the PXE phenotype associated with different mutations in the (MRP6) ABCC6 gene varies in relation to the functional properties of the mutant (MRP6) ABCC6 protein product. Therefore, individuals with different PXE associated mutations can have PXE symptoms of differing severity. In addition, different individuals having the same PXE mutations, but in different genetic backgrounds, can also develop PXE symptoms of differing severity. Accordingly, different mutations at the PXE locus are expected to result in PXE phenotypes of differing severity. For example, in one embodiment of the invention, a mutation that results in the absence of MRP6 protein expression (for example a deletion of part or all of the gene, a chain terminating mutation, a mutation that prevents mRNA production, or a mutation that prevents translation of the mRNA) is expected to have a more severe PXE phenotype than a mutation that interferes with normal MRP6 protein function without destroying the function (for example an amino acid substitution that alters the structure and function of the protein without inactivating it. In particular, an individual that is a homozygote for a mutation that prevents MRP6 protein expression, or that is a compound heterozygote with two different mutations each of which prevents MRP6 protein expression, is expected to have a more severe phenotype than an individual that has a mutation with less severe effects on MRP6 protein function at one or both alleles of the MRP6 locus.

In a further embodiment of the invention, a heterozygote carrier of a PXE mutation can exhibit characteristic manifestations of PXE. In particular, a carrier of a recessive mutation can show partial skin, eye or cardiovascular symptoms. According to the invention, heterozygote carriers of different (MRP6) ABCC6 mutations can develop different subsets of PXE related symptoms and can have symptoms of varying severity. Indeed, there are numerous examples of dermal “elastic fibers changes” or cardiovascular abnormalities ranging from hypertension to myocardial infarction, in family members of severely affected individuals. According to the invention, cases of partial expression of PXE symptoms in heterozygote carriers are cases that had been assumed to be examples of dominant inheritance with for example 10 to 20% penetrance.

The various subtypes of a disorder or a dual mode of inheritance of a disease are frequently due either to mutations in different genes or different mutations in the same gene. Epidermolysis buflosa (EB) is an excellent example of a disorder characterized by several clinical types caused by distinct mutations in the same gene or mutations in different genes. EB is viewed as a group of heritable mechano-bullous skin diseases classified into three major categories of simplex, junctional and dystrophic forms. EB simplex is due to mutations in the genes encoding keratins 5 and 14, the junctional form is associated with mutations in the kalininl7aminin 5 genes; and the dystrophic disorder result from mutations in the type VII collagen gene (COL7Al). The dystrophic EB presents clinical sub-types: the Hallopeau-Siemens type is autosomal recessive and caused by nonsense mutations and glycine substitutions result in the autosomal dominant form.

In contrast to EB, no locus heterogeneity has been shown for PXE. According to the invention, most cases of PXE, if not all, are due to (MRP6) ABCC6 mutations. While the clinical heterogeneity in PXE patients may be caused by different types of (MRP6) ABCC6 mutations, the different PXE lesions (vascular, ocular, and dermal) observed for different autosomal recessive and seemingly dominant PXE mutations are clinically indistinguishable. Furthermore, identical PXE mutations can be either recessive or apparently dominant in unrelated pedigrees. Accordingly, different PXE mutations in different genetic backgrounds are associated with different severities of PXE symptoms. Furthermore, a PXE mutation can result in a partial PXE phenotype in a carrier individual (thereby accounting for observations of apparent dominant forms of PXE).

iii) Population Distributions of (MRP6) ABCC6 Mutations

According to the invention, different PXE associated (MRP6) ABCC6 mutations exist in the population, and new (MRP6) ABCC6 mutations arise sporadically. Based on current estimations of the prevalence of PXE in the United States (between 1:100,000 and 1:25,000), the frequency of appearance of heterozygote individuals with PXE mutations should be between 0.6 and 2.5 percent of the general population (1.5 to 6.0 million individuals). Given the risk of heterozygote individuals having children with PXE, an important aspect of the invention is to provide a genetic screen to identify heterozygote carriers of PXE mutations. According to the invention, a PXE carrier is an individual with one mutant allele of the (MRP6) ABCC6 gene, wherein the mutant allele is an allele that results in a PXE phenotype in an individual that is homozygous for that allele (or in an individual that is heterozygous with two different (MRP6) ABCC6 mutant alleles, each of which is associated with PXE).

According to a further embodiment of the invention, a significant factor in the complex phenotype of the PXE multi-organ disorder is partial expression of the full range of the PXE symptoms in heterozygote carriers in recessive pedigrees. For example, a single mutant-ABCC6 allele, for example R1141X, within heterozygote carriers can manifest a partial, mostly vascular-related phenotype. Indeed, cardiovascular abnormalities are frequently seen in obligate carriers but ocular and dermal lesions have also been diagnosed. The PXE phenotype, as observed in several heterozygous carriers, range from sub-clinical manifestations to visible lesions. The spectrum of these partial phenotypes overlaps with that of the less severely affected PXE patients. There is, therefore, a continuum in the PXE phenotype between heterozygous carriers and PXE patients, which make the clinical diagnosis of the less severe forms of PXE equivocal. According to the invention, cardiovascular symptoms associated with PXE mutations at the MRP6 gene include atherosclerosis, hypertension, stroke, gastrointestinal bleeding, intermittent claudication. Ocular symptoms include macular or retinal degeneration and skin related symptoms include premature aging and solar elastosis.

According to the invention, the identification of the PXE gene provides methods for an unambiguous molecular diagnosis of patients and the identification of heterozygous carriers in families with autosomal recessive PXE or apparent autosomal dominant PXE, and the identification of homozygous PXE individuals or PXE carriers in the general population.

According to the invention, different populations can contain different characteristic PXE associated MRP6 mutations or different frequencies of PXE associated MRP6 mutations due to factors such as founder effects. For example, a founder effect in the South African Afrikaner population is thought to have caused the observed higher frequency of PXE in Afrikaners. According to the invention, a higher frequency of PXE in a population correlates with a higher frequency of PXE associated MRP6 mutations.

Intra-familial variation of the phenotype is a well known characteristic of PXE. These variations may be due to genetic and/or environmental causes. A few environmental factors are thought to influence the PXE phenotype. Among these, calcium and Vitamin D have been reported to contribute to the severity of the phenotype in some cases. Life style, smoking, diet, sun-exposure and obesity are also likely to modulate the penetrance of the phenotype. Indeed, remarkably dissimilar PXE phenotypes have been observed recently in identical twins. According to the invention, non-genetic factors contributing to the development of PXE symptoms in heterozygote carriers can be identified. Studies involving large cohorts of twins for example, such as those used by the Queensland Institute of Medical Research of Australia are also useful to identify both genetic and environmental factors related to the development of the PXE phenotype.

II. Diagnostic Applications (MRP6) ABCC6 genes and gene products, including mutant genes and gene products, as well as probes, primers, and antibodies, are useful for identifying carriers of PXE associated mutations. According to the invention, PXE associated mutations can be identified in families with a PXE pedigree or in individuals not previously known to be at risk of carrying a PXE related mutation. PXE associated mutations can be routinely screened using probes to detect the presence of a mutant (MRP6) ABCC6 gene or protein by a variety of methods. In preferred embodiments of the invention, individuals are screened for the presence of a recurrent mutation that is known to be present at a relatively high frequency in the population. For example, a preferred method of the invention screens an individual from a population for the presence of an MRP6 mutation that accounts for about 30%, and preferably 50%, and more preferably over 50%, of known incidences of PXE in the population. An alternative method of the invention screens an individual for the presence of two or more, preferably about five, more preferably about ten, and even more preferably over ten PXE associated MRP6 mutations. In methods that include assays for a plurality of PXE associated MRP6 mutations, the plurality of mutations preferably account for about 30%, and more preferably 50%, and even more preferably over 50%, of known incidences of PXE in the population.

In one aspect of the invention, the identification of a specific mutation is not necessary. A diagnostic assay may be based on the detection of an MRP6 protein expression defect resulting from, for example, reduced levels of mRNA expression. Indeed, the analysis of steady state levels of (MRP6) ABCC6 mRNA in skin fibroblasts from a PXE patient carrying a homozygous R1141X mutation showed that MRP6 mRNA levels were lower than in skin fibroblasts from a normal individual. Accordingly, low levels MRP6 mNRA can result from a mutation within the coding sequence, such as a nonsense mutation that results in nonsense mediated decay. In addition, low mRNA levels can be caused by mutations either an intron or an exon that destabilizes the RNA, or by a mutation in a regulatory region (including a promoter region) that reduces transcription of the MRP6 gene. Furthermore, the presence of a truncated MRP6 mRNA can be used as a diagnostic indicator for the presence of a PXE associated mutation.

Alternatively, the presence of a mutation that affects the amount, size, or other physical properties of the MRP6 protein can be detected without knowing the identity of the mutation. For example a decreased level of MRP6 protein or a the presence of a truncation in the MRP6 protein can be used as a diagnostic indicator for the presence of a PXE associated mutation. In addition, the presence of a larger than expected MRP6 protein (that may result for example, from a gene fusion or from one or more frameshift mutations that produce a larger and possibly non-functional protein) can be used as a diagnostic indicator for the presence of a PXE associated mutation.

Accordingly the invention provides a method for screening for the presence of a PXE associated mutation at the MRP6 locus without specifically identifying the mutation. Such methods are useful to identify homozygotes, compound heterozygotes, or carriers.

According to the invention, the identification of the presence of any PXE associated mutation at the MRP6 locus can be used as a positive diagnosis of PXE in an individual with PXE symptoms or to diagnose a PXE patient who has not yet developed PXE symptoms but who is identified as a homozygote or a compound heterozygote for PXE associated MRP6 mutations. Alternatively, the detection of the presence of a PXE associated MRP6 mutation according to the invention provides a method for screening a population to identify individuals who are carriers of a PXE associated mutation.

In general, a PXE carrier is distinguished from a PXE homozygote by the presence of both a normal allele and a PXE mutant allele in the carrier and the presence of two PXE mutant alleles in the homozygote. According to the invention, a normal allele can contain a neutral polymorphism as disclosed herein.

a) Nucleic Acid Based Diagnostics

When a diagnostic assay is to be based upon nucleic acids from a sample, the assay may be based upon mRNA, cDNA or genomic DNA. If mRNA is used from a sample, there may be little or no expression of transcripts unless appropriate tissue sources are chosen or available. Preferred tissue sources are biopsies of full thickness skin or skin fibroblasts cultured from dermal biopsies. Whether mRNA, cDNA or genomic DNA is assayed, standard methods well known in the art may-be used to detect the presence of a particular sequence either in situ or in vitro (see, e.g., Sambrook et al., (1989) *Molecular Cloning: A Laboratory Manual,* 2nd ed., Cold Spring Harbor Press, Cold Spring Harbor, N.Y.). As a general matter, however, any tissue with nucleated cells may be examined.

Genomic DNA used for the diagnosis may be obtained from body cells, such as those present in the blood, tissue biopsy, surgical specimen, or autopsy material. The DNA may be isolated and used directly for detection of a specific sequence or may be amplified by the polymerase chain reaction (PCR) prior to analysis. Similarly, RNA or cDNA may also be used, with or without PCR amplification. To detect a specific nucleic acid sequence, direct nucleotide sequencing hybridization using specific oligonucleotides, restriction enzyme digest and mapping, PCR mapping, RNase protection, chemical mismatch cleavage, ligase-mediated detection, and various other methods may be employed. Oligonucleotides specific to particular sequences can be chemically synthesized and labeled radioactively or non-radioactively (e.g., biotin tags, ethidium bromide), and hybridized to individual samples immobilized on membranes or other solid-supports (e.g., by dot-blot or transfer from gels after electrophoresis), or in solution. The presence or absence of the target sequences may then be visualized using methods such as autoradiography, fluorometry, or colorimetry. These procedures can be automated using redundant, short oligonucleotides of known sequence fixed in high density to silicon chips, or in other oligonucleotide array formats.

Whether for hybridization, RNase protection, ligase-mediated detection, PCR amplification or any other standards methods described herein and well known in the art, a variety of subsequences of the MRP6 sequences disclosed or otherwise enabled herein will be useful as probes and/or primers. These sequences or subsequences will include both normal MRP6 sequences and PXE associated MRP6 mutant sequences. In general, useful oligonucleotide probes or primer sequences will include at least 8-9, more preferably 10-50, and most preferably 18-24 consecutive nucleotides from the MRP6 introns, exons or intron/exon boundaries. Depending upon the target sequence, the specificity required, and future technological developments, shorter sequences may also have utility. Therefore, any MRP6 derived sequence which is employed in a diagnostic assay may be regarded as an appropriate probe or primer. Particularly useful sequences include nucleotide positions from the MRP6 gene for which PXE, associated mutations are known, or sequences which flank these positions.

As discussed above, a variety of PXE causing mutations have now been identified at the human MRP6 gene locus. Detection of these and other PXE associated mutations is now enabled using isolated nucleic acid probes or primers derived from normal or mutant MRP6 genes. According to the invention, useful oligonucleotide probes or primers are derived from sequences encoding the C-terminal half of the MRP6 protein, the conserved NBF sequences, and conserved amino acid sequence shown in FIG. 3. Particularly useful oligonucleotides are derived from sequences known to have PXE associated mutations, such as the sequences including the mutations shown in Table 1. As disclosed above, a number of PXE associated MRP6 mutations have already identified, and it is expected that more will be identified according to the compositions and methods disclosed herein. Therefore, the present invention provides isolated nucleic acid probes and primers corresponding to normal and mutant sequences from any portion of the MRP6 gene, including exons, introns, and 5' and 3' UTRs, which may be shown to be associated with the development of PXE.

Merely as an example, and without limiting the invention, useful diagnostic probes and primers derived from the MRP6 DNA are disclosed in Example 5.

For in situ hybridization-based detection of a normal or mutant MRP6, a sample of tissue may be prepared by standard techniques and then contacted with one or more of the nucleic acids described herein, preferably one which is labeled to facilitate detection, and an assay for nucleic acid hybridization is conducted under stringent conditions which permit hybridization only between the probe and highly or perfectly complementary sequences. For the single nucleotide substitutions associated with PXE, high stringency hybridization conditions will be required to distinguish most mutant sequences from normal sequences. When the MRP6 genotypes of an individual's parents are known, probes may be chosen accordingly. Alternatively, probes to a variety of mutants may be employed sequentially or in combination. Because PXE carriers will be heterozygous, probes to normal sequences also may be employed and homozygous normal individuals may be distinguished from mutant heterozygotes by the amount of binding (e.g., by intensity of radioactive signal). In another variation, competitive binding assays may be employed in which both normal and mutant probes are used but only one is labeled.

In addition to oligonucleotide-based hybridization assays, methods of the invention include direct sequencing, loss of heterozygosity, SSCP, HA, and Conformation-Sensitive Gel Electrophoresis (CSGE) to detect a PXE associated MRP6 mutation. As discussed above, preferred mutations to be screened for are those shown in Table 1. However, additional mutations identified according to the invention are also useful as markers of PXE, including deletions in the (MRP6) ABCC6 locus.

According to one embodiment of the invention, a diagnostic test can be a nucleic scanning test where the assay detects the presence of a mutation in the nucleic acid being interrogated. In an alternative embodiment, a diagnostic test can interrogate a nucleic acid for the presence of a specific mutation.

According to this invention, base pair deletions or alterations leading to the omission of amino acid residues in the gene product are determined. Nucleic acid primers and probes are used in a variety of PCR-based amplification and hybridization assays to screen for and detect the presence of defective ABCC6 gene or mRNA in a patient. The genetic information derived from the intron/exon boundaries is also very useful in various screening and diagnosis procedures.

Various nucleic acid scanning methods are used for scanning the MRP6 genomic, mRNA or cDNA sequence obtained from a patient for detecting, for example, large deletions and substitutions in the sequence that would be indicative of the disease. These nucleic acid scanning techniques include PCR-based techniques and using oligonucleotide probes that hybridize to specific regions of the gene.

In one embodiment of the invention, preferred mutations for nucleic acid scanning techniques include large deletions in the genomic sequence for the ABCC6 gene for example a 16.5 kb deletion spanning from exon 22 to exon 29. Primers are designed to various regions of the ABCC6 gene which are used for PCR-based detection of large deletions in the gene.

In another embodiment of the invention, primers are designed to the ABCC6 gene that are able to differentiate between the size of the amplified wild-type sequence and sequence containing a specific mutation, for example a deletion.

In a preferred embodiment of the invention, nucleic acid probes are provided which comprise either ribonucleic or deoxyribonucleic acids. Typically, the size of the probes varies from approximately 18 to 22 nucleotides. Functionally, the probe is long enough to bind specifically to the homologous region of the ABCC6 gene, but short enough such that a difference of one nucleotide between the probe and the DNA being tested disrupts hybridization. Thus the nucleic acid probes of the present invention are capable of detecting single nucleotide changes in the ABCC6 gene.

In a preferred embodiment of the invention, nucleic acid probes are 100% homologous to a mutant allele of the ABCC6 gene, but not to the wild-type gene.

In another embodiment of the invention, the nucleic acid probes are 100% homologous to the wild-type allele. Accordingly, the invention provides methods for determining whether an individual is homozygous or heterozygous for a particular allele using both a wild-type and an allele-specific probe.

According to one method of the invention, mutations are detected by sequencing lo specific regions of the ABCC6 gene. In a preferred embodiment, the specific regions encompass one or more mutations presented in Table 1. In an alternative embodiment, a specific region being interrogated includes one of exons 1-31. Preferred exons include exons 25-29, and more preferably exon 28 in which many PXE associated mutations have been identified.

According to still other methods of the present invention rapid screening techniques are used to determine whether exons of the ABCC6 gene carry any mutations. Such techniques can be followed by one of the techniques already described above which are specific for a particular allele or mutation. One such rapid screening technique involves the determination of the conformation of single strands of DNA which have been amplified from exon sequences that are known to carry mutations, including the mutations presented in Table 1. The single strands are run in non-denaturing electrophoretic gels, such as are typically used for sequencing DNA. The mobility of single stranded DNA on such gels is sensitive to the conformation of the DNA fragments. The conformation of the single stranded DNA is dependent on its base sequence, alterations in even one base affecting the conformation. Thus the presence of a wild-type or mutant allele described herein can be detected by amplifying an exon sequence, denaturing the duplex molecules, and separating them on the basis of their conformation on non-denaturing polyacrylamide gels. If mutant alleles are present, they will have a different mobility than wild-type sequences amplified with the same primers. Most conveniently, the amplified sequences will be radiolabeled to facilitate visualization on gels. This can be readily accomplished using labeled primers or a labeled nucleotide. For a general reference on this technique see Orira, et al., Genomics vol. 5, pp. 874-879 (1989). A preferred nucleic acid amplification product for SSCP analysis is between about 100 and 500 bp, and more preferably between about 140 and 300 bp.

According to another rapid screening technique of the present invention, an amplified fragment containing a mutation is detected using denaturing gradient gel electrophoresis (DGGE). For a general reference on this technique see Sheffield, et al., Proc. Natl. Acad. Sci. vol. 86, pp. 232-236 (1989). Briefly, double stranded fragments which are generated by amplification (PCR) can be subjected to DGGE. "DGGE is a gel system that separates DNA fragments according to their melting properties. When a DNA fragment is electrophoresed through a linearly increasing gradient of denaturants, the fragment remains double stranded until it reaches the concentration of denaturants equivalent to a melting temperature (Tm) that causes the lower-temperature melting domains of the fragment to melt. At this point, the branching of the molecule caused by partial melting sharply decreases the mobility of the fragment in the gel. The lower-temperature melting domains of DNA fragments differing by as little as a single-base substitution will melt at slightly different denaturant concentrations because of differences in stacking interactions between adjacent bases in each DNA strand. These differences in melting cause two DNA fragments to begin slowing down at different levels in the gel, resulting in their separation from each other." Sheffield, et al., ibid. Use of a GC clamp as taught in Myers et al., Nucleic Acids Res. vol. 13, pp. 3111-3146 (1985) increases the sensitivity of detection of this method from about 40% to about 100%. If mismatches are present, which would be the case if the DNA sample amplified was heterozygous for an ABCC6 allele, they will be visible on these DGGE gels. Double stranded fragments containing one wild-type strand and one mutant strand will have a different mobility on these gels than will double stranded fragments which contain two wild-type or two mutant strands, due to the different melting temperatures of these species. Thus, the melting temperature of fragments amplified from different regions of the ABCC6 gene can be determined by DGGE and can be used to indicate whether a mutant allele is present.

In one embodiment, a region of the (MRP6) ABCC6 gene that encodes an important functional domain of the (MRP6) ABCC6 protein is screened for the presence of any mutation. For example, a preferred diagnostic assay interrogates the region of the (MRP6) ABCC6 gene that encodes an ATP binding site of the (MRP6) ABCC6 protein, a region that encodes a hydrophobic transmembrane domain, or a region that encodes a conserved amino acid, preferably in the C-terminal half of the MRP6 protein.

One major application of the nucleic acid based diagnostics is in the area of genetic testing, carrier detection and prenatal diagnosis. Individuals carrying mutations in the ABCC6 gene (disease carrier or patients) may be detected at the DNA level with the use of a variety of techniques. The genomic DNA used for the diagnosis may be used directly for detecting specific sequences or may be amplified enzymatically in vitro, for example by PCR. The detection of specific DNA sequence may be achieved by methods such as hybridization using specific oligonucleotides (Wallace et al. Cold Spring Harbour Symp. Quant. Biol. 51: 257-261 (1986)), direct DNA sequencing (Church and Gilbert, Proc. Nat. Acad. Sci. U.S.A. 81: 1991-1995 (1988)), the use of restriction enzymes (Flavell et al. Cell 15: 25 (1978), Geever et al Proc. Nat. Acad. Sci. U.S.A. 78: 5081 (1981)), discrimination on the basis of electrophoretic mobility in gels with denaturing reagent (Myers and Maniatis, Cold Spring Harbour Sym. Quant. Biol. 51: 275-284 (1986)), RNase protection (Myers, R. M., Larin, J., and T. Maniatis Science 230: 1242 (1985)), chemical cleavage (Cotton et al Proc. Nat. Acad. Sci. U.S.A. 85: 4397-4401, (1985)) and the ligase-mediated detection procedure (Landegren et al Science 241:1077 (1988)).

Oligonucleotides specific to normal or mutant sequences are chemically synthesized using commercially available machines, labelled radioactively with isotopes or non-radioactively (with tags such as biotin (Ward and Langer et al. Proc. Nat. Acad. Sci. U.S.A. 78: 6633-6657 (1981)), and hybridized to individual DNA samples immobilized on membranes or other solid supports by dot-blot or transfer from gels after electrophoresis. The presence or absence of these specific sequences are visualized by methods such as autoradiography or fluorometric (Landegren et al, 1989) or colorimetric reactions (Gebeyshu et al. Nucleic Acids Research 15:.4513-4534 (1987)).

Sequence differences between normal and mutants may be revealed by the direct DNA sequencing method of Church and Gilbert. Cloned DNA segments may be used as probes to detect specific DNA segments. The sensitivity of this method is greatly enhanced when combined with PCR (Wrichnik et al, Nucleic Acids Res. 15:529-542 (1987); Wong et al, Nature 330:384-386 (1987); Stoflet et al, Science 239:491-494 (1988)). In the latter procedure, a sequencing primer which lies within the amplified sequence is used with double-stranded PCR product or single-stranded template generated by a modified PCR. The sequence determination is performed by conventional procedures with radiolabeled nucleotides or by automatic sequencing procedures with fluorescent-tags.

Genetic testing based on DNA sequence differences may be achieved by detection of alteration in electrophoretic mobility of DNA fragments in gels with or without denaturing reagent. Small sequence deletions and insertions can be visualized by high resolution gel electrophoresis. For example, a PCR product with a small deletion is clearly distinguishable from the normal sequence on an 8% non-denaturing polyacrylamide gel. DNA fragments of different sequence compositions may be distinguished on denaturing formamide gradient gel in which the mobilities of different DNA fragments are retarded in the gel at different positions according to their specific "partial-melting" temperature (Myers, supra). In addition, sequence alterations, in particular small deletions, may be detected as changes in the migration pattern of DNA heteroduplexes in non-denaturing gel electrophoresis, as have been detected for the 3 dp (I507) mutation and in other experimental systems (Nagamine et al, Am. J. Hum. Genet, 45:337-339 (1989)). Alternatively, a method of detecting a mutation comprising a single base substitution or other small change could be based on differential primer length in a PCR. For example, one invariant primer could be used in addition to a primer specific for a mutation. The PCR products of the normal and mutant genes can then be differentially detected in acrylamide gels.

Sequence alterations may occasionally generate fortuitous restriction enzyme recognition sites which are revealed-by the use of appropriate enzyme digestion followed by conventional gel-blot hybridization (Southern, J. Mol. Biol 98: 503 (1975)). DNA fragments carrying the site (either normal or mutant) are detected by their reduction in size or increase of corresponding restriction fragment numbers. Genomic DNA samples may also be amplified by PCR prior to treatment with the appropriate restriction enzyme; fragments of different sizes are then visualized under UV light in the presence of ethidium bromide after gel electrophoresis.

In another embodiment of the invention, sequence changes at specific locations may also be revealed by nuclease protection assays, such as RNase (Myers, supra) and S1 protection (Berk, A. J., and P. A. Sharpe Proc. Nat. Acad. Sci. U.S.A. 75: 1274 (1978)), the chemical cleavage method (Cotton, supra) or the ligase-mediated detection procedure (Landegren supra).

In addition to conventional gel-electrophoresis and blot-hybridization methods, DNA fragments may also be visualized by methods where the individual DNA samples are not immobilized on membranes. The probe and target sequences may be both in solution or the probe sequence may be immobilized (Saiki et al, Proc. Natl. Acad. Sci USA, 86:6230-6234 (1989)). A variety of detection methods, such as autoradiography involving radioisotopes, direct detection of radioactive decay (in the presence or absence of scintillant), spectrophotometry involving colorigenic reactions and fluorometry involving fluorogenic reactions, may be used to identify specific individual genotypes.

In a preferred embodiment of the invention, for example, a PCR with multiple, specific oligonucleotide primers and hybridization probes, may be used to identify a plurality of possible mutations at the same time (Chamberlain et al. Nucleic Acids Research 16: 1141-1155 (1988)). The procedure may involve immobilized sequence-specific oligonucleotides probes (Saiki et al, supra).

According to the invention, assays are performed to detect a deletion within or including the MRP6 gene using Southern hybridization, FISH analysis, or diagnostic PCR. It is expected that most deletions will occur between repetitive Alu sequences that are common within the introns of the MRP6 gene. Preferred PCR primers for detecting these deletions are primers that flank intron Alu sequences.

According to one aspect of the invention, many of the PXE associated MRP6 mutations are found in exons 22-30. Accordingly, preferred assays of the invention interrogate any one of exons 22-30, taken alone or in combination, for the presence of a PXE associated MRP6 mutation.

In a preferred embodiment of the invention, a diagnostic assay interrogates the entire (MRP6) ABCC6 locus for the presence of a mutation, using for example SSCP, HA, or CSGE, and direct sequencing. In a more preferred embodiment, an assay interrogates a portion of the ABCC6 locus for the presence of a mutation. If a mutation is detected, it is first compared to known mutations associated with PXE (Table 1) and known neutral polymorphisms (Table 2) that are not associated with PXE. If the mutation has not yet been observed as either a PXE associated mutation or as a neutral polymorphism, the nature of the mutation is considered. If the mutation is a deletion, nonsense, frameshift or other mutation that affects expression of a normal MRP6 protein, the mutation is considered to be a PXE mutation. Similarly, if the mutation results in a nonconservative amino acid change or an amino acid change in a conserved sequence such as an NBF, a transmembrane sequence, or a change in a conserved amino acid shown in FIG. 3, the mutation is considered to be a PXE mutation. In addition, if the mutation results in low levels of MRP6 expression, the mutation is considered to be a PXE mutation. However, if the mutation results in a conservative amino acid change in a non-conserved part of the MRP6 protein the mutation is considered to be a neutral polymorphism. Nonetheless, a patient identified with a previously unknown neutral polymorphism according to this analysis should be subjected to additional diagnostic tests to look for known PXE associated symptoms or subclinical symptoms.

According to one aspect of the invention, the detection of PXE carriers and PXE patients is determined through the identification of mutant MRP6 alleles in DNA from patients, family members and apparently unrelated and normal individuals. A single allele, with no evidence of a second mutant allele and the presence of a normal allele will be considered a carrier. Patients may be identified as either compound heterozygotes (having two different mutant alleles) or homozygotes (two identical mutant alleles).

b) Protein Based Diagnostics

Different approaches to a MRP6 protein-based diagnostic assay can be used to detect the presence of a PXE related mutation in a patient. Preferred assays include detecting a mutant electrophoretic mobility, the presence of a mutant epitope, the absence of a normal epitope, or by identifying altered biological activity, for example altered ATP binding or altered transport of a synthetic, preferably radiolabeled molecule.

In one embodiment, diagnosis can be achieved by monitoring differences in the electrophoretic mobility of normal and mutant proteins. Such an approach will be particularly useful in identifying mutants in which charge substitutions are present, or in which insertions, deletions or substitutions have resulted in a significant change in the electrophoretic migration of the resultant protein. Alternatively, diagnosis may be based upon differences in the proteolytic cleavage patterns of normal and mutant proteins, differences in molar ratios of the various amino acid residues, or by functional assays demonstrating altered function of the gene products.

In preferred embodiments, protein-based diagnostics will employ differences in the ability of antibodies to bind to normal and mutant MRP6 proteins. Such diagnostic tests may employ antibodies which bind to the normal proteins but not to mutant proteins, or vice versa. In particular, an assay in which a plurality of monoclonal antibodies, each capable of binding to a mutant epitope, may be employed. The levels of anti-mutant antibody binding in a sample obtained from a test subject (visualized by, for example, radiolabelling, ELISA or chemiluminescence) may be compared to the levels of binding to a control sample. Alternatively, antibodies which bind to normal but not to mutant MRP6 protein may be employed, and decreases in the level of antibody binding may be used to distinguish homozygous normal individuals from mutant heterozygotes or homozygotes. Such antibody diagnostics may be used for in situ immunohistochemistry using biopsy samples of tissues obtained from patients.

c) Genetic Counseling

According to one embodiment of the invention, genetic counseling is provided to an individual identified as a PXE carrier, a PXE homozygote, or a PXE compound heterozygote (an individual with two different PXE mutant alleles). According to the invention, individuals carrying two PXE mutant alleles are provided information about ameliorating treatments for some of the symptoms of PXE. For example, a person who inherits PXE recessively is cautioned with regard to diet and activity. A low fat, high fibre, heart healthy diet is critical for maintaining cardiovascular health. Regular exercise appears to alleviate some of the symptoms of peripheral vascular disease. Medications to allow the passage of blood through narrowed arteries may be recommended. Individuals exhibiting eye manifestations should not engage in activities that put them at risk for injury to the eye that could subsequently lead to hemorrhage and vision loss. Smoking should be avoided at all costs since it appears to increase the rate and severity of eye disease. In one embodiment of the invention, a patient identified as being a carrier of a PXE associated mutation or as being a homozygote or a compound heterozygote for PXE associated mutations should be advised to reduce calcium intake or to use drugs that reduce calcium intake in order to reduce the severity of the phenotype.

III. Therapeutic Applications

The present invention provides a basis for therapeutic treatments of PXE related symptoms caused by mutations at the (MRP6) ABCC6 locus. According to the invention, normal (MRP6) ABCC6 nucleic acid or protein is provided to cells and/or a patient having a PXE associated mutation at the (MRP6) ABCC6 locus.

Preferred target tissues include the kidney and liver, but also other tissues where low levels of MRP6 expression have been observed, such as smooth muscle cells arid macrophages. Preferred target tissues also include tissues or cells that exhibit PXE related symptoms, such as a blood vessel, the gastrointestinal tract, occular tissue, the urinary tract, and skin.

a) Nucleic Acid-based Therapeutics

According to the invention, PXE or PXE associated symptoms can be prevented or treated by providing a normal PXE gene or cDNA to a patient that is diagnosed as having on or more PXE associated mutations at the (MRP6) ABCC6 locus. The fact that PXE is a recessive disease makes it particularly amenable to gene therapy, because it is expected that most, if not all, PXE associated MRP6 mutations reduce the amount of functional MRP6 protein in a cell and can be compensated for by providing normal MRP6 to the cell.

In one series of embodiments, normal copies of the MRP6 gene are introduced into patients to code successfully for normal protein in one or more different affected cell types. The gene must be delivered to those cells in a form in which it can be taken up and code for sufficient protein to provide effective function. Thus, it is preferred that the recombinant gene be operably joined to a strong promoter so as to provide a high level of expression which will compensate for the absence of sufficient amounts of normal MRP6. As noted above, the recombinant construct may contain endogenous or exogenous regulatory elements, inducible or repressible regulatory elements, or tissue-specific regulatory elements.

Preferred vectors for introducing an MRP6 gene to a cell or a patient include retroviral vectors, because of their high efficiency of infection and stable integration and expression. Other viral vectors which can be used include adeno-associated virus, vaccinia virus, bovine papilloma virus, or a herpes virus such as Epstein-Barr virus. Alternative vectors include plasmids that are replicated in human cells.

In another series of embodiments, a mutant MRP6 gene may be replaced by homologous recombination with a recombinant construct. The recombinant construct preferably contains a normal copy of the MRP6 gene. Alternatively, a regulatory region of a normal MRP6 gene in a PXE carrier may be altered to increase expression of normal MRP6.

i) Wild Type Genes

In one series of embodiments, a normal human (MRP6) ABCC6 gene is introduced to cells or a patient. A normal (MRP6) ABCC6 gene includes a gene with one or more polymorphic variations that are not associated with PXE. In one embodiment, an MRP6 genomic sequence is used. In an alternative embodiment an MRP6 cDNA sequence is used.

ii) Related Genes

In an alternative series of embodiments, an (MRP6) ABCC6 related gene is provided to a cell or tissue having a PXE associated mutation. According to the invention, an (MRP6) ABCC6 related gene encodes a protein that has similar functional properties as a normal human MRP6 protein and can compensate for the absence of sufficient amounts of normal human MRP6 protein in a patient cell or tissue. Preferably, an (MRP6) ABCC6 homologue from another mammalian species is used. For example the mouse or rat MRP6 genes or cDNAs could be used. In one embodiment of the invention, a homologue from a non-mammalian species is used. Alternatively, a nucleic acid encoding a different ABC protein is used, for example an MRP1 encoding nucleic acid.

The present invention also provides for cells or cell lines, both prokaryotic and eukaryotic, which have been transformed or transfected with the nucleic acids of the present invention so as to cause clonial propagation of those nucleic acids and/or expression of the proteins or peptides encoded thereby. Such cells or cell lines will have utility both in the propagation and production of the nucleic acids and proteins of the present invention but also, as further described herein, as model systems for diagnostic and therapeutic assays. As used herein, the term “transformed cell” is intended to embrace any cell, or the descendant of any cell, into which has been introduced any of the nucleic acids of the invention, whether by transformation, transfection, infection, or other means. Methods of producing appropriate vectors, transforming cells with those vectors, and identifying transformants are well known in the art.

b) Protein Based Therapeutics

Treatment of PXE symptoms may be performed by directly providing normal protein to a patient cell or tissue. Sufficient amounts of substantially pure MRP6 protein can be obtained from cultured cell systems which express the protein. Delivery of the protein to the affected tissue can then be accomplished using appropriate packaging or administrating systems including, for example, liposome mediated protein delivery to the target cells.

c) Drug Therapies

In one embodiment of the invention, a drug identified according to methods of the invention is administered to a patient diagnosed with PXE or a PXE carrier with PXE related symptoms. Alternatively, a drug is administered to prevent or minimize the development of PXE or PXE associated symptoms in individuals identified as having one or more PXE mutations at the ABCC6 locus.

IV. Drug Discovery Applications

The present invention provides a basis for screening drug candidates to identify useful therapeutic compositions to treat or alleviate the symptoms of PXE. In a series of embodiments, the invention provides screens based on MRP6 activity. As used with respect to this series of embodiments, the term "activity" broadly includes gene and protein expression, protein post-translation processing, trafficking and localization, and any functional activity (e.g., enzymatic, receptor-effector, binding, channel), as well as downstream effects of any of these. MRP6 appears to be an integral membrane protein and may have transport related functions, and it also has ATP binding cassettes. Accordingly, these functional properties can be used as a basis for a screen to identify compounds that increase MRP6 function.

In one embodiment, a drug candidate is screened for its ability to increase expression of the MRP6 gene. A preferred screen monitors the level of normal MRP6 mRNA in cells grown in culture in the presence and absence of the candidate compound. Alternatively, normal MRP6 protein levels are monitored. Useful cells for these assays are preferably normal cells or PXE carrier cells. However, a PXE cell can also be used and the levels of mutant MRP6 expression can also be monitored. A compound that increases the level of MRP6 expression is particularly useful to treat a PXE carrier in order to increase the level of MRP6 expressed from the normal allele. However, a compound that increases the level of MRP6 expression can also be useful to treat a PXE homozygote or compound heterozygote if the PXE associated MRP6 allele(s) encodes an MRP6 protein that retains some normal MRP6 function or if the allele is a mutation that reduces the level of normal MRP6 function.

Other assays are useful for screening candidate compounds to identify a compound that increases normal MRP6 function. In one embodiment, an assay screens a compound for the ability to restore normal phenotype to dermal fibroblasts isolated from a PXE patient. Dermal fibroblasts isolated from patients with PXE exhibit abnormal phenotype when grown in vitro (Quaglino et al., Biochimica et Biophysica Acta 1501 (2000) 51-62). These phenotypes include an increased proliferation index compared to normal fibroblasts when grown in monolayer. PXE fibroblasts also have lower adhesion properties to collagen type I and to plasma fibronectin when compared to normal fibroblasts. Accordingly, these phenotypes provide a basis for an assay to identify a compound that restores normal MRP6 function to dermal fibroblasts isolated from a patient that was identified as having a PXE associated MRP6 mutation.

In another embodiment of the invention, an assay is used to screen candidate compounds for their ability to increase the ATPase activity of an MRP6 proteins. In a preferred embodiment, the assay monitors the ATPase activity of all MRP6 protein encoded by an MRP6 gene with a PXE associated mutation in the presence and absence of the candidate compound. ATPase activity of purified MRP6 can be assayed according to methods known in the art (see, for example, Mao et al., Biochimica et Biophysica Acta 1461, 69-82 (1999). According to the invention, a compound that increases the ATPase activity of a PXE associated MRP6 protein variant is useful to treat a patient that is heterozygous or homozygous for the PXE allele that encodes the protein variant used in the assay.

In a similar embodiment of the invention, an assay is used to screen candidate compounds for their ability to increase the transport activities of an MRP6 protein, in particular a PXE associated MRP6 protein variant. A useful transport assay is provided in Oude et al., Biochim Biophys Acta, 1241(2), 215-68, 1995. A compound identified according to this screen is useful to treat PXE patients and PXE carriers as described above.

V. Disease Models

The invention provides a basis for designing cellular and animal models of PXE. Such models are useful to study the development of the PXE disease in PXE homozygotes and compound heterozygotes and to identify potential PXE associated physiological dysfunctions in PXE carriers. Such models are also useful in screens to identify therapeutic compounds to prevent or treat PXE symptoms.

a) Cellular Models

According to the invention, cellular models can be made by deleting one or both MRP6 alleles, or by introducing one or more PXE associated MRP6 alleles into a cell line grown in vitro, using methods known in the art. Preferred cell lines include renal and hepatic cell lines. Other useful cell lines include those derived from skin (keratinocytes and fibroblasts) and ocular tissue (ganglioma cells).

b) Animal Models

The present invention also provides for the production of transgenic non-human animal models for the study of PXE, for the screening of candidate pharmaceutical compounds, and for the evaluation of potential therapeutic interventions.

Animal species which suitable for use in the animal models of the present invention include, but are not limited to, rats, mice, hamsters, guinea pigs, rabbits, dogs, cats, goats, sheep, pigs, and non-human primates (e.g., Rhesus monkeys, chimpanzees). For initial studies, transgenic rodents (e.g., mice) are preferred due to their relative ease of maintenance and shorter life spans. Transgenic yeast or invertebrates (e.g., nematodes, insects) may be preferred for some studies because they will allow for even more rapid and inexpensive screening. Transgenic non-human primates, however, may be preferred for longer term studies due to their greater similarity to humans.

Based on the identification of MRP6 as the gene associated with PXE, there are now several available approaches for the creation of a transgenic animal models for PXE, including animal models with one or both MRP6 alleles deleted and animal models with one or two MRP6 alleles with mutations similar to known PXE associated human MRP6 mutations.

To create an animal model (e.g., a transgenic mouse), a mutant MRP6 gene can be inserted into a germ line or stem cell using standard techniques of oocyte microinjection, or transfection or microinjection into embryonic stem cells. Animals produced by these or similar processes are referred to as transgenic. If the mutation knocks out the MRP6 gene or a portion thereof, the animals are referred to as knockouts.

For oocyte injection, one or more copies of the recombinant DNA constructs of the present invention may be inserted into the pronucleus of a just-fertilized oocyte. This oocyte is then reimplanted into a pseudo-pregnant foster mother. The liveborn animals are screened for integrants using analysis of DNA (e.g., from the tail veins of offspring mice) for the presence of the inserted recombinant transgene sequences. The transgene may be either a complete genomic sequence injected as a YAC, BAC, PAC or other chromosome DNA fragment, a cDNA with either the natural promoter or a heterologous promoter, or a minigene containing all of the coding region and other elements found to be necessary for optimum expression.

Retroviral infection of early embryos can also be done to insert the recombinant DNA constructs of the invention. In this method, the transgene is inserted into a retroviral vector which is used to infect embryos (e.g., mouse or non-human primate embryos) directly during the early stages of development to generate chimeras, some of which will lead to germline transmission.

Homologous recombination using stem cells allows for the screening of gene transfer cells to identify the rare homologous recombination events. Once identified, these can be used to generate chimeras by injection of blastocysts, and a proportion of the resulting animals will show germline transmission from the recombinant line. In a preferred embodiment, inactivation of the MRP6 gene in mice may be accomplished by designing a DNA fragment which contains sequences from an MRP6 exon flanking a selectable marker. Homologous recombination leads to the insertion of the marker sequences in the middle of an exon, causing inactivation of the MRP6 gene and/or deletion of internal sequences. DNA analysis of individual clones can then be used to recognize the homologous recombination events.

The techniques of generating transgenic animals, as well as the techniques for homologous recombination or gene targeting, are now widely accepted and practiced. A laboratory manual on the manipulation of the mouse embryo, for example, is available detailing standard laboratory techniques for the production of transgenic mice (Hogan et al., 1986). A large number vectors are available to accomplish this and appropriate sources of genomic DNA for mouse and other animal genomes to be targeted are commercially available from companies such as GenomeSystems Inc. (St. Louis, Mo., USA). The typical feature of these targeting vector constructs is that 2 to 4 kb of genomic DNA is ligated 5' to a selectable marker (e.g., a bacterial neomycin resistance gene under its own promoter element termed a "neomycin cassette"). A second DNA fragment from the gene of interest is then ligated downstream of the neomycin cassette but upstream of a second selectable marker (e.g., thymidine kinase). The DNA fragments are chosen such that mutant sequences can be introduced into the germ line of the targeted animal by homologous replacement of the endogenous sequences by either one of the sequences included in the vector. Alternatively, the sequences can be chosen to cause deletion of sequences that would normally reside between the left and right arms of the vector surrounding the neomycin cassette. The former is known as a knock-in, the latter is known as a knock-out. Example 5 describes a knockout of most of exons 28 and 29 in mouse MRP6.

VI. (MRP6) ABCC6 Interacting Molecules

According to the invention, molecules that interact with a normal MRP6 gene product gene product provide candidates 1) for identifying additional types of mutations that result in a PXE phenotype and 2) for additional levels of therapeutic intervention to overcome or minimize the effect of a mutant PXE gene product. For example, the identification of a protein that interacts with a normal MRP6 protein but not with a PXE mutant protein provides a potential target for therapeutic intervention if the function of the interacting protein can be modified to compensate for the absence of normal MRP6 protein.

According to the invention, (MRP6) ABCC6 interacting molecules can be identified according to a number of biochemical and genetic methods known in the art, including affinity chromatography, mutational analysis, and yeast two hybrid analysis. As will be obvious to one of ordinary skill in the art, there are numerous other methods of screening individual proteins or other compounds, as well as large libraries of proteins or other compounds (e.g., phage display libraries and cloning systems from Stratagene, La Jolla, Calif.) to identify molecules which bind to normal or mutant MRP6 proteins. All of these methods comprise the step of mixing a normal or mutant MRP6 protein or protein fragment with test compounds, allowing for binding (if any), and assaying for bound complexes.

The invention is further illustrated by the following non-limiting examples.

EXAMPLES

Example 1

Materials and Methods a) Sources of Patient Samples

PXE International, Inc.

To date, PXE International has assembled a database of over 2100 PXE patients from 1400 families from 31 countries including North America, several European and South American countries and South Africa. From this cohort of patients and family members, genomic DNA has been prepared from whole blood samples obtained from over 1200 PXE patients and family members.

Honolulu Heart Program

In the early 1950's, studies around the world were reporting geographic differences in coronary heart disease (CHD) mortality, pathology, prevalence, and incidence. Among these reports were those of significant differences in the CHD and cerebrovascular disease rates in Japan and in the United States. The overall mortality for men in Japan and in the United States was similar, but the rates for CHD were strikingly different. Reported CHD mortality among Japanese was approximately twenty percent of that among U.S. Caucasians. At about the same time, Japanese living in Hawaii and California were reported to have a lower overall mortality than either U.S. Caucasians or Japanese living in Japan. The reasons for these differences were not apparent. However, it was felt that the study of these populations might offer important clues to the etiology of heart and vascular disease. The compared populations, living in Japan, Hawaii and California were of Japanese ancestry to limit genetic variation between study groups. The Honolulu cohort of the Ni-Hon-San (Nippon-Honolulu, San Francisco) study formed the basis for the Honolulu Heart Program (HHP). That study has now been underway for 35 years, providing extensive information about the role of lifestyle, diet, and other risk factors to development of chronic diseases of major public health importance in 8,000 Japanese-American men.

Although several studies have suggested that PXE is more frequent in females there is no evidence that the observed gender difference is caused by genetic factors. Indeed, men would often report skin lesions, usually the first signs of PXE, later in life, than women. Therefore, a study of an exclusively male cohort from the HHP should not compromise the general applicability of the conclusions. PXE has also no particular predilection for any ethnic or racial group. PXE has indeed largely been described in Caucasians but also in African and Asian populations. PXE cases reported in Japan have shown no phenotypic or prevalencic differences when compared to those observed in Caucasian populations.

Unaffected Control Subjects

DNA has been prepared from 150 unrelated individuals with no evidence of PXE. These samples have been aliquoted and are currently stored at −80° C. They are routinely used as control DNA samples and will be used to confirm that any new and potential mutation detected in a PXE patient or relative is indeed a mutation and not a neutral polymorphism. The donors of these DNA samples were adults of either sex from various ethnic backgrounds.

b) Mutation Detection Methods

Detection of Single Nucleotide Mutations

Single strand conformation polymorphism (SSCP) analysis is based on the observation that single stranded DNA will adopt, in non-denaturing conditions, a secondary structure that is strictly sequence-dependant. Slight variations in sequence, such as a single nucleotide change can alter the conformation of a DNA fragment, which can be resolved on a non-denaturing polyacrylamide gel. Heteroduplex analysis (HA) is based on the observation that heteroduplexes formed between two DNA strands with one or more mismatches have electrophoretical mobility distinctly different from homoduplexes. While both methods (SSCP and HA) can detect point mutations, some sequence variants are more readily detected by one procedure than the other. Accordingly, a preferred screening method, uses a combination of SSCP and modified HA called Conformation-Sensitive Gel Electrophoresis or CSGE.

In a preferred assay, each characterized PCR primer pair is radioactively labeled sing T4 polynucleotide kinase and $\gamma$-[$P^{32}$]-ATP. For SSCP analysis, radiolabeled PCR products are mixed with denaturing loading buffer and loaded onto a 0.5×MDE (MDE is a mutation detection enhancement polyacrylamide-derived matrix provided by FMC products), 0.6×TBE native polyacrylamide gel and electrophoresed overnight at 8 watts in a sequencing gel apparatus. Separated, radiolabeled conformers are visualized by autoradiography. For CSGE, EDTA is added to the incubated PCR reaction mix to a final concentration of 1 mM and the reaction will be heat-denatured and incubated for 60 minutes at 68° C. to allow heteroduplex formation. Heteroduplex products are analyzed on a 6% polyacrylamide gel (29:1 ratio of acrylamide/bisacrylamide), 10% (v/v) ethylene glycol and 15% (w/v) formamide in 0.5×TTE buffer (1×TTE is 89 mM Tris, 15 mM taurine, 0.5 mM EDTA, pH 9.0). A solution of 20% (v/v) ethylene glycol, 30% (w/v) formamide and 0.05% xylene cyanol and bromophenol blue is mixed equally with the samples. The gel is run at 35 to 45 watts for 2 to 4 hours at room temperature. As for SSCP, CSGE conformers are revealed by autoradiography.

When an abnormal conformer or heteroduplex is detected, the segregation of the variant is analyzed for DNA samples from the entire family. Subsequently, the DNA sequence of the variant is determined by eluting normal and altered DNA conformers directly from the electrophoresis gel. These PCR fragments are eluted in water, re-amplified and directly used as a template for sequencing using an ABI 310 automated sequencer (Perking Elmer). A panel of 150 DNA samples of normal unrelated individuals is used to identify abnormal variants that are common polymorphisms in the ABCC6 locus.

Mutation Detection by Enzymatic Cleavage

Single nucleotide substitutions often modify the recognition site of a restriction enzyme. Polymorphisms and mutations can, therefore, be detected in a rapid and convenient manner by the enzymatic cleavage of a PCR fragment containing the nucleotide change. This method is frequently employed to verify the presence of previously characterized mutations or polymorphisms in DNA samples for control, study or diagnostic purposes. It can also be used for screening a large number of samples. Out of the ABCC6 mutations listed in Table 1, 10 mutations were identified with a unique restriction pattern. For example, three possible HhaI restriction profiles for one of these mutations. R1339C (4015C to T) can be visualized by electrophoresis. According to the invention, single nucleotide mutations in ABCC6 are detectable by enzymatic cleavage. Accordingly, this method is useful as an initial step to appropriately complement the screening of large cohorts with more traditional mutations detection techniques.

PCR Mapping

A single base substitution mutation may be detected based on differential PCR product length or production in PCR. Thus, primers which span mutant sites or which, preferably, have 3' termini at mutation sites, may be employed to amplify a sample of genomic DNA, mRNA or cDNA from a subject. A mismatch at a mutational site may be expected to alter the ability of the normal or mutant primers to promote the polymerase reaction and, thereby, result in product profiles which differ between normal subjects and heterozygous and/or homozygous MRP6 mutants. The PCR products of the normal and mutant gene may be differentially separated and detected by standard techniques, such as polyacrylamide or agarose gel electrophoresis and visualization with labeled probes, ethidium bromide or the like. Because of possible non-specific priming or readthrough of mutation sites, as well as the fact that most carriers of mutant alleles will be heterozygous, the power of this technique may be low.

Electrophoretic Mobility

Genetic testing based on DNA sequence differences also may be achieved by detection of alterations in electrophoretic mobility of DNA, mRNA or cDNA fragments in gels. Small sequence deletions and insertions, for example, can be visualized by high resolution gel electrophoresis of single or double stranded DNA, or as changes in the migration pattern of DNA heteroduplexes in non-denaturing gel electrophoresis. MRP6 mutations or polymorphisms may also be detected by methods which exploit mobility shifts due to single-stranded conformational polymorphisms (SSCP) associated with mRNA or single-stranded DNA secondary structures.

Chemical Cleavage of Mismatches

Mutations in MRP6 may also be detected by employing the chemical cleavage of mismatch (CCM) method. In this technique, probes (up to ~1 kb) may be mixed with a sample of genomic DNA, cDNA or mRNA obtained from a subject. The sample and probes are mixed and subjected to conditions which allow for heteroduplex formation (if any). Preferably, both the probe and sample nucleic acids are double-stranded, or the probe and sample may be PCR amplified together, to ensure creation of all possible mismatch heteroduplexes. Mismatched T residues are reactive to osmium tetroxide and mismatched C residues are reactive to hydroxylamine. Because each mismatched A will be accompanied by a mismatched T, and each mismatched G will be accompanied by a mismatched C, any nucleotide differences between the probe and sample (including small insertions or deletions) will lead to the formation of at least one reactive heteroduplex. After treatment with osmium tetroxide and/or hydroxylamine to modify any mismatch sites, the mixture is subjected to chemical cleavage at any modified mismatch sites by, for example, reaction with piperidine. The mixture may then be analyzed by standard techniques such as gel electrophoresis to detect cleavage products which would indicate mismatches between the probe and sample.

Other Methods

Various other methods of detecting MRP6 mutations, based upon the MRP6 sequences disclosed and otherwise enabled herein, will be apparent to those of ordinary skill in the art. Any of these may be employed in accordance with the present invention. These include, but are not limited to, nuclease protection assays (S1 or ligase-mediated), ligated PCR, denaturing gradient gel electrophoresis (DGGE), restriction endonuclease fingerprinting combined with SSCP (REF-SSCP), and the like.

Methods for Analyzing MRP6 mRNA Levels:

The steady state levels of (MRP6) ABCC6 mRNA was analyzed in skin fibroblasts from a PXE patient carrying a homozygous R1141X mutation. Total skin fibroblast RNA from an unaffected control individual and a PXE patient was used to synthesize single stranded cDNA using oligo(dT). PCR primers derived from (MRP6) ABCC6 mRNA sequence were then used in two consecutive rounds of 25 cycles of PCR. Poly(A)+ RNA from normal human kidney (obtained from Clontech) was used as a positive control for detection of (MRP6) ABCC6 mRNA. MRP-1 mRNA was detected in the same cDNA samples used for ABCC6 mRNA with 30 cycles of PCR. The 390 bp and 180 bp DNA fragments detected correspond to the expected size of (MRP6) ABCC6 and MRP-1 mRNA domains encoded within exons 6-9 and 2-3 of the (MRP6) ABCC6 and MRP-1 genes respectively. No reverse transcriptase (No RT) controls were included to confirm that no PCR products were obtained in the absence of cDNA synthesis.

Stringent Hybridization Conditions

High stringency conditions are at least equivalent to a temperature in the range of about 40-70 degrees C., and between about 0.05 and 0.5 M sodium ion. High stringency hybridization conditions are well known in the art and can be optimized for a specific oligonucleotide based on the length and GC content of the oligonucleotide as described in, for example, Sambrook et al., Molecular Cloning, A Laboratory Manual (Cold Spring Harbor, N.Y., 1982).

An oligonucleotide selected for hybridizing to the target nucleic acid, whether synthesized chemically or by recombinant DNA methodologies, is isolated and purified using standard techniques and then preferably labeled (e.g., with $^{35}S$ or $^{32}P$) using standard labeling protocols. A sample containing the target nucleic acid then is run on an electrophoresis gel, the dispersed nucleic acids transferred to a nitrocellulose filter and the labeled oligonucleotide exposed to the filter under stringent hybridizing conditions, e.g. 50% formamide, 5×SSPE, 2× Denhardt's solution, 0.1% SDS at 42° C., as described in Sambrook et al. (1989) supra. The filter may then be washed using 2×SSPE, 0.1% SDS at 68° C., and more preferably using 0.1×SSPE, 0.1% SDS at 68° C. Other useful procedures known in the art include solution hybridization, and dot and slot RNA hybridization. Optionally, the amount of the target nucleic acid present in a sample is then quantitated by measuring the radioactivity of hybridized fragments, using standard procedures known in the art.

Example 2

The Positional Cloning of the PXE Gene

Blood samples and skin biopsies from PXE patients and unaffected relatives in the United States ere collected by PXE International Inc., by Dr. Ivonne Pasquali-Ronchetti in Italy, by Dr. F. Michael Pope in the United Kingdom and by Dr. Anne de Paepe in Belgium. Blood samples were obtained from 100 Caucasian control individuals with no family history of PXE. Genomic DNA was isolated from aliquots of blood. Low passage and confluent skin fibroblasts were obtained from 3 mm full thickness skin biopsies using known procedures.

To identify the gene that contains mutations responsible for PXE, the disease locus was confined to a region of about 8 cM between markers D16S500 and- D16S3041. Recombination mapping reduced this large critical region to an 820 kb domain containing six candidate genes. These genes encode an isoform of Myosin Heavy Chain (MYH11), two Multidrug Resistance-associated Proteins (MRP-1 and (MRP6) ABCC6), an unknown protein called pM5 and two identical unknown proteins referred to as UNK. Using a polymorphic microsatellite repeat ($GAAA_{17}$) located at the 5' end of the MRP-1 gene (FIG. 1) an informative meiotic recombination in one PXE patient was identified and this permitted the exclusion of the MYHH11 as a candidate gene and reduced the size of the PXE region to 570 kb and 5 candidate genes. FIG. 1 shows the previously defined PXE locus covering 820 kb between markers D16S3060 and D16S79 at 16p13.1. The BAC contig that covers this region is shown along with the identity of the BACs. FIG. 1*b* shows the gene content of the PXE locus represented from the telomere (left) to the centromere (right). The transcriptional orientation of the genes is indicated by arrows. A flag represents the position of a polymorphic marker ($GAAA_{17}$) used to identify an additional meiotic recombination in one PXE patient that excluded the MYHII gene as the PXE gene.

The 109 exons within the five candidate genes were then screened for mutations by Single-Strand Conformation Polymorphism (SSCP) and Heteroduplex Analysis (HA) using genomic DNA from a cohort of 20 unrelated PXE patients.

Mutation detection, sequence analysis and RT-PCR, SSCP, and Heteroduplex Analysis (HA) were carried out as previously described. Intron-derived primers for PCR amplification of exons present in the genes encoding MRP-1, (MRP6) ABCC6, pM5 and both UNK gene were synthesized using intron sequences available in the TIGR database. PCR products were typically 150-350 bp in length and included complete intron/exon boundaries. Typical PCR reactions, were performed in the presence of .sup.32P-labelled primers in a 9700 thermocycler (Perkin Elmer). Radioactive PCR products were analyzed either by SSCP or HA using MDE polyacrylamide gel (FMC) according to the manufacturer's instructions. DNA conformers were eluted in water from gel slices, re-amplified and sequenced utilizing the same primers used to generate these PCR products. DNA sequence analysis was performed using ABI BigDye terminator cycle sequencing with an ABI310 automated DNA sequencer. The sequence information generated by the sequencer was analyzed using the ABI software. The Sequencher™ 3.1 program (Gene Codes Corporation, Ann Arbor, Mich.) was used to identify variation between the sequence of putative mutations and control sequences. RT-PCR was performed on total RNA from cultured human skin fibroblasts and human kidney poly(A)+ RNA. The sequences of the PCR primers used are: (MRP6) ABCC6: 5'-AGCCACGTTCTGGTGGGTTT-3' (SEQ ID NO: 4); 5'-GGAGGCTTGGGATCACCAAT-3' (SEQ ID NO: 5); MRP-1: 5-CAACTGCATCGTTCTGTTTG-3' (SEQ ID NO: 6); and 5'-ATACTCCTTGAGCCTCTCCA-3' (SEQ ID NO: 7). Following synthesis, PCR products were separated by electrophoresis through 1.2% agarose and visualized by staining with ethidium bromide.

DNA sequence analysis of two conformers detected in PCR products containing exons 19 and 28 of the pM5 gene revealed two private single nucleotide polymorphisms (SNPs) within the intronic sequence flanking these exons (Table 2). These were the only sequence variants detected in the 31 exons of the pM5 gene using a cohort of 20 PXE patients. Screening all eight exons of each of the two UNK genes revealed only one SNP in the first exon of either one or both UNK genes in, 5 PXE patients. This was a silent nucleotide change (C33T) within the $11^{th}$ codon (S11) of the open reading frame of either one or both unknown genes and therefore unrelated to PXE. Screening all 31 exons of the MRP-1 gene in a panel of PXE patients identified several sequence variants (Table 2) that are not functionally related to PXE as they either occurred in intronic sequences or did not encode changes in amino acids. In addition, two missense variants (R633Q and G671V) were seen in exons-14 and 16 in two unrelated PXE patients but these substitutions were unlikely to be responsible for PXE as they were also found in a panel of 200 alleles from unaffected, ethnically matched control individuals.

Finally, in screening the 31 exons of the (MRP6) ABCC6 gene, the first mutations that are clearly responsible for PXE were identified. A C->T substitution within exon 24 (C3421T) of the (MRP6) ABCC6 gene generated a stop codon at position 1141 (R1141X; FIG. 1 and Table 2). FIG. 1*c* shows the intron/exon structure of the (MRP6) ABCC6 gene. Intron sizes are drawn approximately to scale and the exons are numbered from the 5' end of the (MRP6) ABCC6 gene. FIG. 1*d* shows chromatograms of partial DNA sequence from two unrelated PXE patients containing a nonsense and a splice site mutation in exon 24 and intron 21 respectively. In exon 24, the sequence shows a 3421C>T substitution (arrowhead), which would generate a stop codon at position 1141 (R1141X). PXE patients in a consanguineous Italian pedigree were found to be homozygous for this stop codon mutation. In intron 21, a G to T substitution (IVS21+1G>T) was observed within the invariant GT sequence of the donor splice site. This mutation would influence constitutive splicing of (MRP6) ABCC6 pre-mRNA and was found in two unrelated PXE patients as a compound heterozygote in association with either R1141X or R1138Q. FIG. 1*c* shows the sequence of the normal and mutant, nucleotide and amino acid sequences for the nonsense mutation in exon 24 and the splice site variant within intron 21.

Figure 4:
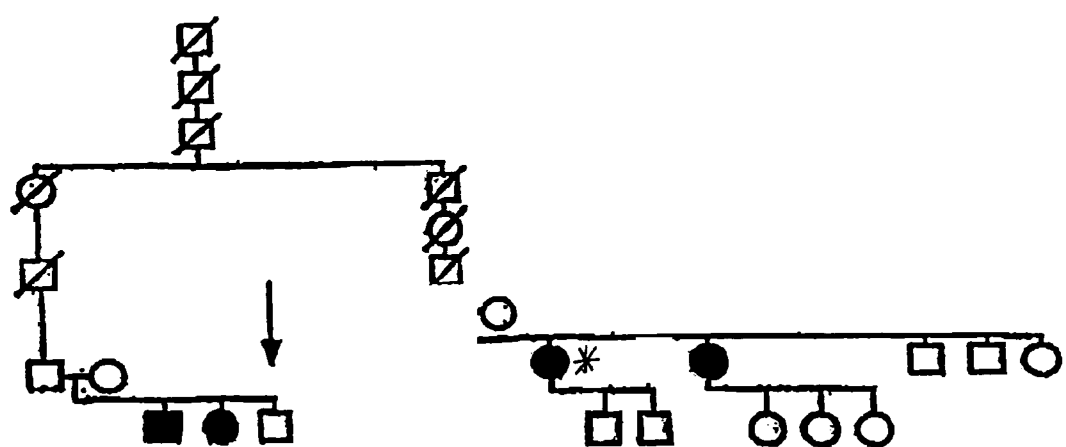
FIG. 4 shows co-segregation of the PXE phenotype with the R1141X mutation in exon 24 of the (MRP6) ABCC6 gene.
Figure 5:
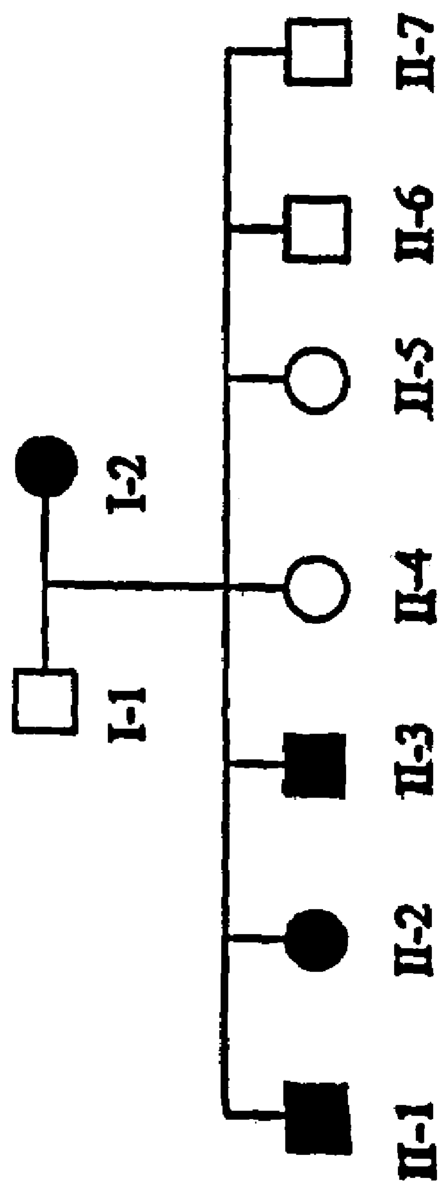
FIG. 5 shows segregation of the PPXE phenotype for an apparent autosomal dominant mutation.

The C3421T variant in exon 24, which was not found in the control panel of 200 normal alleles, co-segregated in a homozygous form with a recessive PXE phenotype in an Italian family in which all unaffected individuals but one were heterozygote carriers (FIG. 4). FIG. 4 shows a large consanguineous Italian pedigree, SSCP conformers for a homozygous variant (R1141X) in exon 24 were noted in all four PXE patients (shaded symbols). All other unaffected family members were heterozygote for this nonsense mutation except one unaffected family member, indicated by an arrow. SSCP conformers from normal unrelated control DNA have been included. Total RNA from the PXE patient indicated by was used for an RT PCR analysis of (MRP6) ABCC6 mRNA and shown to have low levels of MRP6 mRNA.

This R1141X mutation results either in an (MRP6) ABCC6 protein lacking 362 amino acids at the C-terminal domain (FIG. 3) or a null allele, produced through nonsense mediated decay of a truncated (MRP6) ABCC6 mRNA. Indeed, an analysis of steady state (MRP6) ABCC6 mRNA levels in skin fibroblasts from PXE patients of this Italian pedigree indicated the absence of detectable (MRP6) ABCC6 mRNA, suggesting that the homozygous R1141X mutation results in the total loss of MRP6 gene product rather than the production of a truncated protein. R1141X was also found in a homozygous state in unrelated patients with autosomal recessive PXE from the United Kingdom and Belgium. Haplotype analysis of the PXE locus in families with the R1141X mutation revealed that this mutation is travelling within different haplotypes, suggesting that R1141X may be a recurrent mutation.

In two families with a recessive form of PXE from the United Kingdom and the United States, PXE patients were found to be compound heterozygotes. Affected individuals carried a substitution (TVS21+1G>T) affecting the donor-splice site of exon 21 of (MRP6) ABCC6, in association with either the nonsense R1141 X substitution in exon 24 or a missense mutation, R1138Q also in exon 24. The splice site mutation occurred at the donor invariant dinucleotide and lowered the splice potential score from 72.1 to 53.8. Several other missense variants (Table 2) were also found within exon 24 and 28 of the (MRP6) ABCC6 gene. These single nucleotide substitutions, none of which were detected in the control panel of 200 alleles, occurred within highly conserved coding domains, particularly the domain in exon 28 encoding the Walker A region of the second ATP binding fold (FIG. 2).

All the detected homozygous or compound heterozygous mutations were found to be associated with autosomal recessive PXE. One missense mutation (3961G>A) was observed in a family with an apparently dominant form of PXE. All the other heterozygous alterations were detected in individuals with sporadic PXE. The mode of inheritance of these sporadic PXE cases is presently unknown.

Elastic fibers within elastic tissues such as skin and the arterial wall are fragmented and calcified in PXE patients. Dermal and vascular elastic fiber calcification is patchy and does not involve all elastic fibers in these tissues. Therefore, without wishing to be bound by any particular theory, calcification of elastic fibers in PXE is probably therefore, a secondary consequence of a primary defect of either elastic fiber assembly or the interaction of elastic fibers with other extracellular matrix components. Accordingly, MRP6 function is more likely to be related to fiber assembly or matrix interactions than calcium transport. Another possibility is that the maintenance of the integrity of normal elastic fibers, extracellular matrix polymers subject to constant mechanical stress, is modulated by (MRP6) ABCC6 in a way that has yet to be explained.

Polymorphic markers in genes encoding known elastic fiber proteins (tropoelastin, lysyl oxidase, fibrillin 1 and 2) were used in a linkage and sib pair analysis, performed with families with both autosomal recessive (AR) and dominant (AD) forms of PXE. No obvious linkage between these markers and the PXE phenotype was found.

TABLE 2

| nt change | Codon # | Effect | Location | Status |
|---|---|---|---|---|
| UNK gene polymorphisms | | | | |
| 33C > T | 11 | Ser to Ser | Exon 1 | Hetero |
| pM5 gene polymorphisms | | | | |
| 2187C > T | 729 | Gly to Gly | Exon 19 | Hetero |
| 3241G > A | 1081 | Glu to Lys | Exon 28 | Hetero |
| MRP-1 gene polymorphisms | | | | |
| 1062T > C | 354 | Asn to Asn | Exon 9 | Hetero |
| 1898G > A | 633 | Arg to Gln | Exon 14 | Hetero |
| 2001C > T | 667 | Ser to Ser | Exon 16 | Hetero |
| 2012G > T | 671 | Gly to Val | Exon 16 | Both |
| 4002G > A | 1334 | Ser to Ser | Exon 28 | Hetero |
| IVS29 − 18delT | — | — | Intron 29 | Hetero |
| (MRP6) ABCC6 gene polymorphisms | | | | |
| 549G > A | 183 | Leu to Leu | Exon 5 | Hetero |
| IVS11 − 41A > G | — | — | Intron 11 | Both |
| 1841T > C | 614 | Val to Ala | Exon 14 | Both |
| 2490C > T | 830 | Ala to Ala | Exon 19 | Both |
| IVS25 + 90G > A | — | — | Intron 25 | Both |
| IVS27 − 46A > G | — | — | Intron 27 | Hetero |
| IVS28 + 49C > T | — | — | Intron 28 | Hetero |
| 3'UTR + 17G > A | — | — | 3'UTR | Hetero |
| (MRP6) ABCC6 gene mutations | | | | |
| IVS21 + 1G > T | — | mRNA splicing | Intron 21 | Compound |
| 3341G > C | 1114 | Arg to Pro | Exon 24 | Homo |
| 3413G > A | 1138 | Arg to Gln | Exon 24 | Compound |
| 3421C > T | 1141 | Arg to X | Exon 24 | Compound + Both |
| 3775delT | 1259 | Fram Shift | Exon 27 | Hetero |
| 3892G > T | 1298 | Val to Phe | Exon 28 | Hetero |
| 3904G > A | 1302 | Gly to Arg | Exon 28 | Homo |
| 3907G > C | 1303 | Ala to Pro | Exon 28 | Hetero |
| 3940C > T | 1314 | Arg toTrp | Exon 28 | Homo |
| 3961G > A | 1321 | Gly to Ile | Exon 28 | Hetero |

Table 2: A summary of all variants identified in the PXE locus in a cohort of 20 unrelated PXE patients. Nucleotide (nt) numbering was derived either from full length published cDNA sequences or from putative cDNA deduced from genomic DNA sequence. Hetero indicates that a variant was identified in a heterozygous state. Homo indicates that a variant was found in a homozygous state. Both, indicates that a variant was seen in both heterozygous and homozygous states. Compound, indicates that a variant was characterized as a compound heterozygote.

Example 3

Mutation Detection in Dominant Pedigrees

The segregation of A BCC6 mutations with the PXE phenotype was studied in three pedigrees with an apparent dominant inheritance. Two of the dominant families (families 1 and 3) presented three generations of individuals, while the remaining pedigree contained only two generations. In all 3 families, a heterozygous mutation, R1141X in exon 24, was found to segregate with the PXE phenotype. In the two-generation family (family 2), an apparent loss of heterozygosity of the R1141X allele was detected in the second generation of affected individuals (II-1 to -3). Several polymorphic variants in the surrounding exons and introns were subsequently analyzed by SSCP. Only one variant, V614A in exon 14, was found to be informative. These results suggested a heterozygous sub-microscopic deletion, which was paternally inherited. This deletion, with a breakpoint between exon 14 and 24, extended beyond exon 24, probably corresponds to a recurrent deletion recently characterized in 4 unrelated families. The latter deletion, confined to a region of the gene between intron 22 and 29 eliminated 16.5 kb of genomic DNA. Therefore, individuals II-1, II-2 and II-3 of family 2 have inherited compound heterozygote mutations, clearly indicating the recessive nature of PXE in this pedigree. Moreover, the phenotype displayed by the mother (Individual I-2) carrying a heterozygous allele R1141X, suggested the partial expression of the phenotype in an obligate carrier. Indeed, individual I-2 showed discreet skin lesions on the neck associated with a positive von Kossa staining of a skin biopsy- (from lesional skin) indicating the presence of calcium salt precipitates typical of PXE. No angioid streaks were reported for this obligate carrier and no cardiovascular examination has been performed yet. In the remaining families (family 1 and 3) no other mutations were found. However, the PXE phenotype of the family members dramatically varied with the generations, clearly suggesting either pseudo-dominance or partial penetrance in obligate carriers. In family 1, the paternal grandmother and the father presented discreet skin lesions on the neck region associated with a positive von Kossa staining of a skin biopsy (no other manifestation were diagnosed), while both children, although very young, had already visible signs of plaques of coalesced papules on the neck and angioids streaks following ocular examination. In family 3, the paternal grandfather was severely affected with lax and redundant skin, disciform scaring of the retina (the vision is severely impaired at this stage) in addition to active gastrointestinal bleeding and intermittent claudication. The father was only diagnosed with a positive von Kossa staining of a skin biopsy while 3 of his children presented with the characteristic PXE skin lesions and angioid streaks.

Accordingly, heterozygote carriers of PXE mutations can develop PXE related phenotypes including sub-clinical manifestations of PXE. According to the invention, the penetrance of PXE lesions associated with a single mutant (MRP6) ABCC6 allele is between about 10 to 20% of all carriers, based on the frequency of described AD PXE cases. Therefore, a pedigree with AR PXE presents sub-clinical manifestations of PXE in 10 to 20% of the obligate carriers. These carriers will be parents of an affected individual and 25% of the unaffected siblings.

Example 4

PXE Heterozygote Frequencies

Upon screening a small sample of the general population (150 normal individuals) as part of a control panel to verify whether nucleotide substitutions found in the (MRP6) ABCC6 gene from PXE patients were indeed mutations, two heterozygote mutations were found in unrelated subjects. The first of these variants was a founder mutation (R1339C) only present in South African Afrikaners while the second substitution is a recurrent nonsense mutation (R1141X). R1141X is one of the four recurrent mutations that have been identified. These mutations are far more likely to be found in the general population than private mutations, which, in principle, can only be found in related individuals. The frequency of heterozygote carriers deduced from the presence of one recurrent mutation in the relatively small sample of the general population is 0.7%. However, four recurrent mutations have thus far been identified. Although each of the recurrent mutations is likely to-have a different frequency, the frequency of carriers can be as high as 2.8%, which is consistent with the commonly accepted prevalence of heterozygote carriers in the general population (0.6 to 2.5%).

Based upon these frequency of heterozygotes and the predicted penetrance of the PXE phenotype in heterozygote carriers (10-20%), heterozygote carriers with PXE symptoms are expected at a frequency of about 0.25% of the general population. In a cohort of about 3000 individuals between 8 and 15 persons presenting cardiovascular, ocular or dermal symptoms would be expected. These numbers provide a basis for a statistical analysis of the correlation between single (MRP6) ABCC6mutations and partial manifestations of PXE. Additional cohorts with clinically defined cardiovascular abnormalities such as the 1200 sib-pairs group from the Family Blood Pressure Program with hypertension, or the NHLBI Framingham study from which an appropriate cohort of 2400 to 4500 individuals is available, can be used to provide additional statistical significance.

Example 5

Creating a Mouse Knockout

Figure 6:
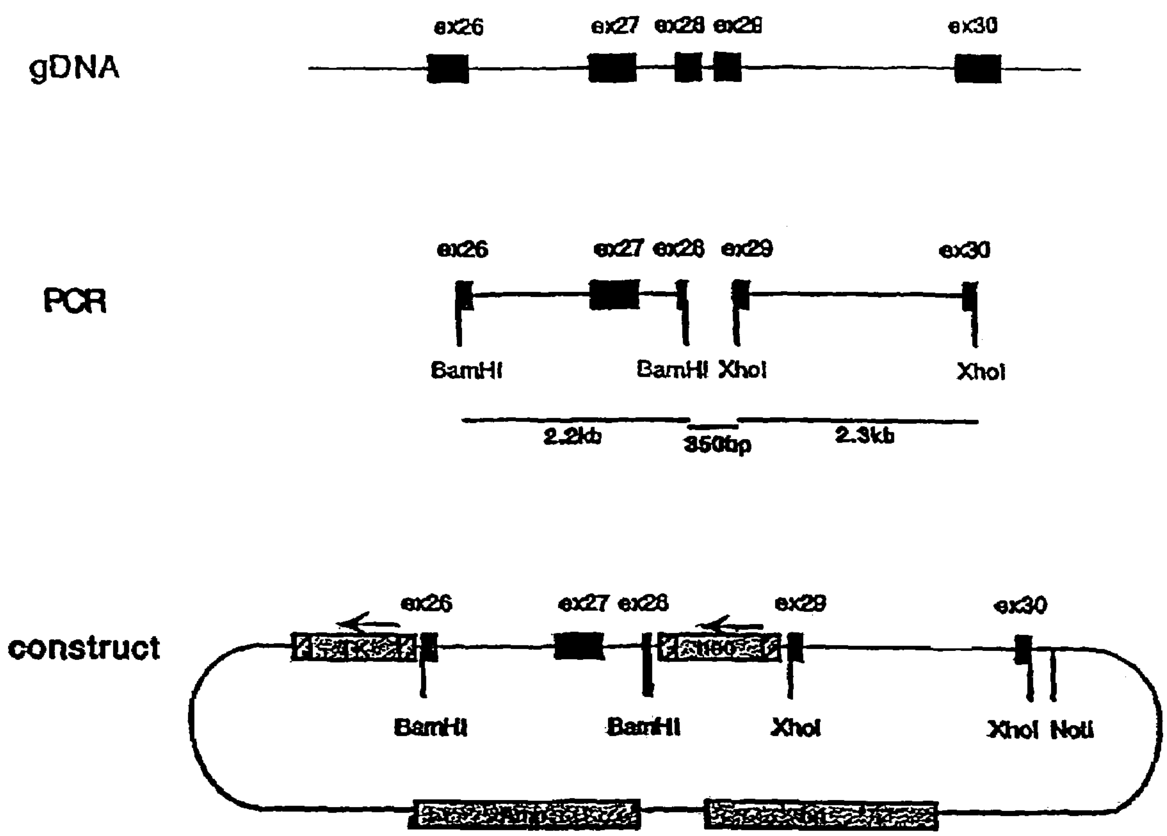
FIG. 6 shows a construct for deleting exon 28 in a mouse.

To create a knock-out mouse for ABCC6 a neomycin resistance cassette is introduced between exons 28 and 29 as shown in FIG. 6. This results in the destruction of the second ATP binding domain whose Walker A domain is encoded by exon 28 and which is essential for the function of any ABC transporter.

Based on the cDNA sequence for the mouse ABCC6 gene (SEQ ID NO: 8), primers with restriction sites were designed to amplify genomic DNA and allow cloning into vector pPNT described in Tybulewicz et al., Cell vol. 65, 1153-1163, 1991. Specifically, a 2.2 kb DNA fragment from exon 26 to exon 28 is cloned into the unique BamHI of pPNT, and a 2.3 kb DNA fragment containing exon 29 to 30 was cloned in the XhoI site of pPNT. In the resulting construct, the neomycin cassette from the vector interrupts the reading frame of ABCC6 in exon 28 after the conserved Lysine in the walker A domain.

This construct will be linearized by NotI digestion and transfected into mouse 129 stem cells. The two resistance cassettes provided by the vector (TK and Neo) will allow screening for homologous recombination and knock out of an ABCC6 locus according to methods known in the art (see, for example, Tybulewicz et al., Cell vol. 65, 1153-1163, 1991).

The deletion construct shown in FIG. 6 will be transfected into *E. coli* and amounts of DNA sufficient for the targeted mutagenesis process will be produced. This construct will be inserted into embryonic cell lines and cells that incorporate the construct will be implanted into surrogate mothers and MRP6 null mice will be obtained according to methods known in the art.

According to the invention, the production of MRP6 null mice with symptoms resembling those of human PXE would provide further proof that mutations at the MRP6 locus are responsible for PXE. However, a more important use for MRP6 null mice, or mice that are carriers of an MRP6 deletion (heterozygotes having an allele with the MRP6 deletion and a wild-type MRP6 allele) is to provide an animal model to study the development and progression of PXE, and to provide an animal model useful in the development of therapeutic approaches (including identifying therapeutic drugs) to treat existing PXE or to prevent or reduce the symptoms of PXE before they develop.

Example 6

Examples of Oligonucleotide Probes and Probes Useful to Detect PXE Associated MRP Mutations Various probes corresponding to regions of specific mutations in ABCC6 are used in standard oligonucleotide hybridization, in oligonucleotide array or nucleic acid chip assays (see www.brownlab.stanford.edu), and in PCR-based techniques for the detection of PXE. Each of the mutations shown below are indicative of a mutation in the ABCC6 gene that leads to PXE.

In a preferred embodiment, the probe shown in SEQ ID NO: 10 is used for the detection of a G to A mutation in Exon 24 of the ABCC6 gene.

CAGTGGTCCAGGGCATTCCGA (SEQ ID NO: 10)

In another embodiment, the probe shown in SEQ ID NO: 11 is used for the detection of a C to T mutation in Exon 24 of the ABCC6 gene.

CAGTGGTCCGGGCATTCTGA (SEQ ID NO: 11)

In yet another embodiment of the invention, the probe in SEQ ID NO: 12 is used for the detection of a G to C mutation in Exon 24 of the ABCC6 gene.

GACCGTTGGAGTCAGCCAGCTACTCG (SEQ ID NO 12).

In another embodiment of the invention, the probe in-SEQ ID NO: 13 is used for the detection of a C to G mutation in Exon 24 of the ABCC6 gene.

GACCCTTGGAGTCAGCCAGCTACTGG (SEQ ID NO: 13)

In another embodiment, the following probes are used for the detection of specific mutations in Exon 26 of the ABCC6 gene.

In a preferred embodiment of the invention, the probe in SEQ ID NO: 14 is used for the detection of a C to T mutation in Exon 26 of the ABCC6 gene.

GGATGTAGGACTATGCCTGGACGCCC (SEQ ID NO: 14)

In a preferred embodiment of the invention, the probe in SEQ ID NO: 15 is used for the detection of a G to C mutation in Exon 26 of the ABCC6 gene.

GGATGCAGGACTATGCCTGCACGCCC (SEQ ID NO: 15)

In yet another preferred embodiment of the invention, specific mutations in Exon 27 of the ABCC6 gene are detected using the probes shown below.

In a preferred embodiment of the invention, the probe in SEQ ID NO: 16 is used for the detection of a C to A substitution in Exon 27 of the ABCC6 gene

TGCAGCTAAGCCCCCCTGGC (SEQ ID NO: 16)

The probe sequence in SEQ ID NO: 17 is used for the detection of a deletion in Exon 27 of the ABCC6 gene.

TGCAGCTCAGCCCCCCGGC (SEQ ID NO: 17)

In yet another embodiment of the invention, the probe in SEQ ID NO: 18 is used for the detection of a G to A mutation in Exon 27 of the ABCC6 gene.

GCTCCAAGCTCCCTGGAGGC (SEQ ID NO: 18)

Mutations in Exon 28 of the ABCC6 gene in patients are detected using the probes shown in SEQ ID NOs. 19, 20, 21, 22, 23, 24 and 25.

In a preferred embodiment of the invention, the probe in SEQ ID. 19 is used for the detection of a C to T mutation in Exon 28 of the ABCC6 gene.

CTGTGGCTCCAGGAGGCAGCTGAGGGTGGG (SEQ ID NO: 19)

In yet another preferred embodiment of the invention,the probe in SEQ ID NO: 20: is used for the detection of a G to A mutation in Exon 28 of the ABCC6 gene.

CTGCAGCTCCAGGAGGCAGCTGAGGGTGGG (SEQ ID NO: 20)

Similarly, in a preferred embodiment of the invention, the probe in SEQ ID NO: 21 is used for the detection of a G to A mutation in a different region of Exon 28 of the ABCC6 gene.

CTGCGGCTCCAGGAGGCAGCTGAGAGTGGG (SEQ ID NO: 21)

Probes in SEQ ID NOs. 22, 23, 24 and 25 are used for the detection of additional specific mutations in Exon 28 of the ABCC6 gene.

GTGGGCATCTTTGGCAGGACCGGGG (SEQ ID NO: 22)

GTGGGCATCGTTGGCAGGACTGGGG (SEQ ID NO: 23)

GTGGGCATCTTTGGCAGGACCAGGG (SEQ ID NO: 24)

GTGGGCATCTTTGGCAGGACCGGGC (SEQ ID NO: 25)

EQUIVALENTS

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes which come within the meaning and range of equivalency of the claims are intended to be embraced therein.

INCORPORATION BY REFERENCE

Each of the patent documents and scientific publications disclosed herein is incorporated by reference into this application in its entirety.

What is claimed is:

1. A method for identifying a patient as having an increased risk of having children with PXE, the method comprising:

a) interrogating an MRP6 nucleic acid in a patient sample for the presence of an MRP6 allele known to be a co-segregator with a PXE phenotype; and b) identifying said patient as having an increased risk of having children with PXE if the allele from step a) is detected in said-MRP6 nucleic acid.

2. A method for identifying a patient as having an increased risk of developing a PXE associated symptom, the method comprising:

a) interrogating an MRP6 nucleic acid in a patient sample for the presence of an MRP6 allele known to be a co-segregator with a PXE phenotype; and b) identifying said patient as having an increased risk of developing a PXE associated symptom if the allele from step a) is detected in said MRP6 nucleic acid.

3. The method according to claim 2, wherein said PXE associated symptom is cardiovascular disease.

4. The method according to claim 2, wherein said PXE associated symptom is macular degeneration.

5. A method for testing a patient for the presence of a PXE mutation, the method comprising the steps of:

a) interrogating a patient sample for a mutation shown to be associated with PXE, the mutation being in the MRP6 gene, and the mutation is selected from the group consisting of:

i) at codon 1114, nucleotide 3341G>C;

ii) at codon 1138, nucleotide 3413G>A;

iii) at codon 1141, nucleotide 3421C>T;

iv) at codon 1259, nucleotide 3775delT;

v) at codon 1298, nucleotide 3892G>T;

vi) at codon 1302, nucleotide 3904G>A;

vii) at codon 1303, nucleotide 3907G>C;

viii) at codon 1314, nucleotide 3940C>T; and ix) at codon 1321, nucleotide 3961G>A; and b) identifying the patient as having a PXE mutation if the mutation from step a) is detected in the MRP6 gene.

6. A method for detecting a patient as having an increased risk of developing PXE, the method comprising:

a) interrogating an MRP6 nucleic acid in a patient sample;

b) determining an abnormal presence or absence of at least one nucleic acid fragment or sequence in the patient's MRP6 nucleic acid compared to a normal control; and c) identifying said patient as having an increased risk of developing PXE based on the determination in step b).

7. A method for screening a patient for the presence of a MRP6 gene mutation, the method comprising:

a) interrogating an MRP6 nucleic acid in a patient sample to determine an MRP6 nucleic acid sequence; and b) identifying said patient as having a MRP6 gene mutation by comparing the MRP6 nucleic acid sequence from step a) to a normal MRP6 nucleic acid sequence.

* * * * *

SEQUENCE LISTING

```
<160> NUMBER OF SEQ ID NOS: 27

<210> SEQ ID NO 1
<211> LENGTH: 107820
<212> TYPE: DNA
<213> ORGANISM: Homo sapiens
<220> FEATURE:
<221> NAME/KEY: misc_feature
<223> OTHER INFORMATION: "n" can be an A or a T or a G or a C

<400> SEQUENCE: 1

aagcttgcag aaggtggttg gcttttgttc tgaatctaac aagacttatc gggaggctct     60

tggtgcctgg cactggctga atgcccaggt tgggggaggc agagcagatg aagcatctgc    120

ccgcgagggt gggtggagct gcttgtgaaa cgtatcatcg tagcccggga gctgggacac    180

tgaagcccgg agaaggtgct catggaggat gggaagggct tcccgaggaa gtgacatctg    240

tgctcccatc tgctgggtga tgaggaatgg cctggacggg atgggcatgg tgggtggagg    300

caggcggcct gtgtgcaggg aaggaagggg agagttacag gatgagatga gttgagggaa    360

gaagcatggt tggcaactct aacagcgctg ggaggccatc ggaggggggt gacgagattg    420

accctatcct catgggcatc tcagctgggc tgagtgtgct ggaaccggcc attgcatgga    480

cacagtcact cctgagggga tgtgatcaac aggcggaatt ctgtcactta atgataacaa    540

tagtcaccag ctaactgaat gcttactgtt aggtcaaact atatgaaact gctaatactt    600

atttcttatc tacagaaaca gctatttcct gtggttcaac ctagtattac caggcactgt    660

gcttagtgac atcatgcata tctatatgat ttatgaaata atgtgtccac gcaaatacac    720

atcacatgta agactgtaac tcttacatgt caccctcaca atgaccccgt gaagcaagct    780

ttgttttgtt tcgtttgttt tcttaataat attttatttt tgtagagatg gcattttgcc    840

atgtgcctgg gctggtctca gactcctggc ctcaagtgat ctcccgcctc tgcctcctga    900
```

-continued

```
agtgcgggta ttacaagcat gagccacccc acctggccga gcaagccttg ttgttcccat    960
tttacagata aggaaactga ggcttagaga agtaaagtgt tagtcgtgtt tatattgcca   1020
gtcagtagtt gagtcaggat ttgaactgag gtctcgttga cctcaaagcc tatgctgaaa   1080
accacactgc tggttccaga aaaccctaga ggtgaaaggc ttcagagagg cagtacaggg   1140
tagaggttag cactttgcag cccagatggc ctgggtttga atcccagttc tgccccttgc   1200
tagccatgtg accttgggga ggagattaac tagcttcttt gtgccttagt ctacccatca   1260
catataggaa tgagcacctc aggttttttg tgaggattga atgaactgat gtttgtaaaa   1320
ctgcttagaa cgatgcctgg ggctgtgggc tttgtataag cgtgagctat tattgtcact   1380
gtccttgtca ttggtggtgc tattcctgtg gttcaccagg tgagtgggca cccctgtgag   1440
ggcagcccgg ctctaacatt ttgcctcctg gaggtatcgg ttacgtctag atgttctcca   1500
gcacagccct gccctgggag gatggcagga gggaaccttc atcaactccc cgcgtctgtt   1560
ctctacccca gaggttctac gtggcttcct cccggcagct gaagcgcctc gagtcggtca   1620
gccgctcccc ggtctattcc catttcaacg agaccttgct gggggtcagc gtcattcgag   1680
ccttcgagga gcaggagcgc ttcatccacc agagtgacct gaaggtggac gagaaccaga   1740
aggcctatta ccccagcatc gtggccaaca ggtgggcatg gtgggcctgc aggagcgggt   1800
ggaggaggcc gccttagcac cttgtctctt tgcctcgatc ttttcctcgc accttgagct   1860
gggtataaag ccaaaccccg gccttgcaga aaggatggag aggcttgatg agcgcggagg   1920
acagatgaat cattaagagc agacagcggc actgtagaca tgcagtgccc gcggcattta   1980
agtgcaggga cacagctctt ctggagtcag aaagccctgc aagtgcttcc cgttaactgt   2040
catcctagtg atgcaagact gccagcgacc gactctgcta ttgagtatct tcataccgct   2100
gttcccgtct gggggtgatc atgcacccct gggtgatgtg tgtcagaagc aatttactaa   2160
tactaagcta aaccatatga gattgtcatc ttgtgggcca gatgtcatgg ctcacgcctg   2220
taatcccagt actttgggag gctgaggcag gaggatccat tagattccag gccagcctgg   2280
gcaacatagc aagaccccca tctctcttaa aaaaaaaaaa aaaaaaaaaa agtagcccat   2340
catggtggtg tgtgcctgta gtcctagctt ctcgagaggc tgaggctgga ggatcgtttc   2400
agcccaggag ttcaaagttg cattgagcta tgattacacc actgcactcc agcctgggtg   2460
acagagtgag accctgtctc tggaaaaaca aaaaaaggag atgggggtgg gagattgaca   2520
tcttgtggat cacagataat agcatcaatc caaaagaggc agaagtttgc taattatttg   2580
ctgaatttag agaagtgtcc ctctcaccca tttgcatcct tatagacttt tctgaaaaag   2640
tgacagcacc ccagaggtgt cccataacca ttagcccgtc ttacacactc taatcccata   2700
gcgtaagtct gggtgggcta accctgaatg attacagacc ttgacttccc ttcagaattt   2760
ttagggagtt tgtcacaatc tggctgtgtc tgtcggagta gtgaggatca gtcacttggt   2820
tcataagggc tgcaatggag aaaagatcaa caccccatct tcctagaatg ctttatattt   2880
tagaacatta aaataatagt tctagtgcta tatgatatca tacgaagcct agctttaaac   2940
aaataagatg gccaggcgcg gtggctcaca tctgtaatcc cagcactttg ggatgccaaa   3000
gtgggtggat cacctgaggt caggagttca agaccagcct ggtcaacatg gcaaaatccc   3060
atctatatta aaaatacaaa aaaattagcc gggcatgatg gtgggtgcct gtacttggga   3120
ggctgaggca ggagaatcac ttgaacccaa gaggcagagg ttgcagtgag ccaagaccgc   3180
accattgcac tccagcctgg gcaacgagag cgaaactcta tctgaagaaa taatagaaga   3240
gaagagaaga ataaaataaa aagtaaaata aaatagttct gatggtacat gataccatac   3300
```

-continued

```
taaacctagc tttaaacaaa taagatgacc aggcacattg gttgacacct gtaatctcag   3360
cactttgggt ggccaaggca ggcgggtcac ttgagcccag cagttcgaga ccagcctggg   3420
cactctaggg agaccctgtc tctaaaaaca aaacaaaaaa ccaaaaattt gccaggtgtg   3480
gtggcatggg cctgtagtcg cagctactca ggctgaggca ggaggatcac tggaacttgg   3540
aaggttgagg cggcagtgag ctgtgatcat gtcatccaca ctccagcctg gatggcagag   3600
taagacccca tctcaaaaaa acaaaatgac agaaaacatg atttctgttt ctattttaaa   3660
gggtaaaata gtatatttta acactttgaa atgaagagtc tgggcttggg aacgttacaa   3720
tgatgtttac tcgtactagt tacgcactcc cctcccagat ctgtctcgta acaagagact   3780
gttattttct acttgttttt agccaaaagg ccgagaaacg atggttattt taaatcccta   3840
gtgtctctta cagttgatgt cttcttagta tttaggaatt tccaggacat ctttttgttg   3900
ttgttaatgc actgtgtgtg tgtgtgtgtg tgtgtgtgta tgtgtgtgtg tgattatagg   3960
agtgacccac tacgcccggc tgtgtgtgtg tgtgtgtgtg tgtgtgtggg tgtgtgtgta   4020
tgtgtgtgtg tgtgattata ggagtgaccc actacgcccg gcctatgtgt atgtatttta   4080
aaggcttcaa tgagaaaaaa gttggttctt aaaaaggcaa gcttcagatt ccagggaaga   4140
ttgcctctgg agagctctgt tttaatccat gggtttgcca gattaatgag gatttactgg   4200
cctcgtgcct tcggccctcc ctaccctgcg cccattgtgc atgttttgaa aaagcagtgc   4260
caggaaggac tctctctgga attactgcgg agttacttga gttagcaaag aatccccttc   4320
ctcccccaag agctgtaagc caagtctctg tagagctgac tccatgcctg tttgtctgcc   4380
tgtgtgtctt ggcgcaggtg gctggccgtg cggctggagt gtgtgggcaa ctgcatcgtt   4440
ctgtttgctg ccctgtttgc ggtgatctcc aggcacagcc tcagtgctgg cttggtgggc   4500
ctctcagtgt cttactcatt gcaggtaaga ggggatgctc ttggctggat tattaaagtc   4560
tgttaatggg ggagccagtt gtccttggct ttggattcca gctccaacag gaatggggga   4620
gaggaacttg agaggtacgg agtttgagga gcaggtacag tgccacagtg cctggtgacc   4680
aactagagca ggagacggat ttgacatgtg gccaggattt tccccatcag tcacacagat   4740
tccttagtgg cccaagagga tacttccagg tacgagggga atgcttttaa agctatgaat   4800
ttccctctaa gaactgcttt agctgcatct cacaaatgat gatacattgt gttttcatat   4860
tgtcacctgg ctaaaaatat tttccagttt cttattatgt ggcccatgag ttattttgga   4920
aatgtgtgtg cttaggagat ggcaatgtgg caggcctggg tgatggctat acctggggtt   4980
gctaatttcg gtacctttct tacctgaatg tttcataact cataaccttt tatttttatt   5040
tatttatttt ttttggagac ggaatctcac tctgtcaccc aggctggaat gcagtggtgg   5100
gatctcggct cactgcaacc tctgcctcct gggttcaagt gattcttctg cctcagcctc   5160
ccaaatagct gggtttacag gtgtgcgtca ccatgcctgg ctaattttta tatttttagt   5220
agtgactgat ggggtttcgc cacatcggcc aggctggtct caaacccctg acctcaggtg   5280
atctgaccgc ctcagcctcc cataattcat acttgttgaa aataatttgt ttcctattat   5340
ctcagtggaa aaaaaaaaaa aaagaaaaag gaaagtcaag tacgcccgct tactctagaa   5400
atgccacgtg actcttccac tcacaggtca ccacgtactt gaactggctg gttcggatgt   5460
catctgaaat ggaaaccaac atcgtggccg tggagaggct caaggagtat tcagagactg   5520
agaaggaggt aggcaagggc ccctggctgg acctcttggt ctttggtgta gctttacccc   5580
aaggagatct ctggacccta tcctgtgcac ctctgcctct gagctggata cctcaccagg   5640
```

-continued

```
tagaagtgca tcttaacgct tgtccagtct tttgcagca cttatttaga gcccggtttt   5700
agggtgaaaa tagtttaccg gctttaccca agatctgggg tatccatata cgagactgtg   5760
ggatgctgtc agggcattca gaaggtattc acattgtgaa gaagtttccc cctctatttc   5820
tctttcataa cttctgatgg tatcacagag aaagtcttag tctggggcta gcaggtcttt   5880
aacaccttag caattgagat gatctccctt caacagacag ataaacagca gccctcacac   5940
ttggagtctt caacaggacg gcttctgtct atcagaaata accttctgtt atttgttatg   6000
aatttggttt ttttgtgtgt gtgatggagt ctcactgtca cccaggctgg agtgcagtgg   6060
cacaatctcg gctcactgca acctcctcct cccaggttca agtaattctc ctgcctcagc   6120
ctcccaaata gttgggatta caggtgcctg tcatcatgcc tggctaattt ttgtattttt   6180
agtagagatg gggtttcac taagttggcc agtctggtct caaactcttg acctcaggtg   6240
atccgcctgc ctcagcctcc caaagtgctg ggattacagg cgtgagccac tgcgcctggc   6300
ctgttatgta tttgtatagg ggactcctgt tacggaaaat aatactactt ttcctttttgt   6360
gattgtaata aattttcctc ttaagtaagt tgagaaatta agtctaagtg acttgattaa   6420
gcatattaaa acaacaagag aatgagtaca tgcatactac acgaatgatg tagctgggaa   6480
ctgaccaaag tttgggaaac cctgcagtta ttgaacccca gtccccttttt tatagatgga   6540
gaaaaaggga acctggggag ggacaacagc tgatccaagg tcccacgtgg cttggtagaa   6600
cagctgggac taggacctgt gcctccagtc tttgatgttg cgttgccctt aataactgcc   6660
ttcttaggcc ctgaacagca gcacaagtag gaacagcagt gataatagat aatcacaata   6720
atgcctggcg acaccccccac cctacattaa tgataacagg gacacacata gtgccttgta   6780
gaatgtcagg cccagactta aacgtttaat atagagtaat gcactcagtc tttaccccgc   6840
tctatgactg atttttgaga cacggtctca ctcttgcccg ggttggagtg tagtgcgatc   6900
tcattcgctg cctcccaggc tcaagtgatt ctcctacctc tgcctcctga gtgtctggga   6960
ccacgggcat atgccatcac accggactga tttttgtatt tttagtagag acgggatttt   7020
gcccagactc atcttgatct cctgagctct agtgatctgc ctgccttggc ctcccaaagt   7080
gctgggatta caagcgggag ccaccatgcc cagcccagcc ctataattta gatgctacta   7140
ttaccccccat tttacaggtg aggaaactga gacaaaaagc tgaagttact tgcccaagat   7200
cacatggctg gtaaatggca gacctaggcg ttgagcctgt gcctcctcag agaccctatc   7260
cagtgccatg ggagtcatgc tacccggcct cctgaggaga gatgcccctt gggagtgaga   7320
ccaaggcctc tgtaaggtct gtcctcctga ggaattcaca gaggtgacct cggcccactc   7380
ctttaacatt ctgactgggt gaaccaggtc ccatgtcacg ggtgagcatt gtaagaatgg   7440
cgtgagtgcc cccgtgagga accaagggtg tattacaccg gcggcttcca acttgacact   7500
gaatttaatt cacttacaag gtatttcatt aggttttttt tttttttttt tttttagatg   7560
gaatttggct ttttttttgc ccaggctgga atgcagtggc acgatctcag ctcactgcaa   7620
cctccacctc ctgggttcaa gtgattctcc tgcctcagcc tcccaattag ctgggattac   7680
aagtacccac caccccgccc agctaactta tttcattagt ttttataata gcctcattga   7740
catgtgaatt tcacatgcca tggaattcac ccagttaaag cgttcagtta gattgaattc   7800
agtttttttt tgtttgtttg agacttaagt ctcgctccag cctggagtgc agtggcatga   7860
tctcagctca ctgcaacctc cttctcctgg gttcaagcga ttcccagcct cctgagtagc   7920
tgggattaca ggcgattttt gtatttttag tagagaaggg atttcaccat gttggcccgg   7980
ctggtctcga actcctgacc tcgtgatcca cccgcctcag cctcccaaag tgctgggatc   8040
```

-continued

```
acaggtgtga gccaccacac ccggcctgag ttcagttttt aaaagcattt tacttttgac   8100
tgacttttat atttttagaa ggatcgtgtt tgacaaaccc aagagaaagt aattgtcctc   8160
attagtccta ccactattct gtatttgcat gtatttttat atatagatag aaagttccac   8220
atacttctct ccattccgct cactgtgttg ttatagcatc tccccttcaa ttatgtacat   8280
aaattataaa atagagatac acttgttgtt ttaaaaaaga aaaaatcaat acagggctgg   8340
acacagtggc ccacgcctgc aatcccagca ctttgagagg ccaaggtggg tggatcactt   8400
gaagccagga gttcgagacc agcctggcca acggtgaatc ccgtctctac taaaaataca   8460
aaaattagtt ggcatggtgg caggtgccta taattccagc tacttgggag gctgaggtgg   8520
gaggatcgct ggaacccggg aggtggaggt tgcagtgagc tgaagaaaca tcactgcact   8580
ccagcctggg tgacagagtg agactctgtc tcgaaaaaca aaaaaacaaa gaagtttatg   8640
gtggagaaag acagtttgtt cctgttcgcc ccgttcctct cctctccaga gagaggcccc   8700
attagcattc gggtgaattt cccccaaaac tttcccgtgt ggattcccac ataccccaac   8760
acttttgttt gcttgtttct ttttctttta acgtaagtgg aatctacctg ttatcctgtg   8820
aaacctttte tttaaccatg aggcaccttt gcatctgtgt atagtaacag tcactgcctc   8880
taagggctgc tgtgaggctc agatgagatc atgggtctca agtgctgagc agagcaactt   8940
gccttagttg cattgtaagc gctcaataat aacatttatt ttttggccag gcgcggtggc   9000
tcacgcctgt aatcccagca ctttgggagg ccaaggcaga tggatcactt gagcccagga   9060
gtttgagacg atcctgggca acatggtgag acatcgtctc tacaaaacaa aaaataatac   9120
tttttgttgt tggcggtggt ggtggggttt tttttgtttt tttttttttt gagacagagg   9180
agtcttgctg tgtcacccag actggagtgt agtggtttta tcttggctca ctgcaacctc   9240
tgcctcccag attctagtga tcgtcgtgtc tcaacctccc aagtagctga gattacaggc   9300
tcccaccatc aggcccagct aatttttgta tttttagtag agccagggtt tcaccatgtt   9360
ggtcaggctg gtctcaaact cctgacctca agtgttctgc ccacctcggc ctccctaagt   9420
gctgggatta caggtgtgag ccactgcgcc ggcaacgctg tgattttata gcacgtccac   9480
aaaagggctg catgtcttgc ctaaaagttg cccggcgttt tcttgttatg tgccgtctgc   9540
agtgcccctg agcttggcca tgtgctctgc agcctggttc agcacctgtg tgtgccctgg   9600
acggggaggt gcattccccg aggctaaaac cagtgaacct ggcccaggcc atatccagct   9660
gtgggcctca ggaaatgctg aactgaacta cttttcaaaa ggagggttgt gtgtccctgg   9720
gcaagttacc gcccctctct gtgtctcagt ctccttgtgt gtaaactggg gataatgaaa   9780
ggaccctccc acatggggtt gctgtgagga ttggatgaga cactgcgata cagatgctgc   9840
ttttatcctt gccttcctgc cggggtgggc agccagggta actcactttt attgtcgtgt   9900
ctgtccagag aagaccactc atttcattga ctccatttat aaatatttat ttaaattttt   9960
ttttatcaaa aagtaagttt tattggcatc taaaaacaaa attcacccaa cactgaaaca  10020
tacttcaata tttatgttat tgttttcttg tttctttttt actcactgca gtgtgaggaa  10080
caaatcacat ttactttgga gaaacagaga ccatagtgta gattttacaa aatcactttt  10140
taaactctct gtattgcgct cctcaaatac ctagagccag tctgtgcata acatggcaca  10200
ctgttgtcta aaccgtaaaa ttttgcatca gcctaaagat atggataaga tatacctcca  10260
cttgctcttt tgaaatacat ctattacctt atccagccta atgatagtta cctaaaaaat  10320
tctttgttcc gtaggaagtc tctgacaagc tgttattcat ttccttgacg ttaaaagaat  10380
```

-continued

```
ctgggggcaa catttatatt ttatcagaaa aactttttaa aagtttacct atcatgttca  10440
tattgagaac aatgtctgtg gcgggcatgg tggctcacgc ctgtaatccc agcactttgg  10500
gaggtagagg tgggcggatc atgaggtcag gagttagaga ccagcctggc caacatggtg  10560
aaaccacatc tctactaaaa atacaaaaat tagctgggtg tggtggcggg tgtctgtaat  10620
cccagctact caggaggctg aggcaggaga gtcgcttgaa cctgggaggc aggggttgca  10680
gtgagctgag atcatgccat tgcactccag cctgggcgac agagtgagac tccgtctcaa  10740
aaaaaaaaga acaatgtcta tacaaatcag ttgtacaatt attttaaaag aatggtgagc  10800
atgaacgtca cgttaattct ggcagacaaa aatgaacaac tatggtccat tgagccatta  10860
tctgttacac agagatgaca gctttacaga aggtatctct gacctactga gggatgatca  10920
tgtcctctca gtttctgtgc cttctaccac tagttcactt tctatatcag cagctgtgtc  10980
actcttcttg tttatgttca taaatgtgtg ttgaacacct actatgtgct ctgagccctg  11040
ggatacagca gtgaacaatt agagcctgtc ctcattgagt ggatggtgca gtgggtgtgg  11100
gagacagaat acactcaagc atgcgagccc caagagggct ggggacaggc agtgccctga  11160
aggagaaggc agtgcgggag gggacagagg gacacaggc tgagagggtg ctctgtatcg  11220
accagagatc cacaggatgc aagggggtca tttggggaat aacattccag gaagggcaac  11280
cccccagtgc tgaggcctgg gaggccacct tgggcagcag agtgagtgag aggggaggtc  11340
aggggagtca cagctttacc agatggactg gaaattcctt actctctccc ttcactgcga  11400
tcgaaggcgc cctggcaaat ccaggagaca gctccgccca gcagctggcc ccaggtgggc  11460
cgagtggaat tccggaacta ctgcctgcgc taccgagagg acctggactt cgttctcagg  11520
cacatcaatg tcacgatcaa tgggggagaa aaggtgggta cacatcgccc cattccctca  11580
cccattccca gtcgggcaca gggtgccatc gggcaggtga acctagctgc agcgtctccc  11640
cagtcactca cggctccaca cctttgcttg aatggctttt tggggggctg ggagtggact  11700
gtggcagtaa aagctgttca gagcgcatac aacttgcaga agtgaaggct tttaggtgaa  11760
ctgacagcct gaagaccaaa tgagccccac agatttgttt tggaagattt tttgttgttg  11820
ttgttgagag agggtcttgc tctgttaccc aggctagagt gcagtggtgt gatctcagcc  11880
cactgcagcg gcagcctccc aagtgggggg actacacatg gttgggagtg caggtgtgtg  11940
ccactgcacc tggccatttt ttgtattttt tgtagagatg gggtcctac tatgttgtcc  12000
aggctgatct ggaactcttg agctcaaccg gtctgcccgc ctcagcttcc caaagtgctg  12060
ggattacagg aatcagccac cattcctggc ccctggaaga agttcttttt ttgttttttg  12120
gttggttgtt tttttttttt tttttttttt ttttttgaga tggagtctta ctctgttgcc  12180
aaggccagag tgcaggggcc cgatctcagc tcactgcaac ttctgcctcc tgggttcaag  12240
tgattctcct gccttagcct cccgagtagc tgggactaca ggcatgcgcc accatgccta  12300
gctaattttt gtgttattag tagagatggg gttttgccat gttggccagg gtggtcttga  12360
actcctgacc tcaactgatc cacccgcctc agcctcccca agtgctggga ttacaggtgt  12420
gagccactgc acctggcctg gaagaaattt gaataagttg caaatactga aaaatctgga  12480
agacttaata taaaaattta ttttctgctt tttttggaag atcagaacat ctggcaacat  12540
caggtcaatc ctcccccgcc tggctctttc tagtcaacct gtgagcctcc tggttcaccc  12600
cagtccctcc ctgtcccatt cattgcctag ttggcccctc caaaacatta gaatttgtga  12660
tctctagaat aaggtgtcac catcccttct agggggatgg ctcaagggaa gtgagaaatt  12720
gtcagaattt tggaaccttc tcttggttcc gagctgttct tggaagaggt tccttgacct  12780
```

-continued

```
gagtgatacc cttagacttt cctctggaat tggtctgaca gtcttcctgg ccatttgctg  12840
ggggacaagg ctgctttcac ctctgaacat atggacttat tgaactgttc ctacgtacct  12900
cccacaaagc tcagaacatt ctgttcccag cagataattt ctctctgagt tacagagaag  12960
agcagagtgg gtgatgttct tgctgtcttt ttttgttttt gtttttgttt ttgtttttgt  13020
ttttgttttg ttttgttttg ttttgagaca gcctctcact ctgtcaccca ggctggagtc  13080
cagtggtgct atttcggctc actgcaacct ccgtcccctg ggttcaagtg attctcctgc  13140
ctccgtctcc cgagtatctg ggactacagg tgcatgccac cacgcccagc taatttttgt  13200
agttttagta gagatggggt tttaccatgt tggccaggct ggtctcgaac tcctgacctt  13260
ctctgatcca ccttcctcgg cctcccaaag tgctggaact acaggcatga gccaccgtgc  13320
cccagccctt gttgagtctt tatggcttat ctcacgtcat gagaattttt gcacgcatgc  13380
tgctctgtga cacccctgta ggagggaaga aggagcccac ttctcaagag ccaggcagga  13440
aggggagaac tggaggtcag gaacatcatc ctttggccat tagctagaga acctagttcc  13500
ttcaagagag gatgcatgga gaccaggtca tagcaaaggg ccggaagatc tgcctgaatc  13560
tttcagatat ttcaacaact catgatggga aactcaccat caaaggtgtg aaaaacagtg  13620
gggaaatgag gaaatgcctg attattactt aatagtttct tgagtctaaa caaatagggc  13680
tttgttggaa attccttctg cctcttctgt atctcttttg aggtctctag taacttataa  13740
aaagccgagt cattcctttt gggagcctgg caaagggaag agagtccttc ttgaccttcg  13800
gccgaaacac ccttaaagga gtgtctctgg gcagcgcgca agggagaggg ctgtcgagtt  13860
gggttgacca gatgactgat gcctgaggtg gggccgagat gagggcactt tggggcaggg  13920
acaagtccgg atgccagcat tcccaccaca cctgggccct tctgtcctgc aggtcggcat  13980
cgtggggcgg acgggagctg ggaagtcgtc cctgaccctg ggcttatttc ggatcaacga  14040
gtctgccgaa ggagagatca tcatcgatgg catcaacatc gccaagatcg gcctgcacga  14100
cctccgcttc aagatcacca tcatccccca ggtggggtct gggtgtggcc caggggggtga  14160
gccagagctg gcaagcccta tgattgcact gacagtggtg tatgtatatt tttggggcaa  14220
acatacattt ggccctactt catcgttctt tttttttttt tttttttttt tcctgaaaca  14280
gggtctcgct ctgttgccca gagtggagtg cgctggcgca atctcagctc actgcaacct  14340
ccgtctccca ggctcaagcg attctcccac cccagcctcc tgagtagctg ggactacagg  14400
cacatgccac cacacccagc taaatttgtt ttgtactttt ttgtggagat ggggttccac  14460
tgtgttgccc aggctgccct tgaactcctg ggctcaagca atccacccac cttggcctcc  14520
aaaagtgctg ggattacagg catgaggcac cgtggctggc cttcattgtt tttattgaag  14580
ttaggctgtg ctgctgcttc cctgaatttc ctcttagtat atgattaaca acgtgggaat  14640
taactgacta tcagtcccga cttcctgtcc ccgggagggg tagtttcaga gcatctagaa  14700
aaatccaaaa agacaccgtc ttctctctct gctgccagag tcagactgag catctctaac  14760
ccttccaaga gctagacaag aaataagact ttttaatttt cgattcacgg ggtgcacctg  14820
caggcttgtt acgtgggtat attgtgtgat gctgatgctt cggcttctat ggatctcatc  14880
acccaactat tgaacagagt acccgagaga gagtagtttc tcaaccatta ccctcctcca  14940
tctgtcccca cttatggagg ctccagtgtt tatcatttcc atctttacaa ccatgagtac  15000
gcagagttta gctccctctt acaagtgaga acacacagta tttggtgaga aataaggatt  15060
ttctttttct ttctcttttc tttttttct ttttttaact gagacggagt ctcactctgt  15120
```

-continued

```
cacccagtgc agtggcacga tctcagctta ctgcaacctg cacctcctgg gttcaagcga  15180
ttcttctgcc tcagcttccc aagtagctgg gattataggc acgcaccacc atgcgtggct  15240
agtttttgta tttttagtag aaacggggtt tcaccatgtt acccaggctg gtctcaaact  15300
cctgacctcg agtgatctgc ctgcctcggc ctcccatagt gctgggatta caggggtgag  15360
ccaacatgct tggctgaaat aaggatttc tagaccaatc cccgcaggtg gattccttaa  15420
tatgttgcct tttagtgtaa tcttccctaa agtgtcttag aagattctct tctgtggttg  15480
gatgacggga gaatccacgg gactttactg ttaggaatca cctgtgctgc gtctcatttc  15540
tggaggttct caacccactt gcatattgaa ggctccagga agttgtatgg aaaggaaatc  15600
tgttgtattc tgccaaactc agactttcca gactttttt tttttccat tattaaggca  15660
atttttttt tggagataga gtcttgctct ggagtgcagt ggcacaatct tggctcactg  15720
caacttccgt ctcccgggtt caagtgattc tcctgcctca gtctcctgag tagctgggac  15780
tacaggtatg caccaccatg cccagctaat ttttgtattt ttactagaga cagggtgttg  15840
ccatgttggc caggctggtc tcgaactcct gaccttaagt gatccactcg cctcggcctg  15900
ccaaagtgct gggattacag gcgtgaacca ccgtacctgg ccttttctc cattattaac  15960
atctccagaa atagtgattc caaggagctc tgataccca ccttcaacag tcctggccag  16020
aagtccttag gtcgcctcca tccatgtcag catgacacag gtgtcacatg ccgtccactc  16080
tcttctctct gaacaggacc ctgttttgtt ttcgggttcc ctccgaatga acctggaccc  16140
attcagccag tactcggatg aagaagtctg gacgtccctg gagctggccc acctgaagga  16200
cttcgtgtca gcccttcctg acaagctaga ccatgaatgt gcagaaggcg gggagaacct  16260
caggtaggcg ggggtgaaca aggagacacc gggtaaggtg tcctaggcgc catctcggta  16320
ggggtgtttg aagattctgt ccagatctgt gtcacctgga tttgagtccc agatgaccat  16380
ttgtcccttc acctcttgga gcctcagttt ctgtatctgt aaaacgggtc tcaatccagg  16440
ctctttgtac catgaggtag aataaccagg atgaccagta catttccttt tatacacacc  16500
agctccattc agttgatagt ggctgtcagt tgttaagcta tggaaagtct tctgtaccag  16560
ttggtcacta gcactgctct gagcccccag gtccccatgc actaccccag ctgtcttggt  16620
ctctaccagg atcctggagc tctgtccatg acccagcaac taaagcatta atgcctggca  16680
caccagcgga acctctgggg tcctgctttg gtggtgtttg ttagtgcctg gttctggttc  16740
tgttatccgt ctccatgaca accaaccata aagcctcagg catgttcaac cataaagcaa  16800
cgatcattgc tgccatacga gggcagtcag ccaggtggct ctgctgatct cggctgggct  16860
cacatgcatg tctgggagtc agctggctgt tggctgatct cggggtcagc tggcttttgg  16920
cctcaggtgg ggcaagaagg gtatgttccg tgcatccctc attctccagc agaccagctt  16980
gggcatgttg tcatggcgat ggcaggggca caagagcgtg caagccccta ttgcatctaa  17040
cagtattctt ttggctgtcc ttacttttgc tggtgtccca ttggccaaag caaggaacat  17100
gtctgattcc agagccacct ctcatggccc cacagttgga taagggatgc atgggtatga  17160
ggcctttttt tttttttt ttttttttt tgagacggag ggtctcactc tatcacccag  17220
gctggagtgc agtggcgcaa tctcatctgc aacctccgcc cccaggctca agcaattgtt  17280
ctgcctctgc ctcctaagta gctgggatga caggtgcctg tcaccatgcc cagttaaatt  17340
ttgcattttt agtagagatg gggtatcacc acattgtcca ggctagtctc aaactcctgg  17400
cctcaagcga tccacccgcc ttagcctcac aaggtgctgg gatactaggt gtgagccact  17460
gtgcccggct cttatttttt ttttatttta tttttttaa gagacagtgt ctcactctgt  17520
```

-continued

```
tgcctaggct ggagtacagt ggattgatct cggactctta actcctggac tcaagcaatc  17580
ctgcctcagc ctcccagtaa ctgggactac aagagcatgc caccacaccc agctaatttg  17640
tttatttttg tttttggaga gatgggggtc ttgctttttt gcccaggctg gtctcaaatt  17700
cctggcttca agctatcctc ccacctcagc ctcccaaagt gctcagattg taggtgtgag  17760
ctgctgtttt gagaatgatt ctgaacctgc atcttgctga ataggagatg tgctctgatt  17820
gattagtgat gtctgctgca gacacagatg ttgggagtgg acatgctttc ctggtcaagc  17880
aacatagagt gtctcctttc gcttctccca gcctgggcct aggttcaggg tcaggggtgg  17940
tttgacccaa cactatctcc tggttttttt cttccggtca agtgtcgggc agcgccagct  18000
tgtgtgccta gcccgggccc tgctgaggaa gacgaagatc cttgtgttgg atgaggccac  18060
ggcagccgtg gacctggaaa cggacgacct catccagtcc accatccgga cacagttcga  18120
ggactgcacc gtcctcacca tcgcccaccg gctcaacacc atcatggact acacaaggtg  18180
atgccactgg cacagtggcc tctaggcttt gggagtttgc cttactcact ggctcactca  18240
ttaattcatt aattcattca acactgtcct tatccctagt gacagcccca gtgggtggat  18300
cctctcttca tcctggatgg taccagctat ttcttttttt tttttttttt ttgagacaga  18360
gtctcgcttc atctctggag tgcagtggtg tgatctcggc tcactgcaac ctctgcctct  18420
ggggttcaag catttctcct gcctcagact cccgaatagc tggaactaca ggaatgtgcc  18480
accacgccca tctaactttt atatttttag tagtgacagg gttttgccat gttggccagg  18540
ctggtctcga actcctgacc tcaggcgatc tgcccgcctc cgcctcccaa attgctggga  18600
ttacaggcat gaaccgctgt gcccagtggt accaggtatt tctaatatca tctagtcatt  18660
cattcacgtc agcgcacctg cggtgttccc agacactggg gactctgtag gctgctgtca  18720
gacaaagtcc ctgcctccag gaccaagtag cttattagat ggaggagaca aaaaatatac  18780
agagcaataa accaacagga ttccagaggg cagcaggtgc tgggaaggac gcttgccaag  18840
gagacgggat agcgagtgct gggcagggcc actgtttcca ttgaacactg caggcccagt  18900
gcgtggggcc cacaaaaagg ttttattttt tttaaaaaat cagaagcagg ccaggtgcgg  18960
tggctcacgg ctgtaatccc agcactttgg gaggccgagg caggcagatc acctgaggtc  19020
gatagtttga gaccagcttg gccaacacgg tgagaccctg tcaccattaa aaatacaaaa  19080
agtagccaag tgtggtggtg cgtgcccata atcccaggta cttgggaggc tgaggaagga  19140
gaattgcttg aacctgggag gtggaggttg cagtgagctg agattgtgcc actgcagtcc  19200
agcctgggca acagagtgag actccatctc aaaaaaaaaa aaaaaaaaaa aaaaaaaaga  19260
atataatcca acctggattt tatttatact aacacagtca taaaatagaa tttctagcat  19320
tttgtgtgga gaaagccacc tccgtaggca tcagtgccgg ggaccacaaa agtcagaatg  19380
ctgccatagt gccagggtcc tgggggggttt tgagttttgt gtgggtcatc tctgaagagg  19440
tgacatttta gctgagacct gaacaatgaa aaggagtcag ccttgagaag atctgggaca  19500
gcgatctgca accttgttct taagggccgg ggtagtttca gctttgtggg ccacatggcc  19560
tctcagccac ttgactccag tgttgccgtg tgaaagcagt catagatagt gcacgaatga  19620
atgagcatgg ctatgttcca ataaaacttt attcataaaa acaggcaagg ggtcagattt  19680
ggcctgcagg ccacagtttg ccaaccttgg atctaaagga agaacattct aggcagccgg  19740
tacagccgaa tgtaaaaatg aatgcgctta atgaatttga aggctagcat gaggaggcca  19800
tgtacctaga ggttggaatt gagtggacag gggcaggaga ttaggccaga aaggtaggca  19860
```

-continued

```
ggggctggat cttagagcac catgtaacca cggtgagaag cttggaactt actctaagag  19920
ccctataaag ccattggaag gttttaagca gggaagtgac atgagtttct attttatttt  19980
atatattttt gagacagggt ctcaccctgt cgcccaggct ggagtgcagt ggtgggatca  20040
cagctcactg cggcctcaag tgatcctcct gcctcagcct tccaaagtgc tgggattata  20100
ggcgtgagtc tctgcaccca gctgacatga tgtttctagt tcactgagta ccacctacta  20160
agtggcagat gctgagttgg tgcttttgaa atataggaca tagaaatgag gacagaagtg  20220
ggcagtgtca aatcttacag gacctaaaat attaggggtc agccaactat ggcccacagg  20280
ccacagatct ggcccccctgc gtgtttttat gaataaagtt ttattggcac gcagccacat  20340
ctgttcattt tcctgttgtc tctggcagct ttcacactat aaatacagca gagatgcgta  20400
gttgtaacag aaagcatatg gcctgcagag cctcaagtat ttactatctg gccttttttca  20460
gaaaaatgtt gccaatcgtt attgtagact gtggtaagat ctttttattt tactctgaat  20520
gtaatggaac agtgaatgtg aacagtcaac actgttaata ccattcacac catgattgat  20580
gtggggtaga tattaaggag ctggcctcat gggaatctga cattgactag aaatagggat  20640
tgagggtgag caaccagctg gaaggtactg caccagtcct agcaaaaagt gttaggggcc  20700
tgacccgaag cagtgacttg cccaggtcag ttgtcccagg ggcacgaggt gctcacccct  20760
ccccttcccc tcatgtctgt atcccctctc cctcagggtg atcgtcttgg acaaaggaga  20820
aatccaggag tacggcgccc catcggacct cctgcagcag agaggtcttt tctacagcat  20880
ggccaaagac gccggcttgg tgtgagcccc agagctggca tatctggtca gaactgcagg  20940
gcctatatgc cagcgcccag ggaggagtca gtacccctgg taaaccaagc ctcccacact  21000
gaaaccaaaa cataaaaacc aaacccagac aaccaaaaca tattcaaagc agcagccacc  21060
gccatccggt cccctgcctg gaactggctg tgaagaccca ggagagacag agatgcgaac  21120
cacccaaaac acgcacaccc tgcccctggt gccctgagac agacacacag cctcacgccc  21180
ccaggaatgc aagtggtttc ctggtgcttc ccacggagga gttttggcag ccagacttct  21240
ggaggaattg gttgtataga agatcctagt gaccaaattc agcctactgc ctcggatctc  21300
tccagccgaa gtctgtggac tgcaagtctt tgagatgctt ctggctccca tcacctctaa  21360
catccttgtc tgggtctacc aggaacgctt catttccttg ggctgcagt  tttgtggttg  21420
aggggcctgg agaaaatcat tttctcccct tggcagtgtc ccagggccct ggatggtcct  21480
cttaccaaca tctggtcttc caggcactca aaagctggga accagcatct cagcgccagc  21540
tctaccagtt ctcgttttgg gccagaggca gcctctgcac tcccacgcct gtcctcctgg  21600
aagggacctg gttggactaa cggctaacct ggacctggaa ctgtagggcc aggggattgt  21660
ctcagggccg acgttccacc tggggcttcc ctccccaccc accccgactc caggctttcc  21720
ctttttctt  ttgttcaaca ttgtaagaac aatcaatgct gttattactg atcccaccat  21780
gattgatgtg gggtaaatat taaggagatg gcctcatggg aatttgacct tgactagaaa  21840
tagagactga gagtgagcaa ccagctggaa ggtactatgc cagtcctagc agaaaaatgt  21900
gttaggggcc tggcccaaag cagtgttggt tgcttacagt gttgattgat tttgttcttt  21960
tttcttacca cctcttttct ttccctctca tggtacctgc tcatggttat gaagctttca  22020
aagtaaagaa cacgaaatac ctcccaagta ttaccagtgg gtaccaaaaa aatgtcccct  22080
tgagtctttt ccttgttttt agatgttaat tctctccctt ggcatccggt tagcccccca  22140
ggggggcag  cattgtggag aacttgatat ttagttactg atgctcttcc aggacacgaa  22200
aagaacccat ctttgaatat caatgatttt ttttttttta agtactgttc cggggagaaa  22260
```

-continued

```
aacagtctca aaacttgaac ttcttgggaa gagaagtgtt gggctgagaa gtaacattcc  22320
caggaaatag tgagaagctc gccctgtgtt tgaaaccgtg ttggtctctg tgttcctgga  22380
agaaaacagg gaagcagcat cttttaaagc ctgttcttta aggtgtctcg ttagagccca  22440
aagtggaatc cggaaggcag ccagagctga ggctgcccca agactcagac ttgctaagaa  22500
ttacgccgcc gacttcaaac ccagagagca tctttctttt aggcgaaaac gcatatattt  22560
attttttgta agttatacca ttctttcaca ttagataaac taagttttgg gggatccttt  22620
tgtaatgact tacactggaa atgcgaacat ttgcagtaaa aaaatatata tatatctata  22680
tattttattt ctttctaaag aatggttccc tttcctttgg ggcctcggcg agggttccag  22740
ccatgtcctc tgcagggtca ggatgtggca tcttcctgtt tctgttcttt ccttttgaca  22800
acaagtcgcc tctagtggga gctgttgcca gaaagggcaa gttgtagaga tcactagtca  22860
gatggggttt agtgggaagg cgggacagcc gcaaggtgga cggagcccag gttttggggt  22920
tggacagacc ctggcttgag tcctgctctt gtcatttgct gttcttgtga ccctggggaa  22980
gtcactcagc ctctgtgcct cacttgcttt gtctgtaaaa tgaggctgat cgtacttacc  23040
ctgtgagcag tgatgtgtgc ggtactcgta gcctcggtca ggttctaaga cacaggcgag  23100
gcagaaatca catgtggcca gaacgatcct tgaaaatcct gccctcgccc tgcccttttt  23160
tttttttttt tttttttttt tttttttgc tagaggcacg gtctcactct gttgcccagg  23220
ctggtgtgca gtggcacgat catagctcac tgcagcctca aactcctggg cttacgcaat  23280
cttcctgcct cagcctcctg ggtagctggg actacaggca tgtgcccagc taatttttaa  23340
aaatttttat agagtcaggg tcttgctatg ttacccaggt tgttcttaaa ctcctgggct  23400
ctggggatcc tcctgcctga gcctcccaaa gtgctggggt tcaggcacct ggcctgaaaa  23460
tccctttatg ttagtccaga gaggcgaggc tgcgctgcag taacaaattc gccgtaaaat  23520
cttcggaaat gatcacaagg ctttatttct tgctcacgca gttcttggtg agggtcagct  23580
gcctctccag ggtaggtgac ttccctgtga caagtgatcc aggctgtcct ggttttgtga  23640
catggcctcc caagggttgg cctccaggtc cccacagtgg gagaagggag agtggacgac  23700
tctcacccac tcttctgtgt ctgaaaccgg aactgacgca gttaatccca ctcacagccc  23760
attggccaaa atgagtcaca tggccccaac ccaaccactg cgggagctgg gaaatggagc  23820
ggtgcctgtg gaagagaagg atttctccct ttcctaactg atgtggttct ggagttttgg  23880
atagcggagt agtcagacta gtgtgttcgg tttctaactt cgaactgggt gagtctgggc  23940
agtaaggaat gtctgtattt ggggagcaca ccatttctgc cacacctaaa accatgcacc  24000
aagtacatgt gcagatagaa cgttctagca ctgccattgt tccctcaagc tttcctgtcc  24060
cctgattgaa attgttggct tgcactaggg actgtggtgt acaaaggtgc tcagggaaga  24120
gccggcgagg tggtgaccat tagaatgagt agtagtgtct gggtgcagtg actcatgccc  24180
cattgaaact gttggcttgc attagggact gcagagtgtg aaggtgccta gtgaaaagcc  24240
agtaaggtca taaccattag aataggtagt atcagccagc cgggcatggt ggctcatgcc  24300
tgaatgatgt cattggcttg cattaggaac cacagagtat gaaggtgccc agtgaaaaac  24360
tggtgacgtt gtgactatta gaattagcag tattggctag acgaggtggc tcatgcctgt  24420
aatcccagca ctttgagagg ctgagacagg aggactgctt gagctgaaga gttcaaaacc  24480
agcctaggca acatagtgga actctttcta tataaaaact tttttttgt taaattagaa  24540
gtagttgagg ctgggtgcag tggctgacgc ctgtaatccc aggactttgg gaggctgagg  24600
```

-continued

```
cgggtggatt gcctgaggtc aggagttcaa gaccagcctg atcaacatgg tgaaaccccg  24660
tctctactaa aaacacaaaa attagttggg catggtggca catgcctgta gtcccagcta  24720
ctggggaggc tgacaagaga attgcttgaa tgtgggagat aaaggttgca gtgggctgaa  24780
atcaagtcat tgcactccag cctgggcaac agagcaagcc gagactccat ttcaaaagag  24840
tagtagttgg atctaccagc gggaatctta atagggatgt gagatgtgtt tagatctcaa  24900
agcctgaccc tgagtcttaa aatcccaggt cagatcctaa gcagtcccag agagctccac  24960
ctggtgtgca tctgtgccag tgtcttgggg tggggcagct gcatgctcag gtggaatccg  25020
gggctgagtt caagtttaat ccactttatg aagaggaggc agagtgaggc ataactcctc  25080
atccagggga gtggaagtac tgtggaagga agctctgttt tgtacctact acgtgctggc  25140
cctggcctca ctgtgcagaa ctctccacat tggaaaggat ccccccagac cagagaggcg  25200
taaggagggg gctggtgctt tccagtgttg aactgttcat ctgtcctcac acccaccatc  25260
gggtcctaca gcaaatttgt ttgattttct gcaaaacacc cagaatctat ccactccccg  25320
tcctcccatt gccaccacgc tggtcccagc caccccactt tctccctgca tccctacaac  25380
agctgccaca gtggtctcga ggcttttgcc cccagccccc cacacacaca tcagtgtcct  25440
caacctggtg gctgtagtga ccttatgaaa acacgcactg gccgggcacg gtggctcacg  25500
cctgtcatcc cagcactttg ggaggccgag gcaggcagat cacctgaggt caggagttcg  25560
agaccagcct ggccaacatg gtgaaatcct gtctctacta aaaatacaaa aattagccag  25620
gtgtggtggc gagtgcctgt aattccagct acttgggaga ctgaggcata agaattgctt  25680
gaactgggag gtggaggttg cagtgagcca agatcacgcc actgcacttc agcctgggtg  25740
acagagtgag tgactgatgg tgaggacacg ggctctgaag ccacactgct tgggcagaga  25800
tgccactcat tctgtttgtt ttctcatctg tcaaaagggc ctgatggtag taccttcctc  25860
atcaaaacgt tccagtaagg ggcccagtga ggtggcttcc tcctctggtc cactgaatgc  25920
gtgcgtggcg ggcatttaaa gcagtgtcag gtatacgtag ttacgtgttt gcagtggcga  25980
ggtggactgt tgagttttaa agagtctact gggcgcaggc actgaccaga gaggaagtct  26040
gcagccttga tggatgaaat tcgtgttcca cccaccagcc agaccctact ggcagcagcc  26100
catggcgggg gtattaatgg cctgggcatc ccctctggcg cgtctccaga ctgccgtggt  26160
gtgggcccaa cagcagtctc gttagcaggc tggcaggtgc cggttcccac gtgctggccg  26220
cctgtggccc accctctgct ccctggcaca cagcctagga aagagagtct ggtggccctg  26280
ggtcatcccc agctgagttt gccaaatgcc cacatggcag cccctgccta gggtcactct  26340
gcaaggcagg tggctcagct ccagccagag aagacaggct gcatctgccg cccttccttt  26400
ctctaaagga caaatgtgcc ctgtgcaatg actttggtat tacacccaga aacagatccc  26460
cactctgtcc ttactgactg ggtcaacttg gcaagtcatg tcaacccctt gagcctcagt  26520
ttcctcacct gtgaaatgga gctaggaata ggtagttgtg ggtccacagc tttgcaggca  26580
tgactagggg caggtcaaga atgcggactt cctgccccac tttgaaggtg gtagaagctg  26640
cagttagaag tttactccag gccaaaaggg gcatcacaaa acctgtgagg atgggccatc  26700
agaaagtccc atgacctgat gggcggagca ggccctgtgt ccttaagaaa aggtggagtt  26760
cttgccctgc cacccctgac accagcaaag ccactgctca agtatctgtg gatgatggat  26820
ggcagcgggg caggttagac cggggattct caaccaagtg ggtctttttg ttttgtgttt  26880
tttcagacag tcttgctctg tcacccagcc tggagtgcag tggtgtgatc ttggctcact  26940
gcaaccttct ctgcctgggt tcaggcgatt ctcctgcctc agccttcaga gtagctggga  27000
```

-continued

```
ttataggcac ctgctaccac acccggctaa tttttgtatg tctggtagag ccaggggttc  27060
accttgttgt ccaggctggt ctcgaactcc tgacctcaag tgattcacct gcctccgcct  27120
cccaaagcac tgggattaca ggcatgagcc actgcacccg gcccaactag gtggctttga  27180
ccccctgggg gattaatggc agtgtcacaa gtctggtggc ggtagaagga ggatgttatt  27240
ggcatctagt gaagaagagg ccaggggcgc tgctgaacgt cctacgatgt gcaggacatg  27300
tccccacagc acagaactat ctggccccac gtgtcaataa ggttcagaaa gcctgggga  27360
ttgccttctg tgcttccacg aacacatatc catgtattat gtcattcttg cggcaatgcc  27420
acgaggtcag tgagactccc tgactagcat acataatgtt aggatctagg gagttgtcta  27480
atgtctcacg ctgcccttcc cagcgatcta tgtgtggcct taggcttggc tactttagac  27540
ttagtccctc ttttccggtg cctgcagctg gtttggtgag tccagtatta atatactgac  27600
cgctgtcaga aagaggagtg aggaggctgg gcatgatggt tcacgcctgt aatcccagca  27660
cttttggagg ccgaggtggg cagatcacct gaggtcagga gttcaagacc aacctggcca  27720
acatggtgaa accccgtctc tagtaaaaat acaaaaataa ttagccaggt gtggtggtgg  27780
gtgcctataa tcccagctac ccggcaggct gtagcaggag aatcgcttga acctgggagg  27840
cagaggttgc agtgagccga gatcttgcca ctgcacttta gcctaggtga cagagtaaga  27900
ctctgtctca aaaaacaaaa aaagaaatgt gtgaggaatg caacaagctg tgcattgacc  27960
acccttggtt acagcaagtt ctccacgctc agccgggtcc agcctttggc tgtcagcagc  28020
atctggagcg gaactgtgaa cagaaacact ccaggtgttc cgacgggtgc tggggcgccc  28080
ccagggagct ggaatttggt tttagcaac cacatatagg aaatgaaccc gccagccaca  28140
gtatctcacg cctgtaatcc cagcactttg ggaagctaag gccagcggat cacctgaggt  28200
caggagtttg agaccagcct ggccaacatg gtgaaacccc gtctctacta aaaatacaaa  28260
aatcagctgg gcgtggtggt gggcgcctgt aatcccagct gctccagagg ctgaggtggg  28320
agaatcgctt gagcccggga ggtggaggtt gcagtgagtc aagattgcac ccctgcactc  28380
cggcttgggt gacagagtga gactttgtct cggacaaaaa aaaaaaaaaa aaaaaaagaa  28440
ccaagtcctc gggcaaattc tcccattgag ggctgtgaag tcttggctcc tctgttgttt  28500
gttttggaaa ccaaacttgc atatttgact ttctcatgcg tggagaggac ccatgcttgg  28560
catggggggg cacctggttt ttgtgtcctt ggagctcatc tctggtgggg gaggaggagc  28620
agcaggagat gcgagggctg tagttctcag tcctggccgc acattggaat cctatggggg  28680
agctttaaaa ttatacacca aactcggcca ggtgcggtag ctcacgcctg ttatcccaac  28740
actttgggag gccgaggagg gtggatcaca tgaggccagg agttcaagac cagcctggcc  28800
aatatgctga aacctcgtat ctaataaaaa ttacacaagt tagccaggca tggtggcgca  28860
cgcctgtaat ctcagctgca cgggaggctg aggcaggaga attgcttgaa cccaggatgt  28920
ggaggttgca gtgagctgag attgagccac tgcacttcag cctgagcaac agagtgagac  28980
tctgtctcaa aaaaaaaaaa aaaaaaaaat acacacacac acacacacac acacacacac  29040
acaactggag aacagagcat ggtcactggg ggcaggagcg agagtgatgg gtgtggtcgg  29100
aaaatggtgg tggctattcc gtatcctcac cctggtgtgg attcatgagc ctacatgtgt  29160
gataaaactg catgggacaa aataaacaca cacacacaca ggagtacagg taaaacggga  29220
aatcgagcaa gattgttgtg tcaatgtcaa caccctggct gtgatgcttt atcctagagt  29280
tttgcaagat gttaccattg ggtgaaatgg ggtaccaagt acacgaatct ctctatatta  29340
```

-continued

```
ttgtttcttt aactgcatgt gagtctggga ttatcccaaa ataaaagtgt taatttgtaa  29400
aaagtacaca cagcatggca gttcccagcc tcagagattc tgatttaagg gtctagccgg  29460
gagcctgggc atgtgcttga ggcccccagg tgagtccaga gtacagcggg gctgagagtc  29520
gctgttgaca ttggctgcag ggtggacagg gcgagatggg ccctgcccgg gcagacctgt  29580
gtattgctag gtccttccgg ctctgatgct ctgtgataat tggccacttt ctctgccatt  29640
ttcctcccag agagcaaaca caggtctaga ctcaatatcg tgtggagcta tcgatgacca  29700
cgggtcactt ccatctccag cactgcaggc tgtgcgggct ggtccaactg gggtacggtt  29760
gagggtcctg gctcagacca ggcctgactc ctgggccagt ctgtaaaaca ggcccttctg  29820
ggccagcagc tgggccgggc tgccgctctc tgccacctgc cccttgtcca tgaccagaac  29880
cctgtggggg agagggagac agagaggctc tctggacacc agcccaggct ctcggcagct  29940
gtgagagccc agtgtgtctg cgctgaggtt ttctccatag aagtcctgct ttccatgcgg  30000
ctccctggcc ctcacagctg ggttggaagc gtgtgctggg cgcatgtcct tgggcagctt  30060
tcccacttgg catgtgttcc cgggcattcc tcccgctctg gccccattca ggacccctcc  30120
agctctaacc cgaagcccag tggcccagga ctgcctccgc ctccttcccc caccactgca  30180
gggctgctgt gaggtcaggc cggggcggga gccttaccgg gcacagtcca tcacggagcg  30240
caggcggtgg gcaatgagca gcacagtgca ctgtgcaaac cagctcccga gcatggcctg  30300
catctgcagc tccgtgccag ggtccacggc agcagtagcc tcgtccagga tgaggatctg  30360
ggtcttccgg agaagggcac gtgccagaca caggagctgt ttctggccca cgctgggaac  30420
gattgggaca attagctggg acgtgcgttt gtcggcacat ggtgatgtgt gggtgtgccc  30480
agaaacaggt ccctgaagca gtgcaggagt gaggtgcctg tgttcaggca tccccacaca  30540
tggggtctgg ggtctgtggt ctgcagaact gataggaagc ctgttcctgc catctttgag  30600
caggctgact gtaggcaggt cattcaaacc ctttgtgcct cagtttcccc acctgtgaaa  30660
tggctatttt ctttttctg tttatggctc tttttttctt cttcgttttt cttttttttt  30720
ttgagacgga gtcttgctct gccacccagg ctggcgtgca atggcacaat ctcagctcgc  30780
tgcaacttct gcctcccggt tcaagcagtt ttcctgcctc agcctcccaa gtagctggaa  30840
ttacagtcat gcgccaccat gcctggcttt tgtattttta aagtagagat ggggtttcac  30900
catgttggtc cgacttgttt gaaactctca ggtgatccac ctacctcagc ctcccaaagt  30960
gctgggatta caggcgtgag ccactgcgcc ccggtagttc tatttctagt ttgtttttg  31020
agaaatcatc atactatttt ccatagtgac tgtactaatt tatatttccc ccaacagcga  31080
aagcacagct ttcacttcag tcatgccgtt gcaaacaaac ctacaatgac tcactgctgc  31140
ttcaagaatc aaatctacag tcttcctaag acattcaagg ctggtgtcac gtgggcctta  31200
aatacagatg tgtacaacac ctgggtggga ttccaggcgt gatccaccgt gcctggcctg  31260
tttatggcta tgtccagttc tatttctagt ttccaccttg tgccaaacac attctaagtg  31320
cttgtatata ttcactcaat cctcataatg tccaccaagg tagatattat tgttctcttc  31380
ttttgagaga agaggacaca gatacagaga agctcagtgg cttgaccaag gtctcaaggc  31440
tagtggtggg tccataattt gaacccaagt cctctgaccc cagagtctgt gctcctaatg  31500
gatccgtcct cgctgaatcg tgacgacatg gcacataaaa gtgtgtgggt ggcggggcac  31560
ggcggctcac acctgtaatc ccagcacttt gggaggctga ggtgggcgga tcacgagatc  31620
aggagatcga gaccatcctg gctaacacgg tgaaaccctg tatgtactaa aaatacaaaa  31680
aattagccgg gcgtggtggc gggcgcttgt agtcccaggt actcaggagg ctgaggcaga  31740
```

-continued

```
agaatggtgt gaacccggga ggcagagctt gcaagtgagc caagatcgcg ccactgcact  31800
ccagcctggg cgacagagca agactctgtc tcaaaaaaaa aaaaaaaaaa aaaaaaaagt  31860
gtgtaggctt gtcacagaat aagcccttgg catggagtag caccccttcgt ggagggtgga  31920
ggagttgaga ttccaggttg tgagcccagt gagcccctga cccaggtggg aactgacccc  31980
tggggcccca gcatggctgt cttgcacagt aagcccttcc atgaaacagc atccttttac  32040
atgatcagaa cctactatgg tcatgcaggc gttagagtgc ctgggtcttg tcccaacctc  32100
actactttta agctgtgtga cgtcaggcaa gccccaggcc tccaattcca actctgtgaa  32160
atgatgttat caggagtgtg actcaggact aaaatgagta tttactcttt gctctatgcc  32220
tgccactgtt tcaacaactt tgtgcatata attcaatcct tgcaaggtag gtaggtgcta  32280
ttattcccac cttacagatg aggaaactga ggcacacaag ataagttgcc taagatccta  32340
cagctagtaa gtggcagggc ggggcggggg tgggggtgtg gggtgggggg cctggatttg  32400
agcccaggca gtctgtcacc tgtgtatact cttacccacc aagcaacgct gcctctctag  32460
tgctggaaat tattgcctac cacaagccct tcggacaccc tcagggtcag aggggtttat  32520
aaatccagaa caccttaggt tttttttgt ttttttgag acggagtctt actctgtcac  32580
ccaggctgga gtgcagtggc acaatcttgg ctcactgaaa cctctgcctc ccgggttcaa  32640
gcgattctcc tgtctcagtg tcttagcctc ccacgtaact gggattacag gcgcctgccg  32700
ccacacccag ctaatttttg tatttttagt agagacgggg cttcaccata ttggtcaggc  32760
tggtcttgaa ctcctgacct caggtgatcc acccgcctcg gcctcccata gtgctaggat  32820
tacaggcatg agccaccgcg cccagccact ttggtttttc taaaggcata tacctataca  32880
cctatgttca tagtggcatt attcaaaacg gccaagaggt ggaaacagcc tgggtatcta  32940
ctggcagata aacggataag caaaatgtgg tctatccatg tagtggaaaa ttattcggcc  33000
ttaaaaaggt agagaatctg acacatgcta cgatgtggat gacccttgaa gacatcatgc  33060
tgtgtgaaat aagccagtca caaaaggaca gatcctatga ttctgcgtct atgcagtgtc  33120
tagagtagtc acactcagag agacaggaga atgctggtgg ctgggcgctg gggagggga  33180
caaggagagt tagggtttca tgggtacaga gttgtagttc tgttgtgtaa cagtgtgaat  33240
gtacctaaca ctacagaaac tatacactga aaaatgggtg agatgggccc ggcgtggctg  33300
ctcacacctg taatcccagc actttgggag gcctacgcaa gttcgactgt agcctgggca  33360
acatggtgaa accctgtctc tacaaaaaat aaaaagatta cctggccctg gtggctcaca  33420
cctgtaaccc cagctactcg ggaggctgag gtgggaggaa tgcttgagcc tgggaggtgg  33480
aggttgcagc gagccttgac ctcaccactg cactctagcc tgaatgacag agccagaccc  33540
tgtctccaaa gaaaaagaaa aaaaaaaaaa aaggttgaga tagtaaattt tatgtgtatc  33600
tttccacaca gctttttgtt gttgagacga agcccaggat ggagtgcagt ggtgcaatat  33660
cggctcactg caaccttcgc ctccctggct caagcgttct tcccacctca gcctcccaag  33720
taactaggac tacaggtgca tgccaccata cctggctaat actgttgtcc acagagatag  33780
ggtcttgcta tgttgcccag actagtctcg aactcctggg ctcaagcaat cctcctctct  33840
cagcctcctg aagtgctggg attacaggca tgagccactg tgcccagtcc acacttgaca  33900
tttaccaaaa aaaaaaatcc tatattatag tcccagtgag tggtgaggtt accacccgat  33960
atcaaacaat attttcatag caaaataaat actgagcaag agcaataaag gctatcagta  34020
gccctgtgtc agttgaggtt gggttttgcc accaagtaaa tatagaagac taactgctaa  34080
```

-continued

```
tttagggggg aaaaccttgg tattcagaga ctgtgtcaga gcttggaatt gcagataaga  34140
gacatgtggt tattaatgta acagagtgat aatcctatcg gggaggcat  ttcctgaagg  34200
cccttgggga gggcatggcc atcccctcct ctcccacctg caggtcccag ccatggtggg  34260
acgaccatac ctcaggtcct cgcctcggtc agcacacttg tactgcagct ggccgggcag  34320
gctggccacc aaggctttga gctgcaccgt ctccagggct gcccagatag cctcgtccga  34380
gtgctcctgc agcaggtcga ggttcatccg cagagagcca gggaacagga tggggtcctg  34440
gcggggaggg gcggtgggtc agagccgggt cccaccatgc ctcccatctt tgcccacccc  34500
ctccaccagc ctcacctggg ggatgatgct gatcctggag cgcagtgtgt gcagccccac  34560
gtgggcaatg gggaccccgt cgatccagat cccaccctca gctgcctcct ggagccgcag  34620
cagcccactg gccagggagg acttccctgc cccggtcctg ccaacgatgc ccacctgccc  34680
ggggttggga ggaaaggcct gctctgacca gagggtttgt gggcatttat tggggagatc  34740
tttctgctgt acccgagatc tgtctatcca tccctcattg tgtaaaggtc taccttccat  34800
ctctctttcc atctgtctac ctttctatat atccacccat caatccatcc agtcttccat  34860
ctgtgttctt ctctatcttt cccttatcct gatatctctc tcccatcttt ctccccaccc  34920
ttcctttagt tcctccatct ttcctcatcc ttctatttac acctctccat catctctcat  34980
ccttttttct accccatccc atccatctgt ctgtccgtcc atccatccct tatccttttt  35040
tccaccccat cctgccatcc atccatccat catccatcct caatcccatc cctccatctc  35100
tcttccaccc cattccattc atccatccat tcatctgtct atccgtctct cgtttcttct  35160
tccctattca tccatcaatt cactaatcct ttcattcatt tattttctcc catccatcca  35220
tccagtccat ccttccctca tccatccttc cattcatcct ccatcttatc catgtgtcca  35280
ttctgttatc catctcccat gctgttatcc accctccatc cttatctctc ttgctactat  35340
tgcatcctca gtgtctgaca catggtgtgg gttcaacatt atttgtttaa ttaatgatgg  35400
aaacatgtgg gtcaccccac tgtatgccaa gtacctgttt aggcaccgga agtatagaaa  35460
ttaaagagtc cttgctccag tgtgcccatc atccggtcta ggaaacagtg caattgagta  35520
aatgtaatac agtgtgatga acaatgcttt atttatttat ttatttattt atttttgaga  35580
taaagtcttg ctctattgcc caggctggag tgcagtggtg cgatctcagc tcactgcaac  35640
ctccacctcc caggttcaag caattctcct gcctcagcct ccctagtagc tgggactgca  35700
ggtgcctgtc accatgctcg gctaattttt gtatttttag tagacacggg atttcaccat  35760
gttggccagg ctggtctcaa acttctggcc tcaagtgatc tgcccacctt ggcctcctaa  35820
agtgctggga ttacaggtat aagccacagc acccagccaa caatgctgtt tattatcaag  35880
gtctggacct ctggcaatta agggaagcaa ggcagtgctg ctcatgctgc ctgggatttg  35940
acagaggtaa taagagaaga cctcatggag gaagggatac ttgcatggaa gcttgaagga  36000
tcaataggag ttcaaggaag gggaacactc caggtaaacc acaccaagtg ggtttccaaa  36060
actagaagct catggagctc acagcaccat gtgcccccct ggccgagagg cagctgctcc  36120
acaatgttgg ctaagccctg gcagagcaat gaatgagagg gggaggttgg cagggcctgg  36180
gttgggtaga gccttgaatg ccaagctcag gaattcacac tttaccccaa gggaagctgg  36240
aactagtaga aggttttgag caggggaatg acatgcagtg tcattcatgc tgataaaggt  36300
cacaggatgg ctgggcatgg tgggtcatgc ctgtagtccc agcactttgg gaggccgagg  36360
ggggtgattg aggtcagaag tttgatagca gcctggccaa catggtgaaa ccctgtctct  36420
actaaaaata caaaaattag ccgggtgtgg tggcaggtgc ctgtaatccc agctactcag  36480
```

-continued

```
gaggctgagg caggagaatc acttgaatct gggaggcgga ggttgcagtg atctaaggtc  36540
acaccactgc actccagcct gggcaacaga gtgagactct gtctcaaaaa aaaaaaaaaa  36600
aaaaaaatca caggagagca gattggagct ggtgagacag gatccactgc tttttagggg  36660
acaaggagag gacagggagg aagcctctgt aggttcagag ggagggagga aagggattca  36720
gtgaaggggc ctgatgaggc atctgtaaaa tgggatagta ctagcacctc acttaggggt  36780
tgttgtgaga gtgaaaacgc aaataataaa agcattagta aacatttctg gagcactttc  36840
tatgagctaa gcatgttcta tgtattaact caaacttcac aacaactcag agatcagtat  36900
taccagtccc aatttacaga tgggaaaact gagactgagc tatgaagtgc ttttcccaat  36960
gtctcccagc tgaaagcaaa tatcccattt gtgcaaactg gaaaatgtac ctggagcatt  37020
taacacactg cccagcacat attaggtgct gggttaatgt taaaggaaga aggaagtcac  37080
ggagttgctt cctcatctgg ggacaccaag gtggatgagg aagtcaccag atggaagcag  37140
gtttggggaa ggtgaggagt tcattttagg gggtaatggg tctgaaagct aggggacctg  37200
aggtggggac actgtggagg tagctggtgc ccagggttta gggccttgtc cctggagtcc  37260
tttggcctaa actccatgaa gaagacattg tgagagaacc actcaccttc tctcctgcgt  37320
ggatcttgaa ggacacgccc tgcacagcca gcgggagctc aggtcggtat cttagcccaa  37380
agtcccggaa ctcgatctgc ccgccctgag gccagggggg ctgagctgca catgtgggca  37440
gcctccaggg agcctggagc aggaggggaa actgagtcag aggagccttc ctctaagact  37500
tcacacaaga tggcccacct ctatcagctt cagttttctc ttccgcaaaa tggacgtatt  37560
tattgctgtt ttacagggtt gttatgggaa ttcaacaaga gagggcatgg actatgtcaa  37620
tgctaaaaac agatggtggt ggctactttt agtctatttt attgttatta ttagccactg  37680
tttattataa aataatctct ttttctatag tgggagcaga catttctctt tgtctttgtg  37740
aaaggacatg actgtgcagt gggaagacca atactgcctt tgctgtgccc gtgaccttga  37800
acagatcatt ctaccccctt gagtcttggt tttccaatct gggaaatagg gctaataaga  37860
gcagcagaca tgtattgagt gtttgcaatg gaccaggcac tctattaaat catttctttg  37920
caggatctca tttgatcctc ccagtaaact caacgctgtt atgttactgt tacattagtg  37980
ctatgctgct gttcttatcc tttcttccac ccaatcccat ccatccattc atccatccat  38040
ctcttatcct ttatccaccc catcccaccc atccatccat ccatgcatcc atccatccat  38100
ctccaatccc atccctccat ctctcattct tccatcccat tccatccatt catctgtcca  38160
tctctcacca tttcttctac cctattcatc aactaattaa ttcttccttg ttctgttact  38220
gtaatgttac tgttatattg ctaacacatt atatcatgtt gctgttttgt taccgttgcg  38280
ttgctatgtt gctgttctgt ccttataatg ctactgttat gttgctggaa ttttgccatc  38340
atgttactat aatgttgctg ttttcttact gttacattgc catgttgcta ttccgttact  38400
ataatttcag ttattttgct ggaatgttgc catcatgtta ctataatgtt gctgttttgt  38460
tactgttaca ttgttatgtt gctactctgt tactctgtta cagtcgtgtt gctgggatgt  38520
tgctgtcatg ttatgatgtt gctgttgtgt tactattgca ttgctatgtt gctgttttgt  38580
ttctatcatg ttactaaaat gttgctatta cgttactatt acattgctat gttgtggttg  38640
tattgctgga atgttgccat catgttacta taatgtctct attatgttac tattacactg  38700
ctatgttgct attctggtac tgcaatattg tggttatgtt gctgttacat tactgttaca  38760
ttgctgttgc attactctca tgttctggaa tattgccatt gtgttgctgt tgccattatg  38820
```

-continued

```
ttactatcat gttgcagcta tgttgctgtt gcaatgctgt tccttgtggt tccctgcact  38880
cccatgggtg acctgctttc ctcaagctca gaagcaaagg aaccaagatt tggcctggct  38940
ccaaacctta tgctcctaac cactgctgcc accctgtctg tgactctgac ctatagtggt  39000
gggggttgag tgaggggaga agagggtata aactccaaag cctgtagcag atgtcaacag  39060
ggacccattg cccccccac aatatgtcct tgctgggacc ccctccccac ctcccgccca  39120
tcacctcctt gggcgtccag gcatagtcct gcatccgctc cactgacacg atgctgttct  39180
ctaggtctgt ccagttgcga acaacccact gcagtgtctg ggtcacctgg tgcaagaaag  39240
cctctctggc tgggtttggc aaggccactt gagggcttgc aacagccccc ctggtttccc  39300
aacctttctt gggaggccag acccagggga gtaaagaggg gaggcaggaa tgggacagtc  39360
tgaggacctg ggcccagggg attgggattt ggatacaacc aacaggtccc tctcttcctt  39420
cagtagaacc agagcatgca gagcaaaaag aagccctcag acatcagctt gtacaaactg  39480
gcttgatgca ggtgagtaga caggatcaga gagggtgtgt ggccctccca aggacacaca  39540
gcaggaccca ggcccactga ttccattctg acggctttct cgcagcgact gggtggccac  39600
caatttccca tgacacttag aaccactcca agctcctccc tatgagccat tagcagctct  39660
agccctgcca tcccatcccc aaccttgtct cccagcaccc ctgccttcac ccaccctctc  39720
cagccacacc cgtcttcttg ctgttcctct aacacaccag ggatgaacct tcaactccca  39780
ggccttttct tcctgctgtt aacctcactt cctcctaagt cacctcctca gagaggcctt  39840
tctggatgca gtaggaaagt tccctcactg ccacccaaca tgctccagcc tcttacttca  39900
tccttaagct tagcagcctt gactgtaaaa tgaggataat aacagtgctt ctctgatggg  39960
gttgtgggca gtattaagtg agttaatatt tataaaattc ttgtgcacag tggctcatgc  40020
ctataatccc agctttttgg aagtctaagc aggaagattg tttgaaccca ggaattgaag  40080
gctgcagtga gctgtgatca caccactgca ctccagtctg ggcaaaagag tgagaccttg  40140
tctcaaaaca aaacagctgg gcatggtggc tcacacctat aatctcagca ttttgggagg  40200
ctggggcagg cagaccactt gaacctagag tttgagacca ggttgggcaa catggtgaaa  40260
ctgtttctac caaaaaaaaa aaaaaaaaaa aaaaaaaaaa attagccagg catggtggtg  40320
catgcttgta gtcccagcta attgggaaag tgaggtggga gaatcccttg agcctggaga  40380
tggaggctga agtgagccaa gatcatgcca ctgcactcaa gcctaggcaa caaaatgaga  40440
tcctgtctca aacagcaaca acaacaaacc aaaacgaaca aaaacatata aagctcttag  40500
aataatgcct cctccataac aaatgcttat gagtgtatat atatattttt ttcgtagatg  40560
tcatgaactg acattacata ctgttaatag ttaacaaaaa ttagccaggc atagtggctc  40620
acgcctgtaa ttccagcaac ttgggaggct gaggcataag aatcgcttga acccaggagg  40680
cagagttctc agtgagccga gattgcacca ctgcactcca gcctgagtaa aagagagaga  40740
ctctgtcttc aaaacaaaac aaaagttaac aatgcactag aaatgtcctc cacaggatat  40800
gctttgtctc aactagtctt tataacatca gaagtagtgg gatttctggc ctgtctttcc  40860
aaggagcaca ctgacactcc acaaggaaag actcttgccc aaggttgcaa gttcacctta  40920
gctgagtctg gctcttgtag agctgcgtgt ccctccttgg tggagggact ccacacacca  40980
tggtggtttg gacacagggt cttcaaaggt cccactagca ggggtccgac agtctctgcc  41040
tctgtctgtc cctcaagccc agtttgggga tgtggggagt acctggaggg cagcagagac  41100
agagaagccc acgaggccag cactgaggtg ggctttgctc agcacagcac acgtggcagc  41160
tgcaaacacc aggccattcc ccaggagctc cacattggcc gcaagccacc tgcaaaggga  41220
```

-continued

```
agcgacagca gggtgagtgg ttactctcat ctgcagggag atgcttctct gggcacaagg  41280
actggtcatc acaccagctt tgtacacaca ggggtcccag caatggcctc cacatgcaac  41340
ccaggctcag ggagtagagg aagatgacac cgtcctgtct caactaagcc cactttaggg  41400
tctggggtac actcggtgtt ctgaagagca tccctgtgtg gctgcttttc tgtccctgga  41460
atttgccaag ccatgtccac ctgccattcc cctggcctga accatggcct ccatggtttg  41520
gctctgtgtc cccacccaaa tctcatctca aattgtaatc cccacatgtg gagggaggga  41580
tctggtggga ggtgactgga tcatgggggc agttttcccc atattgttct cgagatagtg  41640
agttctcaca agatcatatg gcgtaaaagg atgcggcagt tcccacctca tgctctccct  41700
ctcctgctgc catgtaagac gtgccttgct tccctttcca ccatgattgt aagtttcctg  41760
aggcctcccc agccacgtgg aactgagtca attaaacctt cctttcttta taaattactc  41820
agtctcaggt agttcttttt agcagtgtga agatggacta atacacagcc ccagctggct  41880
ggggacctga gatgaaagga aaaaggactt cacatgtatt gagcacctag tgtgtacttg  41940
accctctcca cactctggta ccagactgct tggattcaaa tcctggctct gccagtatta  42000
gctgtgagac cctggacaag tttccaaacc tcactgtgcc taggatttat catctataga  42060
acagtttctt cctggtgaag ctgttagcag aattaaataa attaatctac atagattgct  42120
cagaacagtg ccaggcatgc agtaagcatg ttacaggtct tacctatgag tgtctgtatt  42180
taatcctcat atccactcca tgagcacgat cccagtttga caaatgaggc tcagagaggt  42240
tatgtaactt gcctgaaatc aaccagctgg taagtggcag agctgggatt tgaacctgtg  42300
tctatttgtg cttaaagctt gtgttcttgt tcttgcttag tacctaaaga tggctgagga  42360
tgcttatatg gctgctttat caccaaggca aaagaggttg atccagttgc ctggcaacag  42420
aagcttcttc ctgtaccccc cgcccacctg ctgttgagaa tctctcggtc atgttccatc  42480
tgcccacggt gagaactgat agactgcctg tgggatctag cctcaactat gtccctgact  42540
ctctgggtga cctcgctacc atacaatatg acctcaggtc tcaccctcta aggatatgga  42600
tgaattgcaa ggtcttctct gccctggctc ttcctacctg tcagccacca gtcgcgggaa  42660
actgatcctc tggctttcat ctacgcgagc attgttctga gccacaaagg gggcctgggt  42720
tcggaatgcc cggaccactg tgctgccctg gaacgtctca gccatgtggg agcagacaga  42780
cgagtagctg gctgactcca agcgtctcag ctggcatgag ctaaccacat acaggctctg  42840
agaaggatgg atgggagagg gaagaggaga agccacagac atagagaggt agtttccaga  42900
agcacagaga gccccaagta caggattcca gaccaggatc tgttaacagc ttactgtgtg  42960
accttgggct agttgcttgc cctctctggg ttctcatttc cttgcagaat cagagttcta  43020
tggttttttt gaaaatcacc tggggagctt caaaaacctc taatgcccca ccccagaatg  43080
actgaatcgg aatctctgga aatgtcacct tgactttggt gctgtttaaa tagccttcca  43140
gatgattcta agggacagcc agggttgaga aaccaccaat ttagtttaag tgtctcactt  43200
cccagcactg aggccgacta cttcatttac ggctggtcag tgggagaaca aaactgtaag  43260
gggcaatgaa ggcagttggc caagtcagtt tcactcatgt aacccaaggg ttacatgcca  43320
ggtgatgtgc agaaaatatt cgttatttgg tttgcagctg caggttgggt gcagctggca  43380
gacaggcagg cagggaggaa ctgaatttgc tgaacaccca actgtatgtg ccaggctttt  43440
cacacagtgt ctcattcatt gcagagtgag cattcgcgtc attcatcagt tagtggtgag  43500
aacatccaag gctcggggga ttcagcagct gtcctgagtg ccacagtaag tgatagagcc  43560
```

-continued

```
tggatttaaa cccatctttg cttgactcta aagcttgaga cagaaacagc ccatcctcgg  43620
agtcaagtga acttagagaa gacctaggac aattgtcggg gacagtggta gccatgggtt  43680
ttgttgtttg ttttttgaga tggagtctct ctctgtcacc caggctggag tgcagtggtg  43740
caatctcagc tcgctgcaac ctctgcctcc cgggctcaag caatcctccc gcctcatcct  43800
cccaagaagc tgggattaca agcatgcgcc accacactgg ctaaattttt gtatttttag  43860
tagacggagt ttcaccatgt tgaccaggct ggtctcgaac tcctgacctc aagtgatctg  43920
cccacctcag cctcccaaag tgctgtgatt agatgtgtga gccaccatgc ctagccctag  43980
ccatggtttt tatctgacta ccatgttttc tacttctggt ttcctgtggg aaagggctgg  44040
gttggggtgc tgtcaatcat gggacctgat cagagaggtg gtcacatgat gcagcctagt  44100
gtatcagaat ctactatcca ttcagttact gtgacgagtt cagagatgga cacatgatcc  44160
acaaagggcc aatcagaacc ttccctggga ttaatatatg actactgagc tgaagaaacg  44220
tttttgcat gttgagttgc taaggtgaga tgatatgata gctagtggcc ataagacctg  44280
ccctggaaag agagcgtgta caaaattaga ccagaggtaa gccagtggtt cctaaacatt  44340
tgtgtacatc agaattactt ggagggttaa ttaaaaccta gattcatggg ccgacccaca  44400
tagtatctga ggcagtagtc ctgggctggg gcctaagaat gtactttgct aactagtccc  44460
caggtgatac tactgctggt cctggggtca cactttgaga agcactgagt gaagatatgg  44520
agagagtcac tgtgtcctga tgacaactgg gcccatgccc ccaaggaaat ataagccatt  44580
aaattctatt cttttggtta agctaatttt agttggtcgc tggtcccagc aattgaaaga  44640
atctagcttc atataatagc ctttgagacc ttgcaatgcc tttttggctt ccagataatt  44700
ggagaggaag aaattacggc aggataaaaa cattacgcgt gaaaggctct ggcccttaat  44760
atttaactgt gccgtggggc acaggggctc atgccctgta atcccagaac tttgggaggc  44820
caaggtggga ggatcacttg gggccaggaa ttcgagacca gcctgggcaa cacaggaaga  44880
cacttgtcct acaaaaataa atttaaaaat tagccagtca tggtggcacg tgcctgtagt  44940
cccagctact tgagaggctg aggtaggagg atcacctgaa cccaggagtt caaggctgca  45000
gggagctatg atcacctatt gcacttcagc cttggcagga gagcaagatt ctgtctctct  45060
aaaaaaaaga actttgatgt gaacatttag agacagacac tagtggagat accagaaaga  45120
ctgtagtgtc cctgtccctg ggaattctag gaacagcccc tagatgtcca gctgggtgaa  45180
acctcatata tggagtcttc cccagagaca ggggactggc tgagttgacc tcagccggtc  45240
ccggaagcct ccctgacctc tccgtacctg aaacccagcg tagaggagaa acagtggcag  45300
gatggccaca gtggccagtg gggtagccac tgccaccacc aggctgacct ccaggagtcc  45360
aaaggcgtac atcagcaggg accggagttt gtctggaatg tccacgtcaa ccgtgtctgt  45420
ctccttggag aagcggttta gcaggtgacc aatgggtgtc cgctcaaaga agctgatggg  45480
agatcgcacc acatcccaca ggagcctctg gaagagcaac ctggatgccc gggccccacc  45540
taggagcacc gcagccatgg aggcaaacag cccaatggct ggggagggag aggaggtaag  45600
agcatgaggg ctggagaccc tcaggagcgg cccacggggc cctgcgcagg tctctcccgc  45660
taccccatgg tggacatctt atggcttggc caccctgatt attatatttt tttgagacag  45720
ggtctcactc tgtcacccat gttgaagtgc agtagcatga tgatggctca gtgcagcctt  45780
gacctcctgc actcaagcga tcctcctgcc tcaccctccg agtagctggg accacaggtg  45840
tacgccacca tgccggctaa tttggggtat ttttgtagag atgggatctt gctatgctgt  45900
ccaggctggt ctcgaactcc tgggatcaag tgatctgcct gccttggcct cccaaagtgc  45960
```

```
tgagatgaca ggcatgagcc actgcgcctg taccctgctt gtttcttgat gtaatgggtt  46020
gaagagtgtc ccccaaaatt catttgggat gggtcctaaa ttcagtgact gccatttata  46080
taagaatact agaggatact cagagacaca gcaggagata tgaagatggt gacacagatg  46140
ggagggtgta tctacaagcc aaggaatgcc agcgactgcc ggcgaccacc agaaaccagg  46200
agagaagcct ggggtgtatt ctccatcaga gcctccacga ggggccgggc acagtggctc  46260
atgcctgtaa tcacagcact ttgggaggcc aaggcgggtg gatcacctga ggtcaggagt  46320
tcgagaccag cctgagcaac acggtgaaac cctactaaac cctactctct actaaaaata  46380
caaaaattag ctgggcgtgg tggcaggcac ctgtagtcct agctactcag gaggcttagt  46440
caggagaaac actggaaccc aggaggcaga ggttgcagtg agccataagc cgagatcgtg  46500
ctactgcact ccagcctggt tgacagagca agactccgtc tcagaaaaaa caaacaaaca  46560
aacaaacaaa aaaaccaaaa aaacctccac aaagagttaa cactgctgac accttgattt  46620
tagacttcag gcctcagaac tgcgacagaa caaatttcaa ttgtgctggg ctcccaagtt  46680
tgtggcaact tgtttggcag tagccctgtg agagaaatgc acatccttcc tcccagtgct  46740
aatctgtatg cctggggtgg ggctaacttc tcctctgggg tggggcaaat ttcatccatg  46800
gccaatccaa accactgcag ttggttcagg gatgaacaca taacccaagt caggccaatg  46860
acagggagac ctgggacttc actagaactt ttggaaaagt ggtacttggt tgttggaggt  46920
agccaagctg gagctgtgga atatcatctt actgccaggg gcagcagcta agctggacag  46980
gaagctgtca cagaggaggg aaataaagcg atttcttgtt tggaccccta catccagcca  47040
tacctgaagc cagaaatcta gggatactgg tcccaagagc caatcaattc tcttgttgct  47100
taaacacttt gaattggagc tgaatttgtt tattttcaga cggagtcctg ctctgtcacc  47160
caggctggag tgcagtggtg caatctctgc tcactgcaaa ctccacctcc caggttcaag  47220
cgattctcct tcctcagcct cccaagtagc tgggattaca aacactgaca ccatgcctgg  47280
ctaatttttg tatttttagt agagacgggg tttcaccatg ttcgccaggc tgatcttgaa  47340
ctcctgacct caagtgatcc acccgcctcg gcctcccaaa gtgctgggat tacaggcatg  47400
agccactgta tctggcctgg agctgaattt tttattcttt gtattcgaga gtcataacca  47460
atttctctct ctcagctccc atctctccat ctttagggga gagtaagact tgcccttagc  47520
tatcaaatga gggatggaag tggaaggatt ttgaaagggc tatttgccac ccaaatgagg  47580
atttgggtta attccagggc tcggctgact ctgagaatcc ctaatttcct cttggttaag  47640
taaccattcg ccttgagtat tccactgtac atgcagttgt ggtgagtagg tgtacaggtt  47700
cttaggacta gaagagtcct caagttcagg cctggcgccc cctattttac aggggaggtc  47760
acaggctcac agcattttgg tgatgtggcc aatgtcaccc agtgaatgag gacgaatcaa  47820
catgaaaacg aggcaactgt cctttaaaga tgaagccagg ccgggcgtgg tggctcatgc  47880
ctgtgatccc aacactttgg gagtttgagg cggaggattg cctgagccca ggagtttgag  47940
accaggccgg gcctggtggc tcatgcctgt gatcccaaca ctttgggagg ttgaggcgga  48000
ggattgcctg agcccaggag tttgagacca gcctgggcaa cacggcgaaa ctgtctctat  48060
caaaaacaaa aattagccag catggtggca tgtgcatgta gtcccagcta ctcgggaggc  48120
tgaggtggga ggattgcttg agcccaggag gcagaggttg cagtgagccg agttcgtgcc  48180
actgcattcc agcctgggtg acaaagccag acccagtcta tatatatgtg tgtgtgtgta  48240
taaataagaa gccaaactca catgtgcact cctgttactc ccttcagcca ggccacgtat  48300
```

-continued

```
taaaaggaga agaaccaggg gttggggaca gggtgggcga ggcaggagaa gggtgggtgt  48360
ggttgcaaaa gggcaacacg agagcgcctc gtggtgacgg tgttgttcag tatctcaact  48420
gtcaaccatc gtgatggatg cgagagactg aacaggggat acgactgcac agaggcaaac  48480
atgcgcacac ccacgtgcaa gcaaaactgg ggaaatcaca atgagatcca tagggccggg  48540
tgcgggggct cacacctgta atcccaacac tctgggaggc cgaggcgggc agatcatttg  48600
aggtcaggag tttgagacca gcttggccaa catggtgaaa ccccatctct actaaaaata  48660
caaaaattaa ccaggctgca cacttgtaat cccagcttcc agctactcag gaagctgagg  48720
taggagaact gcttgaacct cggagatggg ggttgcagtg agccgagacg gcagcactgc  48780
cctccagccc gggcaacaga gcaagactct gtctcaaaat aaaataaaca aataaataaa  48840
taaataaata attgagatcc atggattgat gggtgtcagg atcctttgtg tgatacttta  48900
ctatcagttt gcaaaatatc accaatggga gaaactgggc agactgttca aggtagctgg  48960
ctgccttatt tcctagaact gcatgtgaat ctacaattat ttcaagaaga agtctttcca  49020
tttttgacga ggagaagaag gagtgatagc ggtgatgcat ttgttaggga gggtctggct  49080
ctgtctggag gtttgggggc aggcactgaa agccaccagc aggcaggcct tgcagacgcc  49140
ttccgctagt ggggagggac tgggagaggt tctgaagctt ccagaaaagg agggatgtgc  49200
cctgtccttc ccgttccctc cagcctcatc ttaaggacac agatctttgc ctggacccca  49260
gacgttttgc acactgttcc aggggggacag ggtgacccag ggaggggtgg ggtaaaggag  49320
tcctgagcac cccttggtgc agctgggagg agagggatga ggagggcagg tgaggcgtac  49380
cttggagaca gccgaggagc ccgaagatcc cgccacgcag ggctgcctgc gtctgctgcc  49440
cacctactgc agggtcgtcc gcccacaggc tcagccagta gccccggcag aaggaggcca  49500
cttgctggca gaggaagagg aagagtgcgt agaggcagag gggggtgccc acggcacgca  49560
ggtaggccag gtgcactgtg gccttcacct gtagcacaca tgagggagag ggaggcagag  49620
agagccccca gtgggagggg tgggttgagg caaggccagg cgaggctccc agaaaacatg  49680
cccatggcag atgggaccac cacgcagacc tcaccggttc tcccgctgtg cctcccacca  49740
ggagcaccat ttccccgaca ggccccagcc agccttagaa cccccatctc ctatacaatc  49800
cccagggagc tagtattaat attttttctt ttcttttttt ttttttgagg acagggtctt  49860
gctttgtcgc ccatgtcacc caggctggag tacactggca tgatcatggc tcactgcagc  49920
cttgaactcc taggctcaag taatcccccc gcctcagcct cccgagtagt caggactaga  49980
ggtttgtacc accatgtttt gttaattttc atagttttaa agagatggag tctcgctgtg  50040
ttgcccaggc tagtctcaga ctcctggcct caagcgatcc tccctcctcg gccttccaaa  50100
gtgcttggat tacaggtgtg agccaccaca cccagctaga agggttttct tgaacaccca  50160
ccataggtca ggcatgtgtc tctccttata acaacctcca tttcacagat aaggaaactg  50220
aggcacagag aggttcagcc actggcttaa ggtcctgctc ctacaaatct gaagttctct  50280
gcacagctgc agccaggcgg gactgttgaa aacattaatc taattatatc ttgtcgttgg  50340
cctgtccatg gctatctctt gctcttagaa gaaatcccag ccaggagggg tggctcatac  50400
ctgtaagcac tttgggaggc caaggcgggt gtgtcacctg agctcaggag tttgagacca  50460
gcctggacca acgtagtgaa accccgtctc tactaaaaat acaaaaatta gccacgtgtg  50520
gtggcaggca cctgtagtcc cagctactcg agaggctaag gcaagagaat cgtttgaagc  50580
caggaggtgg aggttgcagt gagctgagat tgcgccatta cactcttctc tgggcgacaa  50640
gagcgaaact ctgtctcaaa aaaaaaaaaa aaaaaaaaaa aaaaagaaag aaagaaagaa  50700
```

-continued

```
agaaagaaat tccaagcttc ttatctcgcc cccactcact gcctgccagc ctcatgggac  50760
ccctttctct ggcaccctaa gctacttccc acctcggagc cattgcacct gctgctctct  50820
ctgcctggag cgctctttct cctgcccttt gtatgattga ttccttcaca cattctttgg  50880
ggaagctcaa atgtcacttc tcagagcatc ctgtccatac caaccatggt atggtttctc  50940
agtggtctct atttcatcat tctttctttt aagaggcagg gtctcactct gtcacccagg  51000
ctggattgca gtgacatgat catagctcac tgcagcctcg aactcctggc ctcaagcaat  51060
cctcctgcct cagcctctga aagtgttggg attacaggca tgagccactg cgcctgatca  51120
ttcttatttt ctttatagca cttattgtta ttggacatag cttacttatt agcataatta  51180
tttactctcc gtctatcctc actagtgtct aatctctacc agacttagcc tggcacatag  51240
tgggtattgt gtacatgttt gctggatgga tgaggagggt aggtgggtga ataaatgagc  51300
gggtgggtag gtaggtaggt gtgtgaatga gtggatgaat ggatggaaag atcaatgaat  51360
ggatgaacag ctgaacagac agatgcatag gtgagggaat ggttggatgt attgttaggt  51420
gggatagatg gatgggtaag agaatgggat ggataaatga gtaggtgggt gagtggatgg  51480
gttggacaga taaatgagtg ggtgggatag atggataaat gagtggatgg gatggacaga  51540
taaatgagtg cctgggatgg atggataaat gagtgggtgg ggatggataa atgagttggt  51600
gggagggatg gataaatgac taggtgggat ggatggataa atgaatgggt gggtgggtgg  51660
catggataaa tgagtgggtg ggatggataa atgagtggtt gggtgggtgg gatggataaa  51720
taagtggatg ggatggataa atgggagggt gggatggata aatgagtagg tgggatgcat  51780
aaatgagtgg gatggataaa tgagtgggtg ggatggctaa atgagtggnn nnnnnnnnnn  51840
nnnnnnnnnn nnnnnnnnnn nnnnnnnnnn nnngtaggtg aatggatggg atggataaat  51900
gagtgggtgg gatggatagg tgggtgggtg gatgagcatc taggtggatg atggaatggg  51960
taagtaggtg ggtggagata catagcagta tagaagatga gaaacagtgt aagcttcaga  52020
ctcagattgg cctagatttg agtcccaggt tgtgtcccag gctagatatg aaaacacaaa  52080
caagtctctt aactctttaa gacttcagtt tcttggctgg gcacagtggc tcacacctgt  52140
aaccccagca ctttgggagg cagaggccag aggatcactt gagcccagga gttccagacc  52200
aacctgggca acatggcaaa acccatctct actgaaaata caaacattag ctgggcatgg  52260
tggcacacgc ctgtagtccc agctacttga gagactgagg taggaggatt gcttgagccc  52320
aggaggtcga ggctgccgtg agctatgatt acatcactgc ggtccagcct gggtgagtga  52380
gcgagccact ttctcaaaat caaaataaaa taaattttaa aagaattcag tttctttatg  52440
tctgaaatag acctatcata tctatttttt agggtggttg tgaggattaa gaaaatgaac  52500
atctagaatg ctactggcac atagtaggtg ctcaagaaag gtgagtatca ctgccaagtg  52560
ctacatttgg tgggaggact tgggcccctg gaggtggcac agtgggtggg gaggggtggg  52620
tgaagctggt ggttaccctg ccgtattgga tgctgtcctt tcctgctggc catcctgccc  52680
tgtcagggtc atccagagga acctctgtct gggcttctga agtggtacgg tccttctcag  52740
ggactgactt gatggacctg tcatttagag gaaatgaaga caaagtcagt atctctccca  52800
atggtggggt gtatgtgcct aaccctcagg cccactgaca gccactgagc tctgggtaca  52860
ctctgtactc tttcattcat tcatttatct aacagaatac tgaccagata tcacacttcc  52920
cttcttccca tatggtaccc agctaaatgc catctattac cccagggtca agcaagccca  52980
ttcttctgat gccaattcac aggatgaact taacttgccc accattggaa ctctgttctc  53040
```

-continued

```
agaattttct ttcttttttt tttttttttg agatggggtc ttgctgcatt gcccaggttg  53100
gtctcaaact cctgagctca agcaatccac ctgcctcagc ctcccaaagt gctgggatta  53160
caggcatgag ccaccatgcc cagcctgttc tcagaatttt tattttggct taagctttcg  53220
tgcaattgtt ttgttcctac tgtataccat cagatttgtc agtccaactg gcagaatata  53280
aattatgcac aattcagatg ctaaagactc tttgaatgtt ttatctgtgg atgagtaggc  53340
tgacttaacc tctgtgcctc agtttcctca gctgtaaaaa taggaatatt atctatctat  53400
ccatccatcc atttatccat tcatctacat acctgtatat ctacatatac atgtctacct  53460
accttctatt aaattgaggt tagcccaaag ctgcctcctt acatatttta agtttggcct  53520
aaaggtttc cccgtacata gtgaactgta acctaattgg actcaaacag actgcaacct  53580
actcctgtgt caatcactga gtttcagcca atcaaaggca accaaccgtt caaaccatgt  53640
tccaataaag caaacgctga gctgtaacca atccggctgt ttctgtacct cacttctgtt  53700
ttctgtcctt caccttcctt tttctgtcta ttaatctttg accccgtggc tgtaccagag  53760
cctctctgga cgtattctgg ttcagggact gcccgatgtg cggatcattc tttgcttagt  53820
taacctctgt tagccaggtg cagtggctca cgtgtgtaat cccagcactt tgggaggctg  53880
aggcaggtgg aacacctgaa gtcaggagtt tgagaccatc ctggacaaca tggcaaaacc  53940
ctgtctctac taaaaataca aaaattagcc gggcctggtc acatgtgcct gtagtcccag  54000
ctactcaaga gactgaggca tgagaatcgc ttgaacctgg gagacgggga ttgcagtgag  54060
ccgagattgt gccattgcac tccagcctgg gcgacagagc aagattctgt ctcaaacccc  54120
gcccccccg caaaaaacaa aaaacctcag acacattaaa tttgctagag gttaatttgg  54180
cacaatctcg gctcactgca acctccgcct ccgaggttca agtgattctc gtgcctcagc  54240
ctcccgagta gctgggacta caggcacatg ccaccacgcc ggcttttttt tttaaattta  54300
cttatttttt atttttagta gagacgggtt caccatgttg gccaggctgg tctcgaactc  54360
ctgacctcta gctagtgatc cacccgcttc agtttcccaa agtgctggga ttacaggtgt  54420
gagccaccgt gcccagcctt aatgtgtcta ctggttttct tttaacatga ctacctatcc  54480
atctgatctt acttcagatt cttgtgcgct gtgaaggtgg tgggatttct cagtgtgtgt  54540
gtgattgaga agtgccctca gggtggctag ctgggatggg ggtcagcccc aatggtccct  54600
ggggactgag gcccctcaag atcgctgccg cccaccaccc ctgtatagca ggcacttaag  54660
ctcaggccat ctggtatcag tggcctgttg ttctgcttcc caagacccct ctcattaaga  54720
ggggagagta tcaggcagca ggtccttctg ctgcagacag ctccacagtg aacccagctg  54780
tgtcctggct ggagggagct gagaaaagag gggaccggag gcctcctcct ggccccttgc  54840
ccacgtgttc tggccagcgt caagtgatgc tgtgcataca gacccaagcc ctgtgcatag  54900
ccagcctgtc aaagcataag tggccgggcc tggcatggtg gtttacagct atggggagga  54960
accagtcctg ccctactgca gcattcagac aactccagca agctggcctc ggcccacttg  55020
aagacatcca tcaattggaa ggcatattgt tcattccatg aactggcctt atgggggcct  55080
aatcatcttg gctaactgga ccaattttgg taaattatcc ctcagcaggg caccatgggg  55140
ggacttcagc aggttctcta tccataatgg ttttggttgc ccgcctaact gcccgagatg  55200
cgggtggtcc cttcagctac ttcagcttca gcctgtgccc ttctgagtgt ggcaccatgg  55260
tggactcacc tctcgcgtct aagctcgggc ctcctgcctg cagaggtgcc tctggggtcc  55320
ttggtgctgg tcccaggttc tgtttctgca aggtcaagag agtcctgtca cgcaacacgg  55380
cccagatacc cactttgaca cccactgact atgtggcctt aaccgctctg accatccatt  55440
```

-continued

```
tcccctgatc tggctcctgc cacgtctcca gcaacctctc tcaacacccc actctgagtt  55500
cttccaggaa catccttcag gcattcactc actcattcat ttcttcaatc agtgataact  55560
gagcacctac tatgaacttg aggttggaaa aacagcattt aacactgtac aaagtcaagt  55620
tacctctgtt tcccccaaca gccttgctca agcagttcct tgtgtctgga atgctctttt  55680
ctggctaact ctcacctacc ctcaggtacc atctccccta ggaaggacac ctccccacca  55740
ctatccccca ggtgtggcca gtaactgaaa gcaaatctgt agtagtttaa ccacagacct  55800
gtaagcaaca agtaactgct actgtaagct gctaggattt ggggggctat ttgttacaca  55860
gcatcatcac agcaaaagct gaccaacaca aacaggcaag ttctatcttc aagcttcagg  55920
actgtgacat tgtgaatcaa cacttaaggt tttaaccagg ttgggccagt gctaagcaga  55980
tgttctcaga agaagcaaag cctgagattg agggagacct ggatgtgaat ccttgctttg  56040
tcatgaaggg atagtgtaga gggtagcaat taaaaaacac attctctgga atcaagttgc  56100
ttgggttcaa atcccagtgc tgccacttac aagccatgta acctgggact agttccttaa  56160
cttctgggcc tcagtttcct catctgtgaa atggaaatga ttctagtacc agcctcacag  56220
gggcattatg ttgattaaat gagctaacct ctgtgatgtg ctgttagttg ctacttttca  56280
gtcattgtga gtgagcttgg cttggcaact ttacttccag aaccttgcca tgtatccagc  56340
acactgtttt tttggattat tagaaaccct agctagcatg gtgtagcttg ctaggcatca  56400
aagtccttct tgggctgtct ccatagcaac tgcaagcata gactctggag ctggacatac  56460
tcaagttcta atcttgtgac cttgggcaag tgatttaact ctctttgcct cagtttgctc  56520
atctgtaaaa tgacagcaat aacttcacat gcctctgggg catgtgtgag aatcaaatga  56580
aatagtgtat tttttacaga agcacttagc acaacccctg gctcatggat gatgttatcg  56640
gctattcttg gagaaaggtg acctattaag agagctgtct gcttccaggc ctaggcctgc  56700
agacagggtg tggccagagc actccattca tgccagtagg acccttcgag ccttttcccc  56760
caagggtggc aggagccagg cctggagaat cagcaaagcc cacctagtac ctccttctcc  56820
tctatctcct ggctgtctgg cttgatccag aagacacacg agggccccct tcctctgcag  56880
aagctcctgg taggaaccca tctctgcgat ggccccattt gccagcacta tgatccaatc  56940
agcctggggc aggatgtgga gtgcgtgcgt cacgagaatc cgtgtctggg cagggaaggg  57000
gtagaagtta cacacatgtg gccgggtgca gtggctcatg cctgtaatcc caacactttg  57060
ggaagccaaa gcatgtggat cacttgaggc cagaagttcg agaccagcct ggctgacacg  57120
gctaagccct atctctacta aaaatacaaa aattagctag gtgaggtggc gcacacctgt  57180
agtctcagct actttggagg ctaaggcaag agaatcactt aaacctggga ggtggagctt  57240
gcagtgaggc gagattggac cacagcactc catcctgggt gacagagcaa gactctgtca  57300
agaaaggaaa gaaagaaaga gaagaaaaga aagaagaaaa gaaaagaaac aaaggaagga  57360
aggaaagaga gagagagaga aagaaagaaa aaaaaaatgt acggccgagc gcagtggctc  57420
atgcctgtaa tcccagcact ttgggaggcc gaggcagatg gatcacctga ggtcaggagt  57480
tcgagaccag cctggccaac atggtgaaac cctttctcta ctaaaaatac aaaaaattag  57540
ctgggcgtgg tggcgggcac ctgtagtccc agctactcgg gaggctgagg caggagaatg  57600
gcgtgaaccc gggagccgga gcttccagtg agcggagatc gcaccactgc cctccagact  57660
gaaagacaga gcgagactcc atctcaaaaa aaaaagaaaa agaaaaaagt tacacacatg  57720
tgcttggcca gcctcctgag ctgggggttg gggtgggggt attgtccctg gactcagagt  57780
```

-continued

```
gggacagct ccccttcttg tgctcctgcc gcctttcttg taaacagcat atccaaatag  57840
agaaacagag gggactccct tagcctgtgt ctcaaaacaa gaagacaagg agtacatctg  57900
accctggcca atcatccaag gcaaagctgt agtagttaaa tcacagatcc ataaggaaga  57960
aacacctgct gttgtaagct gctgggatct gggggttgtt tgttacatag cattgtcaca  58020
gcaaaagctg accaatacaa agaggaaatt ggactcaagt ggaaggggga ggtgagataa  58080
acttgggtta ggactggatg ctaagtgctt cctctgcctt tgccctgtac tgtctgacac  58140
atgttcccaa acttactgtt ccctggagta gcccaccagg cccaatgacc tggttgaaga  58200
catgctggcc aacgtgggca tccagggccg ccagggggtc atccagcagg tacacagctg  58260
cctttctgta tacagcccgg gccaggctca gccgctgctt ctggcctccg gagagattca  58320
tgccctgtgg ccacaaaagg aacagtggcc tgagtcagca tctacagggt gaaactgggg  58380
tgcccaggct gtggcaggtc agggcacacc tgcccatcag ggtgaggtac agctcaacat  58440
gcctattccc tggggacagg cccagcttcc aaggcactcg ctctcaagcc aacaatgcct  58500
ccatccttac ccgacctcac ttctccactt cccaagcacg cttcctggag gagttaccta  58560
cacttcccaa tccactctgt ctcctcctgc tcactctctc tatctctttg agtccaactc  58620
ttgtttccct ttctccactg agaccaccat ccatttccct attccctcat ccagtggcag  58680
cttttcagtc ctacttttgt attttaaatt ttaattgttt tcttttagtt ttcattgata  58740
tgtaatagtt gtaactattc gaggggcaca agtggtattt ggatacctgt agggcagtgg  58800
tccccagcct tttggcacc agggaccagt tttgtagaag acgatttttc catggacctg  58860
ggggcagggg gatggtccgg gggatggttt caggacgatt caagcacatt acgttgattg  58920
tgcacttcta ttattattat tactgctgtt gtcgttgtta ttattgagat ggagttttgc  58980
tcttgtcacc caggctggga gtgcaatggc atgatcttga ctcactgcaa cctctgcctc  59040
ctgggttcaa gcaattctcc tgcctcagcc tcctgagtag ctggaattac aggcacccac  59100
taccacgcct ggctagtttc tgtattttta gtagagatgg ggtttcacca tggtggccag  59160
gctggtctcg aactcctgcc ctcaggtgat ccgcccacct tggcctccca aagtgctggg  59220
attacaggcg tgagccactg cgcccggcct acttgtatta ttattgcatt gtaatatata  59280
atgactcacc atcatgcagt atcagtggga gccctgagct tgttttcctg aaactagata  59340
gtcccttctg ggatgatgg gaggcagtga cagatcatca ggcattagat tctcataaga  59400
tccctcacat gtgcagttta cagtagggtt tgtgctccta tgagaatcta atgctgccac  59460
tgatctgaca ggaggtggag ctcaggcggt gatgggaaca ataaggaatg gctgtaaata  59520
cagatgaaac ctcactcgcc tgccctctgc ccacctcctg ctgtgctgcc tgcccagttc  59580
ctaacaggcc acagactggt gctgatccat ggcccggggg ttggggaccc ctgctgtaga  59640
caatatgtaa tgatcaaatc agggtaactg agatagtcat cacctcaaat atttatcttt  59700
tgtattgcga acacaaccat ccttctcttc tagctatctt gaaatataca agtaaatgat  59760
cattaactat aatttccctt gtgcactatt gattacttta acttattcct tctatctagg  59820
ccttcttgtc tttcattcat tcttttaaaa cttattttta tttatttttg agatggagtt  59880
ccactctgac acccaggctg gagtgcaatg gcttgatctc ggctcactgc aacctctgcc  59940
tactgggttc aagcgattct cctgcctcag cctcccaagt agctgggatt acaggtacgc  60000
caccatgcct ggctaatttt tgtattttta gtagagatgg ggcttcacca tgttggccag  60060
gctggtctca aactcctgac ctcaagcaac cctcccgcct tggcttccca aagtgctggg  60120
attacaggca tgagccaccg tacccagcca ttcattcatt cttacattca gtcattccac  60180
```

-continued

```
taataaccac tgcctcgtta tcataaacca ggcatggttc taggctctgg agaaacagca  60240
atgagcaaaa caaagttgct gctctcttaa tggatccatc attctcatga aggggacaga  60300
gacaggcaat ccataaacaa gtaaggcaga cagcacatca ggtggaaagt gctatgaaga  60360
ataaatagta aagcaggggg agccaggttc aggggctcac gcctgtaatc ccagcacttt  60420
gggaggcgga gctgggtgga tcacttgagg tcagaagttc aagaccagcc tggccaacat  60480
ggtgaaaccc catctctact aaaagtacaa aaaaaaatta gccagttgtg gtggtacatg  60540
gctgtaattc tagctactca tgaggctgag gtgggaggat tgcttgaact actcatgagg  60600
ctgaggtggg aggaatgctt gaactcagga ggtggaggtt acagtgagcc aagattgtgc  60660
cactgcactc cagcctgggc aacagagcga gactccgtct cagaaaaaaa aaaaaaaaaa  60720
gagaaaaagc aggtgcaggt gtagggtgca ctaacaatag tagggtggct gtggtggtag  60780
ataaggtggt caggaaaggc ctctctgtga aggtgataga agtgagggat gagccctggg  60840
gactcctggg gagagctttc cagcagaggg aacagcagtg caaaggccct ggggccagag  60900
tgtgctgtgg gggatcaggg aatatcacag agactaaggt ggctgcagta aagctgagag  60960
gtgatgatgg gagatggggc taatggatac cagagccagg tcacagggac cttgccaggg  61020
attgtcatga cttgggcttt gtctctgagg taaatgggga gatcacctga ggtccggagt  61080
ttgagaccag cctggccaac atggtgaaac cctgtctcta ctaaaaatat aaaaattagc  61140
caggtatggt ggcatgtgcc tgtaattcca gctactcagg aggctgaggt gtgagaattg  61200
cttgaacgtg ggaggcggag gttgcagtga gccgagattg catcactgca tgccagcctg  61260
tgcaacagag caagactctg tctccaaaac aaaacaaaaa acaaaaccac aagtggtggg  61320
ctggatttgg cttggggtca cagtttgcca acccctgccc aatccatagc tccagatgca  61380
tatatcctgt ttcttggaca tctctgtcca gacccccttgg tgaggcccag agaggggaag  61440
caattacacc aacattactc agcaaggcag ggcagagtaa gacaggagtc taggtcttct  61500
cactctcagt tgtcagagag ctcctcactg ccaatccctg ccacaactcc ctgcctctct  61560
ctttgtgtct atttctgctt atcaattagt gattacgtat tgagcaccta gcacgtgctt  61620
gacgctgagc tgagcccttt ttctccgcta cttccctaac cattcctctc atttctccat  61680
catactgccc atgatgagtc ggggacccaa atgactccca actgcaatgt ctccctgtcc  61740
caaaaagacc cccaaactct cacctgctcc ccaattgaag tgtggattcc ctcagggaag  61800
ctgtccacat ctggctgcag ggcacaggct tctagtactc tctccagcca gggtgggtcc  61860
agctcctgcc cgaagcacac attctctacc acagaggtgt tctgcaccca ggcctcctgg  61920
ggcacgtagg ccacagcacc ctaaaacaca acttactttg gtcacaggag gatgatgggg  61980
acagaggtgg gataggtttt gaggagcagt gggagctggg ctctcagtgg tgggtgagag  62040
gtggagagaa tgagtgaaag tgaacttggc tgggatgggg agggtgggaa ggcagcgagg  62100
aagtgggact ttcaggatgg ggacatccta gcagacaggc tgggggtggc ctcacctcga  62160
tgctcacgaa cccctccacc tttgacagct ccccaaggag ggcggacagc agggaggact  62220
tccctgcccc cactggaccg acaacagcca gcagacagcc ctggggcacc gtgaggttta  62280
ttctggacac gcaagagggg agacatgacc ttggttaggg ttcagcccgc ctctgtgagg  62340
aaggatgagc cccagacgga gctgagcttt cctgctctgg gagtctccaa gaggacctgt  62400
ggggctgttc tttttcccag tccttgtcta gctatttgag gaactatcct gtgcacatct  62460
gtgcatgtac acatgcacac aaagcgtgca cacatgcatg cacatttgca cactcataca  62520
```

-continued

```
agcatgctag catgcacagc aacacaatgt gggcacgcat ccacacacac acaagtgcat  62580
gcacataccc aatcaatcca tgctcacacg catacatgtg tgcacacatg cacaccacgc  62640
acacacacac agggttgact atagcctgag ggtttcacca gcctggcctc ctgccttggc  62700
tcttgcgata aataggctct ttcctccctc cctcccgcta ctcttggtcc cgccccactc  62760
ctgtccacgt cccacagccc atcctccacc cagtgaccag agggatctgt taaaacccaa  62820
gtcagatcgt gacacttccc agctaaaccc gccagcactc ccatttcact cagggtcaaa  62880
gctaaagtcc tgacgatcag gaatgacatc tcccgcctcc ttccgctctg tgcctcagct  62940
gctcggccct ggccttgctg acctccttgc tgtttcttga acacaaaagg ccagtggttc  63000
tcaccagggg gtgactgcat cccccaggag tcatttggca agatctagag atatttttgg  63060
atgtcacaac cagtaggggg tgctgctggc atctagtggg tagagactgg ggtcagctaa  63120
acatcccaca atgcacacga cagcccccaa caaaggagtt tcagcccaaa atatcaacca  63180
tgctgaggtt gagaaaccca ggtccaggca ctctcctgcc ccaggacctt tgctgatgcc  63240
attcccaccg cctagaaggt tcttctccca ggccgggcac ggtggctcat gcctgtaatc  63300
ctagtccttt gggaactgag gcaggtggat cacttgaggt caggagttgg agaccagcct  63360
gacgaacatg gtaaaaccca tctctactaa aaatacaaaa attagctggg tgtggtagca  63420
tgcgcctgta atcccagcta ctcgggaggc tgaggcagga gaattgcttg aatccggaag  63480
gtggaggttg cagtgagccg agatcatgcc attgcactcc agcccgcgtg atagagcaag  63540
actccgtttc aaaaaaaaaa aaaaaaaaaa aaaaaaaaga acagctcttc tcccagacac  63600
tccttcctta tgatctcggc ttgaatgcaa agccttccct cgctagacat gccatcgtac  63660
tctgttccct tgctctggtt ttctgtttgg gcctcacctc tatcagcatg tcaccccacg  63720
agagcagggc ccttgtctgt ttccttcgcc ctatccccaa tacctagaac agagcgtggc  63780
ccatacctag tgctctatcg atgaagtgag tgaatgacaa ccaatacaaa tactacctgg  63840
ggcatattcc ttctcttctt agggagtttc agggctgtct gagatttttg gccacaaaga  63900
ccaagcgata gagttggaga ctatagatga tcatgacctc ggactgatac aggaggcaca  63960
gaagtgagca cagctgatag ggctgaacct tggggctcct ctcagccagc cctcccttgg  64020
catcgtcttg gccagcctgg gagcacaggg gtgtctcccc ctaatggggg aggctcagat  64080
gccctggtcc ccgtctgcag gagatactgg tctatgctgt gcaggtcccc accttcagga  64140
ggtagagatg tatcctgaga acctccccgg cagagcccca gcccagccaa acccaccctc  64200
cagtcccagg ctggaaacct acaccacctc tcaggtggga ggcagcagga gccccatgca  64260
tcttctccct aaaaacatga ggctggttac tacgggtgtc gttctgtacc tgtggaggca  64320
gggagggctt tcctgggacc aggcgaaggt ggcactgtgt atggtgatgc aatccttccc  64380
ggcagctgca gggcacaaga ggccatttac aggagacccc tgacctggcc ggcctctgca  64440
tcggagaggc ccccaggcac catcccccgc ccccccagg ggcagaggct gcaggaagaa  64500
atctctccca ctgaacaaat tgccctgcta ctcactggct tgtgggtgac cccgcagggt  64560
tcttgttctg tccgtgtccc atggctacat aatccagggg gaggcaaact gtggcccaga  64620
gaccaaatcc tgcctgctgc cttttcttat aaataaagtt ttattggaac acggccacat  64680
ccattcattt ctctatttca tgctttgagc agttgtgaca gagactgtgt ggcccacagg  64740
cctaaaatat gcacaatctg gtcatttatg gaaaaagtta gtgaatttct gaaataaatt  64800
atcatcaaat cccagccttc ccagagtgaa gggggtgtta ttaatttcac tgtggccggc  64860
acagtgtctc atgcctgtaa tcccagcact ttaggaagca gaggtggtag gatcacttga  64920
```

-continued

```
ggtcaggagt ttgagaccag cctggccaac atggcaaaac cctgcctcta ccaaaaaata  64980
caaaaattag ccaggcgtgg tggtgggcgc ctgtaatcac agctacttga gaggctaagg  65040
caggagaatt gcttgaaccc aggaggcgga ggttgcagag aaccaagatt gcaccactgc  65100
actccagcct ggatgacgga gtaagactgt gtctcaaaaa tactactgct actactacta  65160
attattatta ttatttcact gtgataacaa gtgtaattag attagtggtt cttgatcctt  65220
aagacgtagt tagaattgcc tgaaagattt tctaaaaatc aaagctctca tggcttagcc  65280
cagatcaatt aaattcatcg tcacaattag ctgctataac gattaacatg cccattttgg  65340
agatgggaac acggaagctc agagagatga tctacttgtc aggatcaccc agctagtcag  65400
tgctggggct gggatttgga cctgggcagt tgaatgccac aggctcggct tcttaccact  65460
atgtgggtgt tttccaggta cacagtttgc ccaggttctt cagtgcaaca agggggaggg  65520
tgtcttggcc cgtggcataa aagaaggatg gggtggaggg ggaagcccag gtaacttgag  65580
cttggtaagt ctcatcgtgc aatggtgctt gaaatgctgc tattttccag cttgatcaaa  65640
atgctgtcat gcttattacc tgggactttc tgcatgagga caaggacctg gtctgttaga  65700
gcaggagtcc tcaaccccca ggccacagac tggtaccagt ctgcagcctc ttaggaactg  65760
ggccatacag caggaggtga gcgcagggca ggtgagcaga gtgtcatctg tgtttatagc  65820
cactccccat cactcccatc accgcctgag ctccacctcc tgccaaatca gcagcagcaa  65880
tagattctca aaggagcacg aacacttgtg aactgtgcat gtgaggaatc tgggttgcgt  65940
gttccttata agaatctaat gcctgatgat ctctgtctcc catcacccgc tttggggcca  66000
tctagttgac ggaaagcaag ctcagggctc ccactggttc tacgttatgg tgagttgtat  66060
aattatttca ttatatagta caatgtaata ataataaagg gcacaataaa tggaatgtgt  66120
ttgaatcatc ccaaaaccac gcgcctctcc ccggtccgtg ggaaaactgt cttccacaaa  66180
accagtccct ggtgccaaaa agcttgggga ccactgtgtt agagtgttcc ctgttgtaca  66240
cccaggatgg tacaaagtgg gcgctcagtc agtggtcgct gaatggctag cagaaagaag  66300
agcagcacgg tgccagtttc caagtgacac gcagatggcg tgatctgcac gtgtcatcca  66360
ttgcccgcag cccccatctc cccccagtac tgatgctggc ttgccattat gggccggggt  66420
ggcccccaca tcccccatcc ctcccacacc cctcctgcca gactcagcac tcaccgcttc  66480
cagaggaact tgagtctacg acaccagggt caacttcttc caggcagagg aaggtgacca  66540
gacggtcaaa ggacacccgg gcctaggaaa accgaagccg caggtcaccc agcaagaaga  66600
gcaaagaact caggttttgg gtgtcggtgt ctcaagatgt gtggcaacag cttcctgtct  66660
accaagctct gtgcatagga ggcgtgagga caaagctttc tagttcatgg gaaacgatgc  66720
aacccgagtg gtgaccttga tggtggtgat ctcccacctc tgcgatccta caaatcagtg  66780
acaccgaagc aagccagctg ccattctgca gacaagatct gggaagagga tggtggcttt  66840
tccaataagg ttatcaagcc attgtgtgga acaatttcaa atgttgtcca cctgggggcg  66900
ctctctccca gtcacaaacc catctttggg gaagaaagag accagtcgtt aaaatagaga  66960
ttaggccagg tgcagcggct catgccggta atcccagcac tttgggaagc caagtgcagg  67020
aggatcactt gaggccagga gttggagacc tggggaacat agcaagactc tttgtttcta  67080
caaaaaatta aaaaaattag ccggatgtgg tggcccatgc ctgtagtccc agctactcag  67140
gaggctggga ggtagaagca tcacttgagt ccaggagttt gagcatgcag tgagctgaga  67200
tcgtgccact gcactccagc ctgggtgaca gagtgagaca ctgtctcaat aaataaatta  67260
```

-continued

```
aataaataaa taaataaata aataaataaa taaataaggc ggccaggcgc ggtggctcat  67320
gcctgtaatc ctagcacttt gggaggctga ggcgggctta ttacatgagg tcgggggttc  67380
aagaccagcc tggcctggcc aacatggtga aaccctgtct ctactaaaaa cacaataaat  67440
aaataaataa gactgggtgc agtggctcat gtctgtaatc agcactttgg gaggccaagg  67500
tgggcagatc acctgaggtc agcggttcaa gacctgcctg gccaacatgg tgaaatctca  67560
tctctactaa aaatacaaaa aaaaaaaaaa aaattagctg ggcatggttg tgcatgcctg  67620
tggtcccagc tacttggcag gctggggcag gagaatcact tgaatctgcg aggtagatct  67680
tgcagtgagc cgagattgca ccactgcact ccagcctggg tgacagagtg agactccatc  67740
tcaaataaat aaataaataa aaataaaaaa taaaaaacat ggagatggct caggtatgcc  67800
gccgtttctt gttttcacca tgctgaaagg actagagata gcaaaggaag agaaacaaaa  67860
tcgctttgta taaaaaaggg aactgacatg attgcttgta tgtggaattg ctgggcagat  67920
ggacaagtat gcatgttctg aggtgtgtgt ggaaaggtct gcacattgcc ctccaaaggc  67980
tgaccccttc cagatgtatt tgctgtactc tctgcccgcc tctgttcttg cccctacccg  68040
cctcttttcc agctccacac catccctctc cctcccactc tgtcttccct ctcctctgca  68100
aatggcaggg gtagggaagc tggagccagg tgtagcccac gcactctccc aggatggctc  68160
cagcccttgc acccacctca cctggacgag ggagtggatg gagaagggca ggaaagcctg  68220
ggccttgttg aggatgttga gaactgtgag agtcacaaag gctttctctg cattcatagc  68280
attctcggcc accagagtgt ggacagcaaa caccaccagt gcgacctggg gggtgggggg  68340
gacacgtggg gcaacagtga gacacgcaag catggatagg gcagcctggg caagctgtgg  68400
tgcctgcacg gtccatgtgg cccacccgcc atgtccgcat gtgcttccct ccgtagatcc  68460
cactcccagt cctgctaaca catgtcctct ccgcagtcat aagctacata aggctctctc  68520
taaagacaca gcgcattgct aatggtgatg agtgcgcagc cccacggctc taggcatcac  68580
tagaacctag gggagaacct aatgcctcta ggttccaggc atcgggggac agcagagttt  68640
ttgatcttgg tagccctgtt gttctagacg tggtggaact tgtgattcta gagtcccttg  68700
gaagatgact ctaaagttgc aggcaggagc agcacttgag ggctctaggt gttggtgcca  68760
tttgtggtgc tttttttttt ttttttgaga tgaagtcttg ctctgtcgcc caggctggag  68820
tacagtggca tgatctcggc tcactgcaac ctctgcctcc tgggttcaag tgattctcct  68880
gcctcagact cccaagtagc tgggattaca ggcgcccgcc actgcaacca gctaattttt  68940
gtatttttag tagagacagg gtttcgccat gttggccagg ctggtcttga actcctgacc  69000
tcaggtgatc cacccacctc ggcctcccaa agtattggga cgacaggcat gagccaccac  69060
acccagccta cgtatcaaat tttttaaaac tgtggtttag gaaggttgtt ctgacagcaa  69120
tatgaaataa attacagaat ggcaggacaa ggatcacgtc cagtgacagg gtggctatgg  69180
acatctgctg gccaggatca gggaagtcac tctgacccag gattctacct ctgccacccc  69240
cctgcatctg taccctcctc cccacatcgg tagaagcctg gaactctctc tgagagttca  69300
gcagacttta tcagccactg ccacctttgc tagaataata tgattaatta gttcttgtag  69360
aagacagcag ggacccagag agaacaggat ccagaatgag tgggttttga tggacggggt  69420
ggtaggatct ggggggctcc acctacctca ccctgccccc acccccgcac tccttcccca  69480
gtgctgctca gcatagagac tagagtgacg tcaccagaaa tgtagacact tggaaggaca  69540
ccagcgacac agagaagagg aggccggagg tccgcaaggc gcccagctcc tggcctcgga  69600
tgcccaggac tctgtccaga aaggctccct cccagccatg gaacttgatg gtcttcgagt  69660
```

-continued

```
tcctgaggat agagctggtg agccgtgccc gtgagtcctt ctgcctcatt tgctcctcct  69720
gggatcggag ggaaaaagag agatgaagac agggacagtt gagaattctt ccctgcaccc  69780
tgacagccac ccttcagcaa atcccattca tctcaccaaa ctgcgtccca aacctgtctg  69840
cctctcagca cctctgaccc tcactcctgg tccaaccacc atcatcctgt acctggactt  69900
ctgcaggagt gcccctggga taatgtgccc cacggaggaa gcctctgatg cccggagaac  69960
agaggcagcc tgagcccacc tgggtatgac accatcagga aggctacctg gaggtggttg  70020
atgcctgagc tacgtctttt ttttttttta ccttttacat tttttgtgga gttggggtct  70080
cactatgttg cccaggttgg cctcgagctc ctgggctcaa gtgatcctct gccctcagcc  70140
tcctaaaatg ctgggattac agcctgagct aaatcttaaa tgaccaggaa gtgcgtgctg  70200
agcaggcaga ggatgggggg atggagctgg agaagaaggg aggggagggg cttgagatgg  70260
gggtgggggg tgggggctgg ggggtagggg ggtggcgggg gcagctaaaa cccaggcaca  70320
gggaatagca tgactcagag gacactcagt gtgaccagag gaccgtgtgg gcagggtcac  70380
ttggcacttt aaagtcaggc agaagaattc agggtctctt gtgcttcacc atggggcggg  70440
ggcatcatca gaggggcagc tgcctggaga aggttttact ttttgagacc gagtcttcct  70500
ctgtcgccca ggctggagtg cagtggtgtg gtctcggctc actgtaacct ccgcctcctg  70560
ggttcaagcg attctcctgc ctgagcctcc cgagtagctg ggattacagg cgcccgccac  70620
cacgcccggc taaattttat attttttgtg gaggcagggt tatgccatgt tggccaggct  70680
ggttttgaac tcctgacctc aggtgatctg cctgcctcgg cctcccaaag tgctgggatt  70740
acaggtgtgg cctcccaaag tgctgggatt acaggtgtca gccactgtgc ccagcctaga  70800
atgttttaga ggagtccacg caggaggctg aagaaacagc ccaggtgaca gacggacact  70860
gggacagctg ggccaagaga ggaaataagt tccttccctc catcccccat ctctccctct  70920
ctctttcccg ccttttcttt ccttccttcc ctatctcctt tcttcctctt tcctttgctt  70980
tcttccctct ttcatttcct tccctccctc ccccctttct tccttctctc cctcattcct  71040
tctcttcctc cctcaattct ttccttccct ccttccctct gtccttcctc cccttttccta  71100
tctttccttc cctccctcct tttctctcct tcccctccct tcttcctctc ctcctttcct  71160
tcttccctcc ctcctttctt ccatagttca caaacactta ctgagaacct tctgcctgcc  71220
aagcactaac tagatgccga gttggccaca atcagtggcc tgtgctgttg caaagcttcc  71280
agttaaggaa aacaaggcaa tcaaccctgc cgggtgcttc ctgtaggacc ctgtatgttg  71340
tgggaagtgc tgtgggggga aaaaagcaaa aacaatccca gggcaggcaa aggagaggct  71400
gctgctggga ggggagggat ggacgtgcca tttccttgct ggagggtggt gagggaagcc  71460
gccctgactg cagggaggtg acagaggatc ttcgggagtg agggtgatcc aggtggaggg  71520
aacagctaaa gcgaaggcct gcagggatgt gtgagatcgg gcaggtttga ggatgggaga  71580
tgtgtgggga aaggcaggga aggaggggag atgggtagaa ggtgaggttg gaagcaataa  71640
ggccagctca gggcgggcct ggtgggccac tgtggggtct ttggctcagt ctgaggaaaa  71700
tggggccgct gtgggtctga gtagaggagg ggtacaacgt atttggtttg cataggtctc  71760
ctctggctgg gagtggagag aggctgaggg cagaggcggg gagtgagcca ggggcttgct  71820
gctgtgacct gggttagaga tcatggggtt tggagagcct atgctgggaa gtgtgacatt  71880
ttggatgcat tttgaaggtg atgccaagca aatctgctga cagatgggat gtgagagaaa  71940
aaggcattga actgacccag ggcctgtggc ctgaacattg gagggacgga gccactgtcc  72000
```

-continued

```
attgagagga tagggggagg gggtgcaggt ctgagtgatg ggcagctcac agacgacaag  72060
aacaaagcca gacccgtggg ctcgcactca gctctcccct ccccatctcc cacaccagga  72120
cctgtggctt cctccctact tcctgcctgg tccgtccctt tcccaaaagc caaacctgat  72180
ggtggttcct tttcttggag atgaagaaat tcagagggag gaggctcagg aagacagcga  72240
tggcagtgag ggcggagggc cccaggagct ggggatagaa ggggcaggat gtcaggagat  72300
cccgaggagc ccagctctca gaggcacgtg aaccagagca actccatctt gaatagggac  72360
tgggtaaaat gaggctgaga cctactgggc tgcattccca gacggttagg gtattgtaag  72420
tcacaggatg agataggagg tcggcacaag atacaggtca caaagacctt cctgataaaa  72480
caggttgcag taaagaaggc ggccaaatcc caccaaaacc aagatggcta cgagagtgac  72540
ctcccgtcat cctcactgct acactccacc agcgccatga cagtttacaa atgccatggc  72600
aacatcagga agttacccta tatggtctaa gaaggaaagg catgaataat ccaccccttg  72660
tttagcatat catcaagaaa taaccataaa aatgggcaac cagcagccct ctgggttgct  72720
ctctctatgg agtagccatt cttttagatc tttactttac taaaaaactt gcttttggcc  72780
gggcacggtg gatcatgcct gtaataccag cactttggga ggccggaggc gggcagatca  72840
cctgaggtca ggagtttgag accagcctgg ccaacatagt gaaacacagt ctctactaaa  72900
aatataaaaa ctatccaggt gtggtggtgg gcacctgtga tcccagctac tcgagaggct  72960
gaggcaggag aatagcttga acccaggagg cggagcttac agtgagccac gatcgcacca  73020
ctgcactcca gcctgggtgg cagagtgaga ctccgtctca aaaaacaaac aaacaaacac  73080
ttgctttcac tttatggact cgccctgaat tctttcttgc acgagatcca agaaccctct  73140
tttgggatct ggatcaggac cccttttctg taacacagct gcagaccccg aaggtggtca  73200
gacttgggtc ctaagatggg gatgtcaggg aatctgataa gggcagccac caggtcccag  73260
ggatctgtgc tcatggggtc tgctgtgtca ggagatgcct gctgaaggtg gggtccttca  73320
atgtcaggga gggaaacagc cctcttacac gatagggaga gagttatatt caagacagat  73380
tgtgcacaca cacgagtggg actggggggt gttcccagcc acaacagtaa agttgagacc  73440
tatggaatca ggggacctgg ttcaaatcct gaccctgaga gttttgagtg tggccttggg  73500
gcaagtcatc tcccttaggt gcaattctct tgtctgcaaa atgggaatag agttgttctc  73560
atttggcatt ttctcttatt gcgtttaatt attttcctaa tcttcatttc atccctcgca  73620
agggttgtca gatttagtaa atcatcatac agaatgccca gttacatttg aagataaaga  73680
gtgaataagg ttttagtcta agtctcgtga aatatttggg acatacactg agaaattctt  73740
ccgtttgtct gaaactcaca cttcactgaa tgtcctgtgt tttctctggc aaccctgctc  73800
ccccaccaac gtggtgattt tgggatggtt atcttccccc tctcagcttt ggtttctata  73860
tctggaaaat gtggaagtgg ggggtagaat aaatgatttt taagttgctg tgactttctg  73920
agatttctgc acaggttatt tggacccatt ctcttgacaa gccccacccc aactccagtc  73980
tgtgtgcctc agtttcccgt ctcagtcctt aggaacacta tgtttattta tttatttatt  74040
tgtttgttta ttttgagatg gattcttgtt ctgtgaccca ggctggagtg cagtctcatg  74100
atcttggctc actgcaacct ctgcttccca agcgattctc ctgtctcagc ctcctgagta  74160
gctgggatta caggcatgtg tcactcggct aatttttgta tttttagtag agatggggtt  74220
tcaccacgtt gcccaggctg gtctcgaact cctggcctca agtgatccac ccacctcagc  74280
ctcccaaagt gctgatatta caggtttgag ccaccccacc tggcctggga acactatttt  74340
ctaacattgg gccagtttgt ttcatttatg cggcaatggc gctacctagt ggctcaatgg  74400
```

-continued

```
agaagggcgc agagggtaaa caccagccca cagcagggct tggaaaaaca ctcaaggaat  74460
gtgagcagaa gatgaacatc tctgtctggg ggaaaaatgg tatcattaaa ctgtagcaac  74520
ctcagtgtcc actcctcctt caccaagacc tcacggtgat gttaggaact gtctaccaag  74580
aggcaggtaa agtacacaag caaagtaaca tggtgcatta tctatggata tcttgttggt  74640
ctcatctaat ttttttttt ttttttttt tttttttaga aggagtctca ctctgtcgtc  74700
caggctgcag tgcagtgatg tgatctcagc tcactgcaac ctccacctcc cgggttcaag  74760
tgattctcct gcctcagcct ctctagtagc tgggattaca ggcacatgcc accatgcccg  74820
gctaattttt atattttcag tagagacagg gttttgccat gttggccagg ctggtcttga  74880
actcctgacc tcaagtgttc tgccggcctt cacctcccaa agtgctggga ttacaggcgt  74940
gagccaccgt gccccgcctg gtctcatctg atttttagca acggtggggt caacctgatc  75000
aattgccctg aattttccca cgttcttcct ctctccctct ctttcttcct aatgatgaca  75060
tttatgtact gcacatgaag ccctgtctga gtgccttatg ttgtaattgc taagcacctg  75120
cctattgttt gcaaggccct ggaatacaag gtgaagacac tggaaaaagt cctggcccct  75180
agccctagca aaaacaatca tatgcatgag cattcgagtt ttttttggaa tattcagcaa  75240
ttacaatcaa aatgccatta acagttttta caaggccagg cacagtggct catgcccgta  75300
atcccagcac tttgggaggc tgaggtgggc agatcacctg aggtcaggag ttcaggacca  75360
gcccagccaa catggtgaaa cccagtttct actaaaaata caaaaattag ccagatgtcg  75420
tggtgcacgc ctgtaatccc agctactcag gaggctgagg ctggataatt gcttgaacct  75480
gggaggtgga ggttgcagtg agccgaagtt gtgccattgc accaaagcct gggcaacaca  75540
gtgagactct gtctcaaaaa aaaaaaaaaa atcaaaagga tactatttca cgacatatga  75600
aaatgatatg cacttcaaat gtcagcatcc ataaatagag ttttattgga ggaataccat  75660
gcctgtttgc ttagtatggt ctacagccac ttctgcactc caagggcaga gatgaatatt  75720
tgcaggagag gtggtgtggc ctccagtgta aaaagcatct actgtcttat cctttatgga  75780
aaagtaacta atgataatat tacaaatacc tacagggtac agttgtgtgc ctggcaccct  75840
tttaagtgct ttctacatat gggctcgttt aatgcctcag cccctctggg gcaggagtgc  75900
tactgttaat tatgatcctc acgttggaga caagaacagg aggcacagag agagtagggt  75960
ccttgcacac agattcacaa ctgataagtg gtcagaagga ggatttgagc ctaggcagtt  76020
cccgatacag agtctaattt tatttttact tttatttatt tgttggagac agagtctcac  76080
tctgtcaccc aggctggagt gcagtggcat tatctcagct cactgcaact tccacctcca  76140
aggctcaagc gattctcctg cctcagcctc ctgagtggat ggggttatag gcacccacca  76200
ctatgcccgg ctaatttttg tatctttcag tagagacggg gttggccagg ctggtctgga  76260
actcctggcc tcaagtgatc cacctacctc accccccaaa ttgctgagat tataggcatg  76320
agccactgtg cctggcccag agtctgattt taattttaaa aaagaaaatc ctataccaca  76380
acgttaaagg aatgaagttg gaaagtaaat gttttgtttg ttttgtttgg ttgtttcctg  76440
atggctactt tgtgtttttt gaacactaag tagcaatttt tccccctaaa atgttctcct  76500
cttgtgtttt gtggacagtg gctatggtgg tgcctcaggg ttactggtaa cttcaaaaca  76560
tggttaactt gcctactggg taccctaata gcacatgggg aagtatcaac gtcatcatca  76620
tcatctttct acagaggaaa ctgaggccca gagagggtga acttcctgcc caaggtcaag  76680
tgaaggtcat ccttattgag gacttttccc atcgtatcag acaatagtag gcaaattgag  76740
```

-continued

```
acaggattgg aggaggagga gaaggaggag atgggggtgg aaggggagga gaaaaaggag  76800
gagaggaaga agaaagggaa gagaaggaga gggaagagca gagggaagag agggaggacg  76860
gtagaggaga agaagggaga agggaagaag tgggagggaa gatgacaggg agcagaaagg  76920
aagaagaagg tggagcagga gagaggaaga ggaggaggag ggggaaggag gaaaaggaag  76980
gggtgcagga agaggagggg gtgcgtgggc agaaggtggg agagatgcag gaggagggag  77040
ggtgcaggga ggggtgcaag aggaggaggg caggaggagg aggctggggc agagggagag  77100
gggaggaagc cttatgagct tctacaccag gaatggaatc cagggtgatg aaggcagaac  77160
aagggtaaaa cctttcatgt gcctctctga caccaacctg gttctcccac agcctcagac  77220
ttgccctaac cctggggtca cagcggacct cttccagcct cttgaatgct aagtcaggag  77280
gaggaagggt gggaggggga aggacgaggg ggagaaggag ggggtggggg actccgttca  77340
aatcccgtct tcctcctctg gcatacctgc cagagataga cgaagcagac cacgatccag  77400
acgagaggca gccacagccc gttgaggtag aggacgctct cggtcagccg ctgcacgtcc  77460
acggacacca gattgaccac atcacccacc gcactggcct ttctggagcc gctggacaga  77520
gccaggacct ggcgggtggg cagaaggaga gaagtaaagt ggggaggccg gggcagaggg  77580
atgccccagg tggcttctcc acccactgag ccccacctca cacgtctgcg aggtgggtga  77640
gtaaagtctc ttaggccaac ctctcagggc tctttgagga tccacagaga tgacaaaaat  77700
gaaaatcctc caagatccct aaagcacggg aggcataata atgaataaca tgcacgaaaa  77760
caccagatta acacagataa cggtggtcat ctgcccagtg ctcaccatgt cgcaggcact  77820
gtgctaaatg aacagcctta tcctttcccg gggtgctcac agccatgaat ggtaccaagc  77880
aggcactacc atattcattc cctctaatgc caggccaggt gcagtggcct ctgcctgtaa  77940
tcccgccact ctgggaggct gaggtgggag gattgcttga tcccaggagt tcgaaaccag  78000
cccgcgcgac atagtaagac ccaagctcta caaaatactt taaaaaatta gccagggggc  78060
cgggtgcggt gcctcacgtc tataatccca gcactttggg aggccgaggt ggacagatca  78120
cctgaggtca ggaggtggag accagcctgg ccaacatggt gaaaccctgt ctctaccaaa  78180
aatacaaaaa ttagccgggc atggtggcag gcacctgtaa tcccagctac ttgggaggct  78240
gaggcaagag aatcgcttaa acccaggagg cagaggttgc agtgagccca gatcaagcca  78300
ttgcattcca gtctgggcaa caagagcaaa atccatttcg ggggggaaaa aagaaaaaat  78360
tagccaggca tggttgtggt gcgcctgtgg tcctagctag ctactgggga ggctgaggtg  78420
ggaggattaa ttgagtacag gaggttgagg ctgcagtgag ccatgttggt gccactgcac  78480
tctagcctgg gcaacagagc aagaccctgt ctttaaaaaa aattctatgg ataaattgct  78540
ctctattatt ctctcaccaa ggaaaatacc acttccagtt aaattaagac atgtaagaga  78600
catctcgatt ttggaagtat tagagtgaaa aaaaaatgtg agacgagaat caatgaaatg  78660
aacatttact aaccccattc tatggctaaa gaaactgagg cagagagaag ttgagcaact  78720
tgcccaaagt cacaggcctt gtaagctcct acacaaggaa tggaatccag ggtgacgaag  78780
gcatgacaag ggtgagacct ttcatgtgct tctgtgacac caacctggtt ctctggcagc  78840
ctcacatctg ccttaaccct ggggtcacag tggacctctt ccagcctgtt gaatgctaaa  78900
ttccaaatgc agccctccct ttgtgactgc gtgagggtgt gaagaagtga tccaggaatg  78960
actggacata gaaattctcc acttagcaag tctttgaaga gtgctcactg tgtgactcac  79020
actgagctgg gaactgaaaa tacagctgtg aacaacagag atgaggcttg ctctcccggg  79080
cctggagttt gaggtgggga acaaggctct ataataaaga tttatataac tggccgggca  79140
```

-continued

```
cagtggctca cacctgtaat cccagcactt tgggaggctg aggcgggtgg attgcttgag  79200
gccgggagtt cgagatcagc ctggccaata tggcaaaacc ccatctctag taaaaataca  79260
aaaattaact gggcatgctg gtgggcacct gtaatcccag ctatttggga gggtgaggca  79320
ggacaattgc ttgaacccag gaggcagagg ttgcagtgag ccaagattgc accgctgcac  79380
tacagcctgg gtgacagagt gagactctgt ctcaaaaaaa taagacaaaa caaaaatatt  79440
tctaaaactc atgctttaat ggcagttatg atgagtaaca taaaaaagta gcccaggctg  79500
agcgcgttgg ctcatgtctg taatcccagc actttgggag gctgaggtgg gtggatcacc  79560
tgaggtcagg agttcgatac cagcttggcc aacatggtaa aaccctgtct actaaaaata  79620
caaaattagc cgggcatggt ggcgcacacc tgtaatccca gctactcagg aagctgagac  79680
aggagaatca cttgaaccca gggggcggag gttgtagtga gccgggactg tgccactgca  79740
ctccagcctg ggcaacaaga gcgaaactct gtcagaaaaa aaaaaaaaaa aaaaagccca  79800
gaggttagag aggagggatc tgatctcatc aggagatcaa agaaggcctc ctggcgtgtg  79860
ggtggggaat aggaagatca atgcctgctc accaggcggc cttcctctta ggctcaagga  79920
aatgtggact ctcaagacag gatagggcac acctagctct ggcatgctca ggggaacagg  79980
agcctgggat gcagcactct ggcaggaaag catcaagagc tgccctctcg gccacctagg  80040
agctgtcccc tctgtcccct cctcccctag gtgacagctc aggtgtcagg gaatgacact  80100
tacatgggac gggacctgcc ctggctcaga tgctccatac cccacaggag ccaatagctc  80160
ttggggcagc agtccaggga cttagcttcc agagtcccag gaacggacaa gagccactgc  80220
acagagagaa gtctaaagct atggcctcca accaggtatt cacagtcaat ggacagaact  80280
tccagcccag atgcaatttg ggtttttttg ttttgttttt tttttgttct gagacgaggt  80340
ctcgctctct tacccaggct gcgctgtagt ggcgtgatct cagttcactg caacctccac  80400
ctcccgggtt caagcgattc tcctgtgtca gcttcccaag tagctggaat tacaggcaca  80460
tgccaccatg cctggctaat tttgtatttt ttagtagaga tggggtttcg ccatgttggc  80520
caggctggtc ttgaactcct gacctcaagt gatccgcctg tctcagcctc ccaaattgct  80580
ggaattacag gcgtgcacca ctgtgcccag cctaggggtc atttttaccc caagcagtat  80640
tgtctgggaa cacagctgac aggccacctt atcagaaggt taatccttta tcctcaaggg  80700
ggaatgagtg gaagttaaaa tcaggctcaa aaattaaaat tagattgggg gagtagaagt  80760
ggtgcctaga cagtgagaac agctgcaaag gccccagggt gggtgggggc ctggagtgtt  80820
tgaggaactg aaaggagacc tgtgtggctg gaggagagtg agcatgggag gaggtgacgg  80880
gatgaggtca gagacaccct agggacagat cacacaagac cttacaggaa taactaagga  80940
gctgagacag atcacttgag gctaggagtt cgagaccagc ctgaccaaca tggcaaaacc  81000
ttgtctctac caaaaatata aaaattagct gggcgtggtg acacgtgtct atagtcccag  81060
ttactcagga ggctgaggca ggagaatcac ttgaacccgg gaggcggagg ttgcagtgag  81120
ccgagattgc accactgcac tccagcctgg gtgacagagc aagactccat ctcaaaaaaa  81180
taaatacata taatacagag aaataactaa ggaagtgaga atgtatggtg agtgactcta  81240
ataagcaagg actgaatgcg ttctcagctg ctgataacat tactgcccgc tcagtgatac  81300
tgcttttcct ggctgggaag acctgccctt gtcccccagg gctcaccttt ctgtacacca  81360
ggccagtgat ggccgaccgc aacctcatct gcagcacctt gagcctgtac atgttctgct  81420
gctcaaacag cgtttgcagg caggctgaga ggaacatcag cacggcgagg aggtagccct  81480
```

-continued

```
tccaggctgg aggcttggga tcaccaataa actccaggaa aaggcttgca ggggaaggag  81540
ggagaaggta cagctggtga gaggaggtgc ctaagggtgt tgcctttgcc caaaccagtc  81600
cagatgtgga ggatcagtcg gcccaaacta gtccaggtgt ggaggatcag tcagtgtggt  81660
tttttttgca ataatggtct ccgttatttc ccccactgtc catactcctt ttcaatctga  81720
ctgcagctcc tcaagatcaa gaggtggagt ttttgttccc acttgttata ggctaaattg  81780
tgtcctcaca aagtttatat gttgaagccc cgacccccag tacctctgaa tgtgactgta  81840
tttggaaata gggcctttaa agaggcaatg aagttaaaaa tgaggtcatt aggctgggcc  81900
ctaatccaat ctgactgggg tccttttaag aagaggaaat gtagacacac aaggagacac  81960
cagggggcgc aaacagaaga aagaccatat ggggacacag ggaggaggtg gccaactgca  82020
agccaaggac agaggcctca gatggaacca ccttgcagat actaatctcg aacttccagc  82080
tttgagaatc atgataaaat acatttctgt tgttcaagcc actcagtctc agtctgtgat  82140
gctttgttat gtcagctgag cagacaccac ttgaatctgg gctggctaca aaaccggctt  82200
tggccaacag agtacagtgg aggtaaagcc atgctggctc tgagcctagg cctcaagaga  82260
aaatgtggtt tttggtctat ttcttagaac cctcccaagc acccacatga acaagtctga  82320
gctagccttt tggaggatgg ggacccacat ggagcagaga cagccatccc agtctcagat  82380
acacaactgc aggcacatga gaaaacccag ccaagaaaag aaccaccacc cagctgagcc  82440
cagcccacat tactgaccca cattaccatg aactaaataa aagaatgttt gtcattttaa  82500
gccactcact tttggggcat tttacagcaa aaactaattg atgcagtcag gtaagagctt  82560
gcttatttgc ccttctgggg gtcagtcact ttctcattaa tccatttccc ttcctcagtg  82620
tccttctcac ccaccatcca gtgtcccgag caccagatgt ataggcagag gcaggagagc  82680
tgaagccccc tggccctgga aggatgccac taagagacca cccaccttag cagggcactt  82740
gaggtctggg actcacctga gcagcttggg gacagtgaac ctgaagacat cactgatgat  82800
gaggctgagg gtccccagga ggaaggtaga atggaacacc tgccagatgg ccttcagcag  82860
tgggcgccac tggctccctt cttgccgtag gaagggctcg gtctctggag ccttcatgcc  82920
actgccgcct ttccttttaa atgctattgc cttgttgtgc ctgaggggaa gggagagatt  82980
agctctgggt cccattttat actctcagcc gccagcggca gggccaggca ttaaagggtt  83040
gttttcccaa cagtggagat gggtgggtgt ggatctagcc tggctccctc acctgttcct  83100
ccttatcacc ctgagtaccc acttaagagg caatcatggg agttgggggg cagggcagga  83160
gggcactctg aggcctctta gatggccatg ggaaagcaca cctgttgagc acctactatg  83220
tgccaggcac tccccagtca tcctaagacc ccctgagaag ccaggtgttg ttcccatttc  83280
acagatgaga aaactggggc tcagagaagc gaacttgccc aagggcacac agctgagaag  83340
taaaagaact ggaatttgat tccagctctc tgcctccaga gcccatgcac ttttcttttt  83400
tcttttcctt tttttttttt tgagacgaag tcttgctctg tcgcccaggc tggagtgcag  83460
tggtgtgatc tcagctcacg gcaacctcca cttcccagtt caagtgattg tcccacctca  83520
gcctctcgag tagctgggat tacaggcaag tgccaccata cccagctaat ttttgtattt  83580
tcagtagaga aggggttatg ccatgttggc caggttggtt ttgaactcct gacctgaggt  83640
gatctgctcg ccttggcctc ccaaagtgct gggattacag atgtgagcca ccacacctgg  83700
cctctcatgt acttttcaac ctatcgtgtt gtcaacctgg aggaagaaca gcaccccgtc  83760
cccaacacac acaatcatcc agcccttagg tggttttgaa ctggtggaga atcacggctg  83820
atgggcatgg ggcctggtgc tctagctctg ggtgaaagtg cagacagaag ctcaggctgc  83880
```

-continued

```
ctcaaactaa taagatcccc agcctttggc tataaccagg ggccacagag aagagctaag  83940
gtgagggagg gagaggagga gatgggggag gcccgagggc ccctgtgagg caggtcagaa  84000
gccctgggcc agaaaggaga ggctggggcg atgcagctgc tgacagtccg gttgctgtgt  84060
ggtcctgggc ggggacactg ctcctctctc tgtgtgtgag aggatgggtg tggtcccctg  84120
ctgagtcccc tgtggctctg acaacctata aggttatcag taatttcttt ttctttttct  84180
tttctttttt tttttttttt gagacagagt ttcgctcttg tcgcccaggc tggagtgcag  84240
tgtagcaatc tcggctcacc gcaacctctg cctcctgggt tcaagcaatt ctcctgcctc  84300
agcctcccaa gtagctggga ttacaggcac acaccaccat gcctggctaa tttttgtatt  84360
tttggtagag acagggtttc acaacgttag ccaggctggt cttaaactcc tgacctcagg  84420
tgatccacct gcctcggcct cccaaagtgc tgggattaca ggtgtgagcc accatgcccg  84480
gccacttatc agtaatttca atccccatta cagatctgtg acccggggcc acgtgctggg  84540
atcagctctt tacacgaagg agctcactga ctcccctgga tccccttgcc aggtgagcat  84600
tattaggttt tccattttac agaaggggaa gctgaggctc tgagagatgg cgacagccgc  84660
ccgaggtcac acagcaaggg cagagcaggg atttgagcct agatcttgat ttatggtttg  84720
taaagggttt cttgtgcact aaggaccccc aacctcacca taataaaata ataataaaaa  84780
aagaagcata agaaaaacct ctggtgagct caggtggcca gacccttcaa ggccaaggtc  84840
tctgtcccac attattggtc tgatctggtg tttggtttgg catctatgga gggttgtggt  84900
tcagctctgt tactgagtgg gtgtggcctg ctgctcacaa atattttggc atttggatct  84960
caaagccaag aagatgcccc ttccatacag agagcatccc tgcccaccct ttcctgtttg  85020
atcctgccat ttaattcatt gccttcacag ccatgtccat ggctccaacc ctctctttgt  85080
ctcgttagaa ccccaggtgg gtagactttg cctgtgtttt ccaccaagat gtccctagta  85140
tagagtccag ctcctgcaca cagtaggagc tcaataaaca cttgtcaaat gaatgggaaa  85200
aacagattga gtgatgtgtg caaagggcct aataagagtg ccccctgcac atactgttat  85260
aaaaatttat agaaggaagg aaggagcttg gctgggtgga cagaacttgg ctttggagcc  85320
aggagactgt ggttccaatg cctgctctgt ctcctctcct ctgagcctta gtgtttccat  85380
ctgcaaaatg gggtcgggga agagttcact ggaaagtttt ctttctggct gaggttctgc  85440
tcagttctat ttgagctgtt taacccagag agtcagtgtg ttcagcctgc aggctccata  85500
gcaagtgttt tcctctcctg caggtctcac ctcccatcaa ggaagatgtc cagattgctg  85560
tctgacgtct ggtctctgga ctgaaggcca tttagtgcag atctcacaaa tgatggtggg  85620
gcaaggcagg gggtatgcat gagtggcatg ggcaaggtgt gagttggggg atacaaaagg  85680
gagtggtgga ggccgggcac ggtggctcac acctgtaatc ccagcacttt gggaggccaa  85740
tgcgggcgaa tcacctgagg tcaggagttc agggccagtc tgatagcctg agcaacatgg  85800
agaaaccccg cctctaataa aaaatacaaa aattagtgaa gccgactgga ccagcaggtg  85860
gctgttgtgt ggcctctcag gaggacgccc tctcccttcc cccagtggtt gcaaaatact  85920
tcagaaagaa aaccaaagtt ctctgtgggt gcagtcggtt gtttcagaag ctgacggagc  85980
ctggtctttg tataacccca tctttcccct ttctttctgt caactgttta tgggaggatt  86040
ctcaaactgt tctggagaat gtttctaccc tttagttcta gtgttgggtg acctgtaatt  86100
ttcatgttgg ctggggatgc caggagttgg cagaggctcc ttccagagcc cctgtggact  86160
ggattctgcc acttccgtaa aatcattcaa aagtagaggg tgagtcaggt gcagtagctc  86220
```

-continued

```
acatctgtaa tcccagcacc ttgagaggcc aaggcaggca gatcccctga ggtcaggagt  86280
tcaagatcac cctggccaac atggtgagac cctgtctcta ctaaaaaaaa tttaaaaatc  86340
agctagatgt ggtggcacac gcctgtggtc ccagctactc agaaggctga ggcaggagaa  86400
ttgcttgaac ccaggaggtg gaggttgcag tgagctgaga tcataccaca acccagtgaa  86460
gggggtccag caagccatgc ctggggtgag agagaactga tgttttggtt ctctcacact  86520
acttattctg tttggaaaaa cacatgccct tcctttgtgg gaacagcccc tacccacttc  86580
tgtggctctg aagggaccac cagtcatggc accagccccc tgggcatggg attggcccct  86640
gacaggcaca tgacttgagc caggccaatt agaggccttc cttgggattt actatatgga  86700
cgttaggaga gagatgctct cttattctgc tggagtttgc tgaacttgca tgggaaggga  86760
taggccttat ggagagacca acacatagat aatagttggg atgggagatg aaaggagaga  86820
atcctgacat catttgagtc ccctgatcca gcaacacctg aggctagatc ctcttagctg  86880
tgtgagccta tagtatcagt ctctgtctcc tctgtctctc ttaatgtgtg ggattcagcc  86940
atctgcaaca actaccacaa aatcccggag tatgcaggga acttcccaca gagctaactt  87000
ccttttttgt tctgtctcct aaaacaccaa gatccggtga ggttaagcaa cgtgtccaag  87060
gtcatcacta tttgaaggca gggcagcatt taacccaatt ttatctaatc ctatgcaggc  87120
tcatttatct agaccagagt ttctcaaatg aggcatccca ggctctaagg gctgcagaga  87180
agtttccaga gatgccactg agggcaggag tggacagagt ggataactcc aaagatctta  87240
acaccctctg gatgactaac agtgcttgag cacttcccat ttgcaagaca tttgcaagtt  87300
cttttccata aatcatcctt tttttcatc  cccataagct atgagctggg gctaatgaca  87360
tccccactga acagatgaga aaactgaggc ccaggaaagg aattgctcag gttatatagt  87420
aagtgagcag ctgcttgtgt gttgagtcac ctcccaaccc tccaccccgg ccttaaaata  87480
cctcttctgt ttgctgcctg tcattctgcc atttccccat ttgtaggaac ctgtttgttc  87540
cccgtttgta ggaacctgtg atgcgttctg ggaggaacca tatcttaagc ctgatactac  87600
ttagtgggat cagctggaag gcaaggtggg gaggcggcag tgccgccaga gtagcgttgg  87660
gggctggact gggggtcaaa tgatgaggtt tttttgtttt tgtttttgtt tttgtcttgt  87720
ttgtttgttt tttttttga  tacggagtct ggccctgtca ctcaggctgg agtgcaatgg  87780
tgacatctcc actcactgca acctctgcct cctgggttca aacgattctc ctgcctcaag  87840
cctcctgagt agctgggatt ataggtgcct accaccacgc ccagctaatt tttctatttt  87900
tagcagagat ggggtttcac tatgttggcc agattggtct tgaactcctg accttgtgat  87960
ccgcctgcct cggcctccca aaatgccggg attacagtcg tgagccaccg cacccggcca  88020
atgatgagct tttctgaagt agcatcaggt gagttcttga cctccaccca cttacctccg  88080
ggctgcactg cggttcctca tccactcctt ttcaagccgg gaaacaagtt cttctgagga  88140
gttttctctc ccaagcgacc agaggtcttt tggtctcagt ggcctcctgt atcccctcca  88200
gaccaggctg caaaagaggg gcaccaggga aagcttttcc tgccattcac ccctgcagga  88260
tcctggccag gcgagtagct gtgtgaccct gggtaagtca ctttacctct ctgtacctct  88320
actggcccct gggtaaaaag aaagcaattc actaacccca cctaatgtct gcagggcatt  88380
tctcgtttca caaagattgt ctcattaatt cttacatgaa cccataaggt aggttattat  88440
tgtttgtttg agatggagtc ttgttctgtc tcccaggctg gagtgcagtg gtgcaatctc  88500
ggctcactgc aacctccacc tcccaggttc aagcgattct cccacctcag cctcctgagt  88560
agctgggatt acaggcaccc accaccatac ccggctaatt tttgtatttt ttgtagagat  88620
```

```
ggagtttcac catgttggcc agactggtct cgaactcctg acctcaggtg atccacctgc  88680
ctcagcctcc caaagtgctg ggattacagg catgagccac cacacccagc ctgtaaattg  88740
atagtttata attgtataaa tgtatgagta tattattata gatctatttt acagatgggg  88800
aaggaaatag aagtgcagag agattcagtg gctaaaccaa gggatagccc ttggcaaggg  88860
aaacagacat ttccctggga atcagaagtc cgttgaccaa aactatcatt gtagaagaag  88920
cttgaactcc tccctcagct tttttttttt aattattatt attttttttg agatggagtc  88980
tcactctgtt gcctaggctg gagtgcactg atgtgatctg ggctcactgc aacctccgcc  89040
tccctggctc aagcgattct cacgcctcag ccttctgagt agttgaaatt acaagccacc  89100
atcacacctg gctaattttt gtgtttttgg atggtgtatc accatgctgg ccaggctggt  89160
ctcgacctac tggcctcaag caatcctccc acctcagcct cccaaagtgc taggactaca  89220
ggcgtaagcc accacacctg gctaattttt ttgtttatag tagagatggg atttcgccat  89280
gttggccagg ctggtctcga actcccggcc tcaagtgatc tgtcagggtt ggccttccaa  89340
agtgttggga ttatgggtgt gagccactgt gcctggcctc aggtctcttt aatctttctg  89400
atgacaccag ccagaaggtc ttgcctggtt ctggtctctg actcttctct aagccttacc  89460
aagttccctt ttctttttta tttttattct ttttattttt ttgagatgga atctcactct  89520
gttgctcagg ctggagtgca ctggtgtgat ctcggctcac cgcaacctcc acctcctggg  89580
ttcaagtgat tctcctgcct cagcctcctg agtgactggg attgcaggct cccaccacca  89640
cacctggcta atttttatat ttttagtaga gatggggttt caccatgttg gtcaggctgg  89700
tctcgaaatc ctgacctcag gtgatccacc tgcctcagcc tcccaaggtg ttgggattat  89760
aggcgtgagc cactgcgcca ggccaccaag ttccctttc taatgcagag ccaacttggg  89820
gaagcaaccg ttctgacata gaaattatta acgtggcttg attttccctg aaattatttt  89880
tggagttctc ctatatggca agtgatgcta tagatttttc ctattttagc agtgatagag  89940
agtttctttt taaaaacagt ttattcgagt aaaaaaagtg actcaattta gtttttgccc  90000
cagtaggaca aaaaagcatc aagagtggtc cataaatgct taagtttggg aagcaggggc  90060
tggacccccc agtagagctg tttcgaaaac ctctaagctc tttctaccag ttccacacat  90120
tcaaagcctg atatttttca tttatttaat agccatttag gccgggtgcg gtggcttatg  90180
cctgtaatcc cagcactttg ggaggtcgag tggggtagat cacttgaggt caggagtttg  90240
agaccagctt ggccaacgtg gtgaaacccg gtctctacaa aaaactacaa aaattagctg  90300
ggcatgatgg caggcgcctg taatcccagc tgctcgggag gctgaggcag gagaattgct  90360
tgaacctggg aggtggaggt tgcagtgagc tgagattgtg ccattgcact gcagcctggg  90420
caacaagagt gaaactctgt ctcaaaaaaa aaaagagaaa atgaatagcc caggcacagt  90480
gggtcacacc tgtaatccca gcactttggg aagccgaggc gggcagatca cctgaggtcg  90540
ggagtttcag atcagcctga ccaacatgga gaaacactgt ctctactaaa aatacaaaat  90600
tagccgagca tagtggtgca tgcctgtaat ctcagctact cgggaggctg aggcaggaga  90660
atcgcttgaa cccaggaggc ggaggttgca gtgagccaag atagtgccat tgtactccag  90720
cctgggcaac aagaacggaa ctccatctca aaagaaaaaa aaataattac cacttaaact  90780
cattatttgc caggccctgt tctaagtgct ttacagatct catcttattt aagcttcaca  90840
accctatgag ctaagtgcta ctatcaatcc cattttgaag gagtggagac tgaggcacag  90900
agaggttaag taactgtcca aagcaacaca gctaggaagt ggtagggcca ggattcaaat  90960
```

-continued

```
ccatatgtca ggtgctactg aggtctgaat gccgtgtggt taggagagag cacatcctca  91020
agtgccttgt gagctggccc tggagaagca gctgttttct caatctgcct ggaaccctct  91080
agaaagtaga cacttgctcc tttatctcct cacccctggg gcttagcaca tagtaggtgc  91140
ctattaaatg ttggtggaat gactgaaatc aagtattgga gacaattcta attactatta  91200
agcacccgct gtgtgcaagc actaagcact ttccgtctca tgcaggttga gtcatcccca  91260
ttttacagag ggaaaactga gactccggag gtttgcgaca tggcctgcta acaggcagag  91320
ccgggattca aatcaagatc tcactccagt gagtgaatgg gaacaggatg cagatggtag  91380
acactgaaca cgaagaagaa agcactgagg ctgggatgga gaaagacttg ctggcctttg  91440
taagcacagg ggaagggcca tggctgggaa tcagagcagc aaatgcaggc gggtgaggca  91500
ccaccccaac ccttccgtgc gactttactt acccagaaac ccaccagaac gtggctttgg  91560
aggggaaggc tgccccagtc tctggacagg ggttctgcaa cagacaaaaa tggagaaggg  91620
aagtatgtgg caagggtagg aagacaggac gaactgtgta tttttttttt tttcgagaca  91680
ggttttcgct ctgttgccca ggccagagta cagcggtgtg atcttggctc actactacct  91740
ctgcctcctg ggttcaagcg attctcctgc ctcagccttc caaagagctg ggatgacagg  91800
tgtgcgccac cacacacagc taattttttg tgtttttagt agagacaggg tttcaccatg  91860
ttggccaggc tggtctcaaa ctcctaacct caagtgatct gcctatctcg gcctcccaaa  91920
gtgctgggat tacaggcatg agccactaca cccagccctg acggtgtatt tagtactgaa  91980
agtaaacatc gaggtgccct gtctccttgc caggggtgta gaccagtgag cttggtgctt  92040
cccagcaggc agcgtaaaaa gaggttgggc cacaggcctg acaatgtcca caaggtaaga  92100
aataacagtg gctcagaaga acaactatga ttatactgaa accaaaacct tgctttgctt  92160
ctcaaaagga aggacactgc ataacgaaga aattagatcc ttgacaatat ccctcggcaa  92220
atgttgtgaa gacagacctg tcgtgcgatt tttgtcaggt gctccaggaa gattacaaca  92280
gtctgtactc tttaccaata aggcgtgaag gtgcccattt caccacgttt ttgccatcac  92340
agcttattaa tttttaaatt ttgttgctac tctggtaggt acaaaaaaga ttcctatgat  92400
agttttaact attctcaagc cttcgagcaa tttttttttt tttttttttt tgaatacagg  92460
gtctcgctct gtcacccagg ctggagtgca atggtgcaat catagctcac tgcagccttt  92520
atctcttgga ttcaagcaat cctcctgctt tagtctccac agagctactc tgtagtggga  92580
ctacaggcat gcaccaccac actaggctat ttttaaaaac ctttttgtag agatggggtc  92640
tcactacatt gcctagtctg atctagaaca cctgggcaca aacaatcctc cttcctcggt  92700
ctcccaaagt gttgagatta caggcatgat ccactgcatc tggccccatt tgaacatctg  92760
tttatatgat gtcagatcag tctcttccac aaaagaattg tttcttgatt tcacagactg  92820
cttcactgtt acctattgta aatctctcaa tctctcatga gcttcttcta tggagcactt  92880
accccaaggg taattttctt tttccttctt tttttttttt ttttttttgg tggagttccg  92940
ctcttgttgc ccaggctgga gtgcaaatgc acagtcttgg ctccctgcaa cctccacatc  93000
ccggattcaa gcaattctcc tgcctcagcc tcccgagtag ctgggattac aggcgtgcac  93060
caccatgcct ggctaatttt tgtaatttta gaagagatga ggctttacca tgttggccag  93120
gctggctttg aactctcgac ctcaagtgat ccacctgcct tggcctccca aagtgttggg  93180
attacaggca tgagccactg tgaccatcca attttcaaca tatttgttta attttgtgac  93240
cagtgtctgg ttcccctgct tgaccagtag ctacgtgaga acagaaactc tatctgcttg  93300
ttcaccatag atccttatgc ccttgctagg gcatagcggg gtttggcaaa ctatgaccaa  93360
```

-continued

```
atctggccca ctgcctgttt ctgcaaatag tgttattgca acacagccat gcaatttgtt  93420
gacatattct gcttttgcgt tcaatggcag agttgagtaa ttgccactga gatcactgta  93480
tggctcacag agtccaaaat attttctctt ggcccatata gaaaaagtct gccaactgtg  93540
gcatcgagta gaaatgtggt acactttttg ctgaatggct aaatgaataa aaaaattaaa  93600
gacttttggt cacctggggg agactgagac ctcaaagtgg aacaggaatg aggttggaac  93660
ttggtgactt acagactgct gggggtcttc agggaagaag gggggttgat ccgccaggca  93720
ggacagcaca aactgtgcca ccaccagaga caggcatagg taggtggaca ggtggcggac  93780
agggtcgctc tggaagccct gtgggaggga aagcagaaga taaggaatgg agacagagga  93840
gggtgctcag aggagagaaa aggtttctga tcttgggtca gtgcccactc tggggaccag  93900
ggcaagagta tttgaaagcc agagccctgg ctttcctagt ggttctaatt ttctttcttt  93960
cttttttttt taagacaaag tctcacttgg tcgcccaggc tgaagtgcag tggcatgatc  94020
tcggctccct gcaacctctg cctcctgggt tcaagtgatt ctcctgcttc tgcctcctta  94080
gtagttggga ttacaggtgc ccaccaccat gcctggctaa ctttttaaa atatttttag  94140
tagagatggg gttttgccat gttggctagg ctgacctcaa actgctgacc taaagtgatc  94200
tgcctgcctt ggcctcccaa agtgttggga ttacaggcat gagccaccat gcccagcagg  94260
tcctaatttt caaataccca atttataata ttctgtctat acaaatggtg ggccagggct  94320
gcgtctgggt tttgtcctta gccacatgat gattggccac agctgctggg acaatgagat  94380
gaagaaacaa tttaccttct tctttgtgcc acaaaagaaa tcctttctcc gttccaccct  94440
ctaccccaat cttcaaccct gctccccctt ggccagggtt ctctggtttg cagagatgag  94500
agctggtttt attgagcact gaccctgccc tgagcacatg cggcattctt gccatacaca  94560
gtctcatcag ctggagttta cttgcttcct ttgactcagg gggaaaccaa ggctcagaga  94620
agtgacagca ccttgttcaa ggacacgcag atgatctggt ccaaattgtg atgctcctgc  94680
tgccacacca caatgatttt tgcatctgct gccctgtcat ctggtcagaa acaccctaat  94740
tttctttctt tttttaattt aaagcatttt ttattttttta attttaggtg tgtgtgtgtg  94800
tgtgtgtgtg tgtgtgtgtg tgtatacttt tttttttttt gagacggagt cttgctttgt  94860
cacccaggct gatgtgcagt ggcatgatct tggctcactg caccctccgc ctcctgggtt  94920
caagcgattc tcctgcctta gcctcctgag tagctgggat tacaggcatg tgccacgacc  94980
cctggctaat tttgtattt ttagtagaga tggagtttta ccatgtaggc caggctggtc  95040
ttgaactcct gacctcaggt gatccgcctg ccttggcctc ccaaagtgct gggattacag  95100
gcatgagcca ccgcgcccgg cctgatatat atatttctgg atgacgtgag atattttgat  95160
acaggcatgc aatgcataat aatcacatca aggtaaatga ggtctccatc cccgcaatca  95220
tttatccttt ctgttacaaa tgatccattc tactcttgta gttattttat tttttagttt  95280
attattgagt tggagtctca ctctgttgcc caggctggag tgcagtggct tgattttggc  95340
tcactgcaac ctccgtctcc tggattcaag tgattctcct gccttagcct cctgagtatc  95400
tgagattaca gatgtgtgcc agcacgcctg gctacttttt ttgtattttt agtagagaca  95460
gggtttcacc atgttgccca tgctggtctt gaactcctga cctcagatga tcctcctgcc  95520
ttggcctccc aaagtgctgg aattacaggt gtgagccact gtgtccagcc tcttttagtt  95580
attttaaaat gtacaattaa attattattg actatagtca ccctgttgtg ctatcaaata  95640
gatattattc tttctgtttt tttgtaccca ttaaccatcc ccatttcccc cacccactgt  95700
```

-continued

```
ccttcctagc ctctagtaac cttccatcta ctctatatgt tcatgagtta cattgtttta  95760
atttttagct ttcacaaata agtgagaata tgtaaagttt gtctttctgt gcctggctta  95820
tttcacttaa catccatgtt gttgaaaatg acagtacctc attctttttt atggctgcat  95880
agtacttcat tgtgtatata taccacattt tctttatcag ttcgtctgtt gatggacact  95940
taggttgctt ccaaatcttg tttattgtga acagtgctgt aataatcatg ggagtgcaga  96000
gatctcttcc atgtactgat tttctttctt cctaagtttt ttgcttgtgt tcgggcgtgt  96060
gatttgtgca gaactgactc tactccgagg ctgggtgggt gaatgaggcc tggccaacga  96120
atacgttctg gtcttttggc taccatggca gggttaggaa tgcacatagc accccatgct  96180
gggtacttga gagctggaac catcgggaga ttctgctggc tttgctacat gctagaatgt  96240
aagtgtgaag gtattggtgg ctcttcttgc cactccattg gagaatcaag ctaacatggc  96300
agagccaaga ggcagaagtg gagatctggt gatggtacct ggtcccaggc ctggatcagt  96360
catgcctggg agatcccatg ggtatgagct aataaatgca tgagctaatg aaccccccttg  96420
acttaccctt ttcattaagc tagtgtgaac tgaggtttta tggctttaaa ccagagccct  96480
agttttaaat catgattcct ctactggatt ttatactctt ctagttttgg gtttttgttt  96540
gtttgtttgt tttttggcag atagcagaca attggatatt ccaatgacaa tatggcccat  96600
cttccctaaa ctcccactgt tttccccact gtttctctca gaaagtttgt tctgaatttg  96660
cctgagatga actcgggctc tgcactccca agctttgtgg ccctgaggcc gtcattccct  96720
tctcctagcc ttagtctccc tcatctttaa aatgggacgg ctagaattca tcattggctg  96780
gggcacattg gctcaagcct gtaatcccag cactttggga ggcttaggtg gaaagatcgc  96840
ttgagcccag gagtttgaga ccagccttgg gaacataatg agactttgtt tctatttcta  96900
tttaaaaaaa taaagaaccc atcactgtga actcttgtga gaatccagtg aggagacgtg  96960
tgtaagtgcc tgccacagtg cctggcacat ggttggaacc ccagaatgta tatggtccca  97020
gtattattgt ttctatgctg tgtcccaaaa agctgactta tgtcaactgt gggagcccac  97080
catttcagaa attactgaat aacctgtgga atttcccctt agttacaaag gttactcttt  97140
taaaaactct gtcctcggtc aggcgctgtg gctcacgcct gtaatcccag cactttggga  97200
ggccgaggcg ggtgagtcac ttgaggtcag gcatttgaga tgagcctggc caacatattg  97260
aaaccttgtc tctactaaaa atacaaaaat tagctgggca tggtggcaca tgcctgtaat  97320
cccagctact tgggaggctg aggtatggga atcgattgaa cccggaggtg gaggttgtag  97380
tgagccaaga tcgtgccact gcactccagc ctgggcaata gagcaagact ctgtctcaga  97440
atgaacaaac aaaaaataaa aactctgtcc ttaaggacag ggtgatgctt ctctaccttc  97500
tcctttaggg gcaggatgga gtaaccactg gactgaagaa atgatctgtg agtccagacg  97560
tggtggctca tgcctctaat cccagcattt taggaggctg aggtcagaga attgctcgag  97620
ccgaggagtt caagatcagc ctgggcaaca aagcatgatg ttgtctccac aaaaataaaa  97680
taatgaagta aaatatctga aacctgctgc agcctgttca ttggtgttaa gataactccc  97740
tctcccagaa gccttggcta agcacactgt tgaggccagt gcttctcaat aggtgggtga  97800
ctttgtcctc ctcaccccca gggacacttg gtaatatctg gagacatttt gggttactgc  97860
aattggatgg tatgctactg gcacctatgg gcagaagcca gggatgctgt ttcacaccct  97920
gcagcaaaca agacagccct gtccacccaa caaagaattg tctggccaca acattactaa  97980
agctgaggct gagggaagtt ggtctaggct acatgttttt ctctttacag agaaaatgac  98040
ccatcatgtc tcctaataga gaaacgctgc ttccggccga atgacaagag ctcacgcctg  98100
```

-continued

```
taatcccgac actttgggag gccaaggcag gtggatcact tgaggtcagg agctcgagac  98160
cagcctggcc aacatggtga aacctcgtct ctactaaaaa tacaaaaatt tttagtagaa  98220
atttagtaga aatttttagt agaaatttag tagaaattta gaataagcca ggtgtagtgg  98280
cacacacctg taatcccagc tacacaggaa gcagaggcag gagaagtgct tgaacccgag  98340
aggcagaaat tgcagtgagc tgagatcatg ccacttcatt ccagtctggg cgacagagca  98400
agcctctcaa aaaaaaaaaa aaaaaaaaaa aaaaaaaagc tgcttcccag attgggcaac  98460
agaaatacga gtggtgtgca gaatgagtgt gtaaatatag gtgcatagga acatggggag  98520
ggtgaatcca tgacatgagg ggaggtgtgc acggaggggt atgtgtgcac acaggtgtgt  98580
ctgtgcccag gttgtgtgtg tgtgcgtgca tgcatgtact tgtgcgatgt atgaatcagt  98640
gcctataagt gtgtgcatcg tgtgcaagtg gcacgtgtga tgtgggcctg taagacagga  98700
aattgtgttg ataagaaatg tatgggatga tgggtactga caggtgcggg agtggatttt  98760
gtgtctctag agtgtaagtg actggcttgt gtgtgtcact gtatagagaa taagttgtat  98820
gtggaaacag gaggagaaag gaagggaccc aaggcatgag ccaccatttt ggtttcccag  98880
ggtggcccac gccccgactt accgctccgg aggcctgctg ggcagcgttg gtagctggca  98940
agacaaagca gagaagccag taaccaaaca gcactccaga tgactggact cccttttttcc 99000
tctcggtgtg aatcaggaac actgcgaagc tctggacggg aaagtcaggg aggcccctta  99060
ggggagggtg ggaggctgag gggagcctct tctcttcccc ttgttctcca ctgtggcagg  99120
caaagcagca gctgggagga agccgggctc cagactgaag gcatcattac catcgtggtg  99180
agccacacag taggatgaat gaggaattct ggggcctcag gcgttccctg ttggattttc  99240
caaagagcga cagccacgct ggaggtacac aggactatga gggcgaatcc aagcacctga  99300
ggatacaggc ttagataagc ttggggggca ataagagagg tcacagcaaa ctggtaggcg  99360
gccccatgtc caactgggag ctggttctgc aacatcctgg ctgatactga gtataccagg  99420
gtcaccagct agcaacgtgc caatgtgaac aatgtgtaaa gggcattgca gatcactcct  99480
gacctgtaac tgtcatataa ataatgcaca ggaagggctt gagccaaccg agtgttttcc  99540
aaaatgcagg aagtgctcca atcgtgcaca tatgagatga ctttgggtat ggagaaacag  99600
caggaaatga aatgtactca ccaggtaaaa aactatcctt tctccaagtc atttttcaat  99660
ccctgctatg aaatcaagga gcaactctct gttgggccag taagtctcta gggtctctct  99720
aatatatttt ggtttctcta ttgaataaaa gaaaggaaga aaatgagaga acgtgggcac  99780
accagaggga aggccagagc taggttacgt tggaggaact gctcaaagaa cctcagttta  99840
aagcagaagt tggcaaacta tcaatcatca aagaaaaaca aaaagcatat gtcatgacag  99900
gtgaaaatta catgaaatcc aaatttcagt gactacaaat aaagttttat tgaaacgcag  99960
tcggccgggg gtggtggctt acacctgtaa tcccagcact ttggcaggcc aaggcaggca 100020
gatcacctga ggtcaggagt tggagaccag cctggccaac atggcgaaac cctgtttcta 100080
ctaaaaatac aaaaaaatag cgaggtgtgg gggtgggcac ctgtaatccc agctactcgg 100140
gaagctgagg caggagaatc acttgaaccc aggaggcgga ggttgcagtg agccgagatc 100200
gcaccattgc actccagcct gggtaacaag agcaaaactg catctcaaaa aaaaaaaaca 100260
aacaaaaaag taacacagtc atgactattg tctatggtta tgactattgc gttcattctg 100320
gaatggcaga gttcagtgtt cggaaggaag attacctggc tcacaaagtc tcaaatactg 100380
tgtaccgctt ggctctttaa gtttgccaac ccctgggttg gtggcgggtg ataatgtaaa 100440
```

-continued

```
aattaataca atggcagaag aatgaatgaa ctctgaagaa cattctttgg aagcctacaa 100500
gaatggagta gaagaggatg gatgagcaga aaggctcaca cttggaatgc cagtgtttat 100560
ttaacacact aaggtaaata catatcacat ataaaaattg tcctataata cagccagtgg 100620
gggaacataa aaataaatgc ataacttttt aaaaggttca tcctaatgtg gctctaaaat 100680
taccttgtgt atccaagagt ctacatggta tgttttggaa aatgccaggt tatggtagct 100740
ataaactgtc caggaacatg ggagtgtatg cgtatgtttg cgcatgcgtg gattttcgga 100800
attacaaaat ctgtttggga gaaccgtgtt ccactgagtt gacctctgta gcctttctaa 100860
tattgctctg tttgattaac agattccctt ctacaccccg ataggaggag tctactttaa 100920
gacttcacca ggttccagcc tgtcccctgc ctcccccgaa cattgcctgg ttccaggctc 100980
ccagggatgg cagctaccat cttggctttg aagagtgggg acatccacag gtagccccgg 101040
ccatggtggt ggatgaagag gaggtagatg ggaccaagga cccagaggta catgggggt 101100
acccagaccc ctgctgttct caggaagcac aggctcagca ggctggtggc ggcaggttca 101160
ggctctgtct ggttccagac ctgagggaac acaaagagga cccttaggat ggtacaaggc 101220
aggggtcccc agctcacctg cccagggggc caggcaactt tttggatctt taacatttac 101280
acaaaaatgt accaagtact ctttggaata cctactaatt ctcaattcct ttcatcctga 101340
cattaaccct aggtagttgc aattatattg atttgcagat gaagaagctg aggaccagag 101400
aggttgagta actttgctga ctttacccag ctgaggagtg gaagggctgg gatttgaacc 101460
cagggaactg ggccatgtgg tctaggagac ctgggctcca taatcattgc taggcatgga 101520
ctgtcagtta atccttataa caactccagg acgcagacag tactgtctcc atttcagaaa 101580
ccagcagact gaggcaccag tcggggaact gcctccccca gggacacaca aatgggaagt 101640
ggcaaagctg actctgaccc aggcttatct gaccccaaac ctcgttcgac tggtggtctt 101700
gatgtatgat ttgtttttat tttttattat taattaattt atgttttaga gacagggtct 101760
cactctgttg cccaggctga agtggcacaa tcaaagctca acaaagcttc gaatttcctg 101820
ggctcaagca atcctcccac ctcggcctcc cagagtgctg ggattacagg cataagcagc 101880
ctcaccaggc ctggctaatt tttttttttt atgttttgta gagatggggg tctctctatg 101940
ctggtctcga actcctggtc tcaagcaatc ctcctgcctc agcctcctag gtactgggat 102000
tacaggcaag agccaccggc ccagcttgat ctgttatttt catctcagca ggtctgctgg 102060
tcctatctaa ccctagaaga aatttgaagt ttagtggacg tggcctcttc aattctctct 102120
ccgctgtctt tttactcctc ctggtttcac aactcaccgg ctgtgcaaac tttaacctct 102180
ctgtatctca gtttccttcc ctgtaaaagg gggaaaacga gactctacct ctatgagttg 102240
tattaaatgg attaatagca gcaaagttca tagcagcatg gcacaaggtt gggcacaagg 102300
ctaggcacag agaaagccct cagttcattg ccagtttatt gcttcaactc cctggccctc 102360
gaaatgctgg cagtttgcaa cccccacccc cactccatga actccactcc ctggagtcct 102420
ttgctaagag caatggaaaa agaaaccaga gaggtaaggg ctctccgggg gtaggagggc 102480
ttgggggacc cactagcttt atgcaaagaa gagtcaaagc ccctagtagc tgggaggtct 102540
ggtggcccct taaatagagc tgggctctcg gctgctggct tggtgaaaga aatccaaccc 102600
gctgcagtga gggggccgga gtaagtctcc tcgcttcccg ggtccaggaa tttgggggtc 102660
tctcctctcc ccagtatcgc agcccgagag atctgcagcc aaaccaagcc tggaaaagga 102720
gagtggggcg cgatgggggg cactcacccc ctgccccgcg cagggctcag caggcgcggc 102780
catcggcgcc ttctgtcgtc gtgggtccca gcgtctgtct gtcgctaagt ctctgggcag 102840
```

-continued

```
actgctcggc cgcgatcctg ccggagaaga ggcggggctg ggctggtcgg gctgggctgg 102900
tccggctggg attcgagctc cgggatcggg aggccccggg caaggtccag ctgcgcggcg 102960
ggagtgaggc cacgggaggt gaaaacaggc gaggtggggg atgggggaag agaggcgctc 103020
ggggagctgg gacgggcacc gggttggggg gtcccggaac ccctgaaagt tcagtgacac 103080
ctccatagtt ccctcttccc cctgcaacaa gaatcactcc agacttccta aacactttgg 103140
acccagcaat ttccaggagt tcatcctgat gagagaactg aaaggtgtgc acacgttagt 103200
aacaaggagg cctggtgacc gcctaagcgt ccaatcgcgg ggaccaccgg gtcgaggccg 103260
agaggatgga gaccgcgtca caggcacctc gctgctggaa tggagggtgg tggggagaac 103320
ttagaagatt atgcaatggg ctggcagggc tatacccagc cgccctggta agcagaaact 103380
caagaaacct ctagggtcct gttttctggt cgtatgatcc caggagtgca catgggcccc 103440
tcgggtgtct gaacagaagg gcataggagg gagggccgca gccctgcagt cttactctgc 103500
tggtgtagcg gtcacctgcc aactcccacc ccaccctgca ccgcgggctc ctgagtcggc 103560
agattaagca ttttataaat tctattttaa atacgtgttt taaacttgtc agatatttgt 103620
cttcatttca gtccctgcgc ctctacctct tgctgtggtc gcttatttaa cactgggggg 103680
ctacgttctg ctaagtccca gggagagact gttcctaata tccgagggag atattattcc 103740
taatatcacg ctgggtgaac accacgtgtg tacagcctct gatacgattg gtaatatcca 103800
agggagatat tatcctaaca tcccagtggg tgaacaccat gtgtgtaaac gctgtggtat 103860
tattagaaat atccaaggga gatattactc ctaatatcac agtgggtgta catcctgtga 103920
tattattcgt aatatctgaa ggagatttta ctcctaatat cacagtggga gtacacactg 103980
tgatattatt tgtaatatcc gagggagatt ttactcctaa tatcacagta ggtgtacaac 104040
ctgtgatatt attcataata tgctagagat atattactcc aaatctcatg gtgggtgtac 104100
actctgtcat agaattcgtg atatcctagg gagttattac cgctaatatc acagtgagag 104160
tacaccctgt gatattattc atactatcct agaaagatat tacttttaat atcacagagg 104220
gtgtacaccc tgtgatatta ttcataatat tctatgaaga tataactcct gatataaccg 104280
taggtgtata ccctgtgata ttatttgtta tatcctaggg agatactaca cctaatacca 104340
cagtgggtgt acaccctgtg atatgatttg taatatccta gggagatata actcctaata 104400
tcacagaggg agtacaccct gtaatattat tcataatatc ctagaaagat aatactttca 104460
atatcacagt gggtgtacac tctgtgataa tattcgtaat ttcctaggga gatactactc 104520
ctaatatcac cttgagtgta cactgcgtga tattattcgt aatatcgtag ggagctattg 104580
cttttaattt cacagtgggt gtatacccta tgatattatt cataatatct taagaaggta 104640
gtactcctaa aatcacagtg cctgtacaca ctgtgatatt attcataata ttctagggag 104700
atgttactcc taatctcata gtgggtgtac accttgtgat actatttgta atgttctaga 104760
aagatattcc ttttaatatc acagtgggtg tacaccctgt gatatgattc gaaatattct 104820
agggcgatat tactcctaat atcccagtga atttacacca tgcgtgtaca cgctgtgacc 104880
tcccagaaag atatgactcc taatatcaca gtgggggtac accctgtgct attatttgta 104940
ataccctatg gatatcataa tatcacaatg aacgtacacc attgtgtaca tgctgtgata 105000
ttatttgtaa tatttttggg tgatattacc cctaatgtca cagtgcgtgt acatcttttg 105060
atattatttg taatattctg tggagatatt gcccctaata tcacagtggg tgtatactct 105120
ttgatactat tcgtaacatc ctggaagata ttatccatat tgtcacggtg ggtgtacacc 105180
```

-continued

```
ctgtgatatt attcgttata ttctggggat atactattac ccctaatata ctgtgggtgt 105240
acccccctgtg atattattca ctatatcttg gagatataat attaccccta atatcacagt 105300
gggtgtatac tttgtgatat tattcattat atcctgaaga gatattattt cctttaatat 105360
cacagtgcat gtacaccttg tgatattatt tgttatatcc tggggagata ctactatatt 105420
actcctagta tcacagtggc tgtacgcctt gtgatactat tcattatatc ctggggagat 105480
attattactc ctaatatcac agtaagtgta taccctgtga tattattcat aatatcctgg 105540
gagatattac ccatattgtc acagtgggtg tacatcctgt aatattattt gtaatatcct 105600
ggggagatat tattactcct aatagcacag tgggtgtaca ccctgtgata ttattggtta 105660
tatcctgggg aggtattatt attcctaata tcacagtggg tgaacattct gtaatattat 105720
tcattatatt ttggggagat attaattcct ctaatatcac agtgggtgta caccctgtga 105780
tattattcat tatatcctgg gaagatatta atccctctaa tatcacagtg ggtgtacacc 105840
ctgtaatatt attcattata tcctgggaag atattatttc ctctaatatc acagtgggtg 105900
tacaccctgt gatattattt gttgtatcct ggggagatat tattatgtct catatcacaa 105960
tgggtgaaca ccctgtgata gtattcgtta tatttgggga agatgttatt acccctaata 106020
tcacagtggt gtacactctg tgatattatt cattatgtag tggggagata gtattaccca 106080
taatatcaca gtggatgtac accctgtcat attatttgtt atatccttga gaaatattat 106140
tattcctctt atcacagtgg gtgtacaccc tgtgatatta ttcgttacat cctagggaga 106200
tattgttacc cataatatca cagtggatgt acaccctgtc atattattcg ttatatcctt 106260
gagagatgtt actaccccta atatcacagt gggtgtatac cctgtgatat tattcatcaa 106320
attttctgga gatattatta cccataatat cacagtgtgt gtacccactg tgacagtatt 106380
gattatatct tggggcgata ttactcttaa tttcacagtg gctgtatccc tgtgtttaca 106440
ccctgtgatg ttattcataa tattttaggg agatattact cctaatatca cagtcagtgt 106500
ataccatgtt tgtacaccct atgatattat ttgtaatatt ttagggagat attactccta 106560
atatcgttgt gggtgtacag catgtttgta aacactgtga tattattcat aatatctgag 106620
agagatatta ctgccaatat cacagtgggt gtacaccctg tacaccgtgt gatacgattc 106680
ataaatatccg agggagatat tactcccagt atcacagtgg gtttacaccc tgtggtatta 106740
ttcataatat tcgagggaga tattactctc aatatcacag tggatgtaca ccctgtgata 106800
ttatttgcaa tatccgaggg aaacattact gctaatatca cagtgggagt acaccctgtg 106860
atattatttg ttttatcctg gagacatatt attcctatta tcacagtggt tgtacaccct 106920
gtgatattct tcgctatatt catggaagat gttattaccc ctaatatcac agttggtgta 106980
caccctgtga tattattcgt tatatcctgg ggagatattg ttacccctag tatcacagtg 107040
ggtgtacgcc ctgtcatatt atccattaca tcatgggaag atattattac atctaatatc 107100
actgtgggtg tacaccctgt gatattattt attatatcct ggtgagatgt tattactgct 107160
aatatcacag ggtgtgtcaa attttctgga gatattatta cccttaatat cacagtgggt 107220
gtgcaccctg tgtgtacact ctgtaatatt atttgtaata ttttagggag atattactac 107280
taatatcaca gtgggtgtac accctgagga gatattactt cctctgatat cacagtgggt 107340
gtacaccctc tcatattatt cgttatgtgc taagtagata ttattacccc taatatcaca 107400
gtgggtgtac accctgtgat gttattcctt atatcccaag aagatattat tataactaat 107460
atcacagtgg gtgtacaccc tatgatatta tctgttatat actgggggga tattatttgt 107520
aatattttag ggagatacta ctcctaatat catagtgggt gtactcatat tttacagata 107580
```

-continued

```
tattactttt aatatcacag tgggtgtaca ccctgtgtgt acaccctgta atattattag 107640

taatatttta gggagatatt actcctaata tcatagtggg tgtacaccat gtttgtaaac 107700

cctaggatat tattcataat atccgaggga gatattactc ccaatatcac ggtgggttta 107760

caccctatga tattatttgt aatatctgag gcaggtatta ctctccatat cacagtgagt 107820


<210> SEQ ID NO 2
<211> LENGTH: 4512
<212> TYPE: DNA
<213> ORGANISM: Homo sapiens
<220> FEATURE:
<221> NAME/KEY: CDS
<222> LOCATION: (1)..(4512)
<223> OTHER INFORMATION: cDNA for human MRP6 protein

<400> SEQUENCE: 2

atg gcc gcg cct gct gag ccc tgc gcg ggg cag ggg gtc tgg aac cag       48
Met Ala Ala Pro Ala Glu Pro Cys Ala Gly Gln Gly Val Trp Asn Gln
1               5                   10                  15

aca gag cct gaa cct gcc gcc acc agc ctg ctg agc ctg tgc ttc ctg       96
Thr Glu Pro Glu Pro Ala Ala Thr Ser Leu Leu Ser Leu Cys Phe Leu
            20                  25                  30

aga aca gca ggg gtc tgg gta ccc ccc atg tac ctc tgg gtc ctt ggt      144
Arg Thr Ala Gly Val Trp Val Pro Pro Met Tyr Leu Trp Val Leu Gly
        35                  40                  45

ccc atc tac ctc ctc ttc atc cac cac cat ggc cgg ggc tac ctg tgg      192
Pro Ile Tyr Leu Leu Phe Ile His His His Gly Arg Gly Tyr Leu Trp
    50                  55                  60

atg tcc cca ctc ttc aaa gcc aag atg gtg ctt gga ttc gcc ctc ata      240
Met Ser Pro Leu Phe Lys Ala Lys Met Val Leu Gly Phe Ala Leu Ile
65                  70                  75                  80

gtc ctg tgt acc tcc agc gtg gct gtc gct ctt tgg aaa atc caa cag      288
Val Leu Cys Thr Ser Ser Val Ala Val Ala Leu Trp Lys Ile Gln Gln
                85                  90                  95

gga acg cct gag gcc cca gaa ttc ctc att cat cct act gtg tgg ctc      336
Gly Thr Pro Glu Ala Pro Glu Phe Leu Ile His Pro Thr Val Trp Leu
            100                 105                 110

acc acg atg agc ttc gca gtg ttc ctg att cac acc gag agg aaa aag      384
Thr Thr Met Ser Phe Ala Val Phe Leu Ile His Thr Glu Arg Lys Lys
        115                 120                 125

gga gtc cag tca tct gga gtg ctg ttt ggt tac tgg ctt ctc tgc ttt      432
Gly Val Gln Ser Ser Gly Val Leu Phe Gly Tyr Trp Leu Leu Cys Phe
    130                 135                 140

gtc ttg cca gct acc aac gct gcc cag cag gcc tcc gga gcg ggc ttc      480
Val Leu Pro Ala Thr Asn Ala Ala Gln Gln Ala Ser Gly Ala Gly Phe
145                 150                 155                 160

cag agc gac cct gtc cgc cac ctg tcc acc tac cta tgc ctg tct ctg      528
Gln Ser Asp Pro Val Arg His Leu Ser Thr Tyr Leu Cys Leu Ser Leu
                165                 170                 175

gtg gtg gca cag ttt gtg ctg tcc tgc ctg gcg gat caa ccc ccc ttc      576
Val Val Ala Gln Phe Val Leu Ser Cys Leu Ala Asp Gln Pro Pro Phe
            180                 185                 190

ttc cct gaa gac ccc cag cag tct aac ccc tgt cca gag act ggg gca      624
Phe Pro Glu Asp Pro Gln Gln Ser Asn Pro Cys Pro Glu Thr Gly Ala
        195                 200                 205

gcc ttc ccc tcc aaa gcc acg ttc tgg tgg gtt tct ggc ctg gtc tgg      672
Ala Phe Pro Ser Lys Ala Thr Phe Trp Trp Val Ser Gly Leu Val Trp
    210                 215                 220

agg gga tac agg agg cca ctg aga cca aaa gac ctc tgg tcg ctt ggg      720
Arg Gly Tyr Arg Arg Pro Leu Arg Pro Lys Asp Leu Trp Ser Leu Gly
```

-continued

```
225                 230                 235                 240

aga gaa aac tcc tca gaa gaa ctt gtt tcc cgg ctt gaa aag gag tgg      768
Arg Glu Asn Ser Ser Glu Glu Leu Val Ser Arg Leu Glu Lys Glu Trp
                245                 250                 255

atg agg aac cgc agt gca gcc cgg agg cac aac aag gca ata gca ttt      816
Met Arg Asn Arg Ser Ala Ala Arg Arg His Asn Lys Ala Ile Ala Phe
            260                 265                 270

aaa agg aaa ggc ggc agt ggc atg aag gct cca gag acc gag ccc ttc      864
Lys Arg Lys Gly Gly Ser Gly Met Lys Ala Pro Glu Thr Glu Pro Phe
        275                 280                 285

cta cgg caa gaa ggg agc cag tgg cgc cca ctg ctg aag gcc atc tgg      912
Leu Arg Gln Glu Gly Ser Gln Trp Arg Pro Leu Leu Lys Ala Ile Trp
    290                 295                 300

cag gtg ttc cat tct acc ttc ctc ctg ggg acc ctc agc ctc atc atc      960
Gln Val Phe His Ser Thr Phe Leu Leu Gly Thr Leu Ser Leu Ile Ile
305                 310                 315                 320

agt gat gtc ttc agg ttc act gtc ccc aag ctg ctc agc ctt ttc ctg     1008
Ser Asp Val Phe Arg Phe Thr Val Pro Lys Leu Leu Ser Leu Phe Leu
                325                 330                 335

gag ttt att ggt gat ccc aag cct cca gcc tgg aag ggc tac ctc ctc     1056
Glu Phe Ile Gly Asp Pro Lys Pro Pro Ala Trp Lys Gly Tyr Leu Leu
            340                 345                 350

gcc gtg ctg atg ttc ctc tca gcc tgc ctg caa acg ctg ttt gag cag     1104
Ala Val Leu Met Phe Leu Ser Ala Cys Leu Gln Thr Leu Phe Glu Gln
        355                 360                 365

cag aac atg tac agg ctc aag gtg ctg cag atg agg ttg cgg tcg gcc     1152
Gln Asn Met Tyr Arg Leu Lys Val Leu Gln Met Arg Leu Arg Ser Ala
    370                 375                 380

atc act ggc ctg gtg tac aga aag gtc ctg gct ctg tcc agc ggc tcc     1200
Ile Thr Gly Leu Val Tyr Arg Lys Val Leu Ala Leu Ser Ser Gly Ser
385                 390                 395                 400

aga aag gcc agt gcg gtg ggt gat gtg gtc aat ctg gtg tcc gtg gac     1248
Arg Lys Ala Ser Ala Val Gly Asp Val Val Asn Leu Val Ser Val Asp
                405                 410                 415

gtg cag cgg ctg acc gag agc gtc ctc tac ctc aac ggg ctg tgg ctg     1296
Val Gln Arg Leu Thr Glu Ser Val Leu Tyr Leu Asn Gly Leu Trp Leu
            420                 425                 430

cct ctc gtc tgg atc gtg gtc tgc ttc gtc tat ctc tgg cag ctc ctg     1344
Pro Leu Val Trp Ile Val Val Cys Phe Val Tyr Leu Trp Gln Leu Leu
        435                 440                 445

ggg ccc tcc gcc ctc act gcc atc gct gtc ttc ctg agc ctc ctc cct     1392
Gly Pro Ser Ala Leu Thr Ala Ile Ala Val Phe Leu Ser Leu Leu Pro
    450                 455                 460

ctg aat ttc ttc atc tcc aag aaa agg aac cac cat cag gag gag caa     1440
Leu Asn Phe Phe Ile Ser Lys Lys Arg Asn His His Gln Glu Glu Gln
465                 470                 475                 480

atg agg cag aag gac tca cgg gca cgg ctc acc agc tct atc ctc agg     1488
Met Arg Gln Lys Asp Ser Arg Ala Arg Leu Thr Ser Ser Ile Leu Arg
                485                 490                 495

aac tcg aag acc atc aag ttc cat ggc tgg gag gga gcc ttt ctg gac     1536
Asn Ser Lys Thr Ile Lys Phe His Gly Trp Glu Gly Ala Phe Leu Asp
            500                 505                 510

aga gtc ctg ggc atc cga ggc cag gag ctg ggc gcc ttg cgg acc tcc     1584
Arg Val Leu Gly Ile Arg Gly Gln Glu Leu Gly Ala Leu Arg Thr Ser
        515                 520                 525

ggc ctc ctc ttc tct gtg tcg ctg gtg tcc ttc caa gtg tct aca ttt     1632
Gly Leu Leu Phe Ser Val Ser Leu Val Ser Phe Gln Val Ser Thr Phe
    530                 535                 540

ctg gtc gca ctg gtg gtg ttt gct gtc cac act ctg gtg gcc gag aat     1680
```

-continued

```
Leu Val Ala Leu Val Val Phe Ala Val His Thr Leu Val Ala Glu Asn
545                 550                 555                 560

gct atg aat gca gag aaa gcc ttt gtg act ctc aca gtt ctc aac atc      1728
Ala Met Asn Ala Glu Lys Ala Phe Val Thr Leu Thr Val Leu Asn Ile
                565                 570                 575

ctc aac aag gcc cag gct ttc ctg ccc ttc tcc atc cac tcc ctc gtc      1776
Leu Asn Lys Ala Gln Ala Phe Leu Pro Phe Ser Ile His Ser Leu Val
            580                 585                 590

cag gcc cgg gtg tcc ttt gac cgt ctg gtc acc ttc ctc tgc ctg gaa      1824
Gln Ala Arg Val Ser Phe Asp Arg Leu Val Thr Phe Leu Cys Leu Glu
        595                 600                 605

gaa gtt gac cct ggt gtc gta gac tca agt tcc tct gga agc gct gcc      1872
Glu Val Asp Pro Gly Val Val Asp Ser Ser Ser Ser Gly Ser Ala Ala
    610                 615                 620

ggg aag gat tgc atc acc ata cac agt gcc acc ttc gcc tgg tcc cag      1920
Gly Lys Asp Cys Ile Thr Ile His Ser Ala Thr Phe Ala Trp Ser Gln
625                 630                 635                 640

gaa agc cct ccc tgc ctc cac aga ata aac ctc acg gtg ccc cag ggc      1968
Glu Ser Pro Pro Cys Leu His Arg Ile Asn Leu Thr Val Pro Gln Gly
                645                 650                 655

tgt ctg ctg gct gtt gtc ggt cca gtg ggg gca ggg aag tcc tcc ctg      2016
Cys Leu Leu Ala Val Val Gly Pro Val Gly Ala Gly Lys Ser Ser Leu
            660                 665                 670

ctg tcc gcc ctc ctt ggg gag ctg tca aag gtg gag ggg ttc gtg agc      2064
Leu Ser Ala Leu Leu Gly Glu Leu Ser Lys Val Glu Gly Phe Val Ser
        675                 680                 685

atc gag ggt gct gtg gcc tac gtg ccc cag gag gcc tgg gtg cag aac      2112
Ile Glu Gly Ala Val Ala Tyr Val Pro Gln Glu Ala Trp Val Gln Asn
    690                 695                 700

acc tct gtg gta gag aat gtg tgc ttc ggg cag gag ctg gac cca ccc      2160
Thr Ser Val Val Glu Asn Val Cys Phe Gly Gln Glu Leu Asp Pro Pro
705                 710                 715                 720

tgg ctg gag aga gta cta gaa gcc tgt gcc ctg cag cca gat gtg gac      2208
Trp Leu Glu Arg Val Leu Glu Ala Cys Ala Leu Gln Pro Asp Val Asp
                725                 730                 735

agc ttc cct gag gga atc cac act tca att ggg gag cag ggc atg aat      2256
Ser Phe Pro Glu Gly Ile His Thr Ser Ile Gly Glu Gln Gly Met Asn
            740                 745                 750

ctc tcc gga ggc cag aag cag cgg ctg agc ctg gcc cgg gct gta tac      2304
Leu Ser Gly Gly Gln Lys Gln Arg Leu Ser Leu Ala Arg Ala Val Tyr
        755                 760                 765

aga aag gca gct gtg tac ctg ctg gat gac ccc ctg gcg gcc ctg gat      2352
Arg Lys Ala Ala Val Tyr Leu Leu Asp Asp Pro Leu Ala Ala Leu Asp
    770                 775                 780

gcc cac gtt ggc cag cat gtc ttc aac cag gtc att ggg cct ggt ggg      2400
Ala His Val Gly Gln His Val Phe Asn Gln Val Ile Gly Pro Gly Gly
785                 790                 795                 800

cta ctc cag gga aca aca cgg att ctc gtg acg cac gca ctc cac atc      2448
Leu Leu Gln Gly Thr Thr Arg Ile Leu Val Thr His Ala Leu His Ile
                805                 810                 815

ctg ccc cag gct gat tgg atc ata gtg ctg gca aat ggg gcc atc gca      2496
Leu Pro Gln Ala Asp Trp Ile Ile Val Leu Ala Asn Gly Ala Ile Ala
            820                 825                 830

gag atg ggt tcc tac cag gag ctt ctg cag agg aag ggg gcc ctc gtg      2544
Glu Met Gly Ser Tyr Gln Glu Leu Leu Gln Arg Lys Gly Ala Leu Val
        835                 840                 845

tgt ctt ctg gat caa gcc aga cag cca gga gat aga gga gaa gga gaa      2592
Cys Leu Leu Asp Gln Ala Arg Gln Pro Gly Asp Arg Gly Glu Gly Glu
    850                 855                 860
```

-continued

```
aca gaa cct ggg acc agc acc aag gac ccc aga ggc acc tct gca ggc      2640
Thr Glu Pro Gly Thr Ser Thr Lys Asp Pro Arg Gly Thr Ser Ala Gly
865                 870                 875                 880

agg agg ccc gag ctt aga cgc gag agg tcc atc aag tca gtc cct gag      2688
Arg Arg Pro Glu Leu Arg Arg Glu Arg Ser Ile Lys Ser Val Pro Glu
                885                 890                 895

aag gac cgt acc act tca gaa gcc cag aca gag gtt cct ctg gat gac      2736
Lys Asp Arg Thr Thr Ser Glu Ala Gln Thr Glu Val Pro Leu Asp Asp
            900                 905                 910

cct gac agg gca gga tgg cca gca gga aag gac agc atc caa tac ggc      2784
Pro Asp Arg Ala Gly Trp Pro Ala Gly Lys Asp Ser Ile Gln Tyr Gly
        915                 920                 925

agg gtg aag gcc aca gtg cac ctg gcc tac ctg cgt gcc gtg ggc acc      2832
Arg Val Lys Ala Thr Val His Leu Ala Tyr Leu Arg Ala Val Gly Thr
    930                 935                 940

ccc ctc tgc ctc tac gca ctc ttc ctc ttc ctc tgc cag caa gtg gcc      2880
Pro Leu Cys Leu Tyr Ala Leu Phe Leu Phe Leu Cys Gln Gln Val Ala
945                 950                 955                 960

tcc ttc tgc cgg ggc tac tgg ctg agc ctg tgg gcg gac gac cct gca      2928
Ser Phe Cys Arg Gly Tyr Trp Leu Ser Leu Trp Ala Asp Asp Pro Ala
                965                 970                 975

gta ggt ggg cag cag acg cag gca gcc ctg cgt ggc ggg atc ttc ggg      2976
Val Gly Gly Gln Gln Thr Gln Ala Ala Leu Arg Gly Gly Ile Phe Gly
            980                 985                 990

ctc ctc ggc tgt ctc caa gcc att  ggg ctg ttt gcc tcc  atg gct gcg    3024
Leu Leu Gly Cys Leu Gln Ala Ile  Gly Leu Phe Ala Ser  Met Ala Ala
        995                 1000                1005

gtg ctc  cta ggt ggg gcc cgg  gca tcc agg ttg ctc  ttc cag agg      3069
Val Leu  Leu Gly Gly Ala Arg  Ala Ser Arg Leu Leu  Phe Gln Arg
    1010                1015                1020

ctc ctg  tgg gat gtg gtg cga  tct ccc atc agc ttc  ttt gag cgg      3114
Leu Leu  Trp Asp Val Val Arg  Ser Pro Ile Ser Phe  Phe Glu Arg
    1025                1030                1035

aca ccc  att ggt cac ctg cta  aac cgc ttc tcc aag  gag aca gac      3159
Thr Pro  Ile Gly His Leu Leu  Asn Arg Phe Ser Lys  Glu Thr Asp
    1040                1045                1050

acg gtt  gac gtg gac att cca  gac aaa ctc cgg tcc  ctg ctg atg      3204
Thr Val  Asp Val Asp Ile Pro  Asp Lys Leu Arg Ser  Leu Leu Met
    1055                1060                1065

tac gcc  ttt gga ctc ctg gag  gtc agc ctg gtg gtg  gca gtg gct      3249
Tyr Ala  Phe Gly Leu Leu Glu  Val Ser Leu Val Val  Ala Val Ala
    1070                1075                1080

acc cca  ctg gcc act gtg gcc  atc ctg cca ctg ttt  ctc ctc tac      3294
Thr Pro  Leu Ala Thr Val Ala  Ile Leu Pro Leu Phe  Leu Leu Tyr
    1085                1090                1095

gct ggg  ttt cag agc ctg tat  gtg gtt agc tca tgc  cag ctg aga      3339
Ala Gly  Phe Gln Ser Leu Tyr  Val Val Ser Ser Cys  Gln Leu Arg
    1100                1105                1110

cgc ttg  gag tca gcc agc tac  tcg tct gtc tgc tcc  cac atg gct      3384
Arg Leu  Glu Ser Ala Ser Tyr  Ser Ser Val Cys Ser  His Met Ala
    1115                1120                1125

gag acg  ttc cag ggc agc aca  gtg gtc cgg gca ttc  cga acc cag      3429
Glu Thr  Phe Gln Gly Ser Thr  Val Val Arg Ala Phe  Arg Thr Gln
    1130                1135                1140

gcc ccc  ttt gtg gct cag aac  aat gct cgc gta gat  gaa agc cag      3474
Ala Pro  Phe Val Ala Gln Asn  Asn Ala Arg Val Asp  Glu Ser Gln
    1145                1150                1155

agg atc  agt ttc ccg cga ctg  gtg gct gac agg tgg  ctt gcg gcc      3519
Arg Ile  Ser Phe Pro Arg Leu  Val Ala Asp Arg Trp  Leu Ala Ala
    1160                1165                1170
```

-continued

```
aat gtg  gag ctc ctg ggg aat  ggc ctg gtg ttt gca  gct gcc acg      3564
Asn Val  Glu Leu Leu Gly Asn  Gly Leu Val Phe Ala  Ala Ala Thr
    1175                 1180                 1185

tgt gct  gtg ctg agc aaa gcc  cac ctc agt gct ggc  ctc gtg ggc      3609
Cys Ala  Val Leu Ser Lys Ala  His Leu Ser Ala Gly  Leu Val Gly
    1190                 1195                 1200

ttc tct  gtc tct gct gcc ctc  cag gtg acc cag aca  ctg cag tgg      3654
Phe Ser  Val Ser Ala Ala Leu  Gln Val Thr Gln Thr  Leu Gln Trp
    1205                 1210                 1215

gtt gtt  cgc aac tgg aca gac  cta gag aac agc atc  gtg tca gtg      3699
Val Val  Arg Asn Trp Thr Asp  Leu Glu Asn Ser Ile  Val Ser Val
    1220                 1225                 1230

gag cgg  atg cag gac tat gcc  tgg acg ccc aag gag  gct ccc tgg      3744
Glu Arg  Met Gln Asp Tyr Ala  Trp Thr Pro Lys Glu  Ala Pro Trp
    1235                 1240                 1245

agg ctg  ccc aca tgt gca gct  cag ccc ccc tgg cct  cag ggc ggg      3789
Arg Leu  Pro Thr Cys Ala Ala  Gln Pro Pro Trp Pro  Gln Gly Gly
    1250                 1255                 1260

cag atc  gag ttc cgg gac ttt  ggg cta aga tac cga  cct gag ctc      3834
Gln Ile  Glu Phe Arg Asp Phe  Gly Leu Arg Tyr Arg  Pro Glu Leu
    1265                 1270                 1275

ccg ctg  gct gtg cag ggc gtg  tcc ttc aag atc cac  gca gga gag      3879
Pro Leu  Ala Val Gln Gly Val  Ser Phe Lys Ile His  Ala Gly Glu
    1280                 1285                 1290

aag gtg  ggc atc gtt ggc agg  acc ggg gca ggg aag  tcc tcc ctg      3924
Lys Val  Gly Ile Val Gly Arg  Thr Gly Ala Gly Lys  Ser Ser Leu
    1295                 1300                 1305

gcc agt  ggg ctg ctg cgg ctc  cag gag gca gct gag  ggt ggg atc      3969
Ala Ser  Gly Leu Leu Arg Leu  Gln Glu Ala Ala Glu  Gly Gly Ile
    1310                 1315                 1320

tgg atc  gac ggg gtc ccc att  gcc cac gtg ggg ctg  cac aca ctg      4014
Trp Ile  Asp Gly Val Pro Ile  Ala His Val Gly Leu  His Thr Leu
    1325                 1330                 1335

cgc tcc  agg atc agc atc atc  ccc cag gac ccc atc  ctg ttc cct      4059
Arg Ser  Arg Ile Ser Ile Ile  Pro Gln Asp Pro Ile  Leu Phe Pro
    1340                 1345                 1350

ggc tct  ctg cgg atg aac ctc  gac ctg ctg cag gag  cac tcg gac      4104
Gly Ser  Leu Arg Met Asn Leu  Asp Leu Leu Gln Glu  His Ser Asp
    1355                 1360                 1365

gag gct  atc tgg gca gcc ctg  gag acg gtg cag ctc  aaa gcc ttg      4149
Glu Ala  Ile Trp Ala Ala Leu  Glu Thr Val Gln Leu  Lys Ala Leu
    1370                 1375                 1380

gtg gcc  agc ctg ccc ggc cag  ctg cag tac aag tgt  gct gac cga      4194
Val Ala  Ser Leu Pro Gly Gln  Leu Gln Tyr Lys Cys  Ala Asp Arg
    1385                 1390                 1395

ggc gag  gac ctg agc gtg ggc  cag aaa cag ctc ctg  tgt ctg gca      4239
Gly Glu  Asp Leu Ser Val Gly  Gln Lys Gln Leu Leu  Cys Leu Ala
    1400                 1405                 1410

cgt gcc  ctt ctc cgg aag acc  cag atc ctc atc ctg  gac gag gct      4284
Arg Ala  Leu Leu Arg Lys Thr  Gln Ile Leu Ile Leu  Asp Glu Ala
    1415                 1420                 1425

act gct  gcc gtg gac cct ggc  acg gag ctg cag atg  cag gcc atg      4329
Thr Ala  Ala Val Asp Pro Gly  Thr Glu Leu Gln Met  Gln Ala Met
    1430                 1435                 1440

ctc ggg  agc tgg ttt gca cag  tgc act gtg ctg ctc  att gcc cac      4374
Leu Gly  Ser Trp Phe Ala Gln  Cys Thr Val Leu Leu  Ile Ala His
    1445                 1450                 1455

cgc ctg  cgc tcc gtg atg gac  tgt gcc cgg gtt ctg  gtc atg gac      4419
Arg Leu  Arg Ser Val Met Asp  Cys Ala Arg Val Leu  Val Met Asp
```

-continued

```
    1460                1465                1470

aag ggg  cag gtg gca gag agc  ggc agc ccg gcc cag  ctg ctg gcc      4464
Lys Gly  Gln Val Ala Glu Ser  Gly Ser Pro Ala Gln  Leu Leu Ala
    1475                1480                1485

cag aag  ggc ctg ttt tac aga  ctg gcc cag gag tca  ggc ctg gtc      4509
Gln Lys  Gly Leu Phe Tyr Arg  Leu Ala Gln Glu Ser  Gly Leu Val
    1490                1495                1500

tga                                                                 4512


<210> SEQ ID NO 3
<211> LENGTH: 1503
<212> TYPE: PRT
<213> ORGANISM: Homo sapiens

<400> SEQUENCE: 3

Met Ala Ala Pro Ala Glu Pro Cys Ala Gly Gln Gly Val Trp Asn Gln
1               5                   10                  15

Thr Glu Pro Glu Pro Ala Ala Thr Ser Leu Leu Ser Leu Cys Phe Leu
            20                  25                  30

Arg Thr Ala Gly Val Trp Val Pro Pro Met Tyr Leu Trp Val Leu Gly
        35                  40                  45

Pro Ile Tyr Leu Leu Phe Ile His His His Gly Arg Gly Tyr Leu Trp
    50                  55                  60

Met Ser Pro Leu Phe Lys Ala Lys Met Val Leu Gly Phe Ala Leu Ile
65                  70                  75                  80

Val Leu Cys Thr Ser Ser Val Ala Val Ala Leu Trp Lys Ile Gln Gln
                85                  90                  95

Gly Thr Pro Glu Ala Pro Glu Phe Leu Ile His Pro Thr Val Trp Leu
            100                 105                 110

Thr Thr Met Ser Phe Ala Val Phe Leu Ile His Thr Glu Arg Lys Lys
        115                 120                 125

Gly Val Gln Ser Ser Gly Val Leu Phe Gly Tyr Trp Leu Leu Cys Phe
    130                 135                 140

Val Leu Pro Ala Thr Asn Ala Ala Gln Gln Ala Ser Gly Ala Gly Phe
145                 150                 155                 160

Gln Ser Asp Pro Val Arg His Leu Ser Thr Tyr Leu Cys Leu Ser Leu
                165                 170                 175

Val Val Ala Gln Phe Val Leu Ser Cys Leu Ala Asp Gln Pro Pro Phe
            180                 185                 190

Phe Pro Glu Asp Pro Gln Gln Ser Asn Pro Cys Pro Glu Thr Gly Ala
        195                 200                 205

Ala Phe Pro Ser Lys Ala Thr Phe Trp Trp Val Ser Gly Leu Val Trp
    210                 215                 220

Arg Gly Tyr Arg Arg Pro Leu Arg Pro Lys Asp Leu Trp Ser Leu Gly
225                 230                 235                 240

Arg Glu Asn Ser Ser Glu Glu Leu Val Ser Arg Leu Glu Lys Glu Trp
                245                 250                 255

Met Arg Asn Arg Ser Ala Ala Arg Arg His Asn Lys Ala Ile Ala Phe
            260                 265                 270

Lys Arg Lys Gly Gly Ser Gly Met Lys Ala Pro Glu Thr Glu Pro Phe
        275                 280                 285

Leu Arg Gln Glu Gly Ser Gln Trp Arg Pro Leu Leu Lys Ala Ile Trp
    290                 295                 300

Gln Val Phe His Ser Thr Phe Leu Leu Gly Thr Leu Ser Leu Ile Ile
305                 310                 315                 320
```

-continued

```
Ser Asp Val Phe Arg Phe Thr Val Pro Lys Leu Leu Ser Leu Phe Leu
                325                 330                 335

Glu Phe Ile Gly Asp Pro Lys Pro Pro Ala Trp Lys Gly Tyr Leu Leu
            340                 345                 350

Ala Val Leu Met Phe Leu Ser Ala Cys Leu Gln Thr Leu Phe Glu Gln
        355                 360                 365

Gln Asn Met Tyr Arg Leu Lys Val Leu Gln Met Arg Leu Arg Ser Ala
    370                 375                 380

Ile Thr Gly Leu Val Tyr Arg Lys Val Leu Ala Leu Ser Ser Gly Ser
385                 390                 395                 400

Arg Lys Ala Ser Ala Val Gly Asp Val Val Asn Leu Val Ser Val Asp
                405                 410                 415

Val Gln Arg Leu Thr Glu Ser Val Leu Tyr Leu Asn Gly Leu Trp Leu
            420                 425                 430

Pro Leu Val Trp Ile Val Val Cys Phe Val Tyr Leu Trp Gln Leu Leu
        435                 440                 445

Gly Pro Ser Ala Leu Thr Ala Ile Ala Val Phe Leu Ser Leu Leu Pro
    450                 455                 460

Leu Asn Phe Phe Ile Ser Lys Lys Arg Asn His His Gln Glu Glu Gln
465                 470                 475                 480

Met Arg Gln Lys Asp Ser Arg Ala Arg Leu Thr Ser Ser Ile Leu Arg
                485                 490                 495

Asn Ser Lys Thr Ile Lys Phe His Gly Trp Glu Gly Ala Phe Leu Asp
            500                 505                 510

Arg Val Leu Gly Ile Arg Gly Gln Glu Leu Gly Ala Leu Arg Thr Ser
        515                 520                 525

Gly Leu Leu Phe Ser Val Ser Leu Val Ser Phe Gln Val Ser Thr Phe
    530                 535                 540

Leu Val Ala Leu Val Val Phe Ala Val His Thr Leu Val Ala Glu Asn
545                 550                 555                 560

Ala Met Asn Ala Glu Lys Ala Phe Val Thr Leu Thr Val Leu Asn Ile
                565                 570                 575

Leu Asn Lys Ala Gln Ala Phe Leu Pro Phe Ser Ile His Ser Leu Val
            580                 585                 590

Gln Ala Arg Val Ser Phe Asp Arg Leu Val Thr Phe Leu Cys Leu Glu
        595                 600                 605

Glu Val Asp Pro Gly Val Val Asp Ser Ser Ser Ser Gly Ser Ala Ala
    610                 615                 620

Gly Lys Asp Cys Ile Thr Ile His Ser Ala Thr Phe Ala Trp Ser Gln
625                 630                 635                 640

Glu Ser Pro Pro Cys Leu His Arg Ile Asn Leu Thr Val Pro Gln Gly
                645                 650                 655

Cys Leu Leu Ala Val Val Gly Pro Val Gly Ala Gly Lys Ser Ser Leu
            660                 665                 670

Leu Ser Ala Leu Leu Gly Glu Leu Ser Lys Val Glu Gly Phe Val Ser
        675                 680                 685

Ile Glu Gly Ala Val Ala Tyr Val Pro Gln Glu Ala Trp Val Gln Asn
    690                 695                 700

Thr Ser Val Val Glu Asn Val Cys Phe Gly Gln Glu Leu Asp Pro Pro
705                 710                 715                 720

Trp Leu Glu Arg Val Leu Glu Ala Cys Ala Leu Gln Pro Asp Val Asp
                725                 730                 735
```

-continued

```
Ser Phe Pro Glu Gly Ile His Thr Ser Ile Gly Glu Gln Gly Met Asn
            740                 745                 750

Leu Ser Gly Gly Gln Lys Gln Arg Leu Ser Leu Ala Arg Ala Val Tyr
        755                 760                 765

Arg Lys Ala Ala Val Tyr Leu Leu Asp Asp Pro Leu Ala Ala Leu Asp
    770                 775                 780

Ala His Val Gly Gln His Val Phe Asn Gln Val Ile Gly Pro Gly Gly
785                 790                 795                 800

Leu Leu Gln Gly Thr Thr Arg Ile Leu Val Thr His Ala Leu His Ile
                805                 810                 815

Leu Pro Gln Ala Asp Trp Ile Ile Val Leu Ala Asn Gly Ala Ile Ala
            820                 825                 830

Glu Met Gly Ser Tyr Gln Glu Leu Leu Gln Arg Lys Gly Ala Leu Val
        835                 840                 845

Cys Leu Leu Asp Gln Ala Arg Gln Pro Gly Asp Arg Gly Glu Gly Glu
    850                 855                 860

Thr Glu Pro Gly Thr Ser Thr Lys Asp Pro Arg Gly Thr Ser Ala Gly
865                 870                 875                 880

Arg Arg Pro Glu Leu Arg Arg Glu Arg Ser Ile Lys Ser Val Pro Glu
                885                 890                 895

Lys Asp Arg Thr Thr Ser Glu Ala Gln Thr Glu Val Pro Leu Asp Asp
            900                 905                 910

Pro Asp Arg Ala Gly Trp Pro Ala Gly Lys Asp Ser Ile Gln Tyr Gly
        915                 920                 925

Arg Val Lys Ala Thr Val His Leu Ala Tyr Leu Arg Ala Val Gly Thr
    930                 935                 940

Pro Leu Cys Leu Tyr Ala Leu Phe Leu Phe Leu Cys Gln Gln Val Ala
945                 950                 955                 960

Ser Phe Cys Arg Gly Tyr Trp Leu Ser Leu Trp Ala Asp Asp Pro Ala
                965                 970                 975

Val Gly Gly Gln Gln Thr Gln Ala Ala Leu Arg Gly Gly Ile Phe Gly
            980                 985                 990

Leu Leu Gly Cys Leu Gln Ala Ile  Gly Leu Phe Ala Ser  Met Ala Ala
        995                 1000                1005

Val Leu  Leu Gly Gly Ala Arg  Ala Ser Arg Leu Leu  Phe Gln Arg
    1010                 1015                 1020

Leu Leu  Trp Asp Val Val Arg  Ser Pro Ile Ser Phe  Phe Glu Arg
    1025                 1030                 1035

Thr Pro  Ile Gly His Leu Leu  Asn Arg Phe Ser Lys  Glu Thr Asp
    1040                 1045                 1050

Thr Val  Asp Val Asp Ile Pro  Asp Lys Leu Arg Ser  Leu Leu Met
    1055                 1060                 1065

Tyr Ala  Phe Gly Leu Leu Glu  Val Ser Leu Val Val  Ala Val Ala
    1070                 1075                 1080

Thr Pro  Leu Ala Thr Val Ala  Ile Leu Pro Leu Phe  Leu Leu Tyr
    1085                 1090                 1095

Ala Gly  Phe Gln Ser Leu Tyr  Val Val Ser Ser Cys  Gln Leu Arg
    1100                 1105                 1110

Arg Leu  Glu Ser Ala Ser Tyr  Ser Ser Val Cys Ser  His Met Ala
    1115                 1120                 1125

Glu Thr  Phe Gln Gly Ser Thr  Val Val Arg Ala Phe  Arg Thr Gln
    1130                 1135                 1140

Ala Pro  Phe Val Ala Gln Asn  Asn Ala Arg Val Asp  Glu Ser Gln
```

-continued

```
    1145                1150                1155

Arg Ile  Ser Phe Pro Arg Leu  Val Ala Asp Arg Trp  Leu Ala Ala
    1160                1165                1170

Asn Val  Glu Leu Leu Gly Asn  Gly Leu Val Phe Ala  Ala Ala Thr
    1175                1180                1185

Cys Ala  Val Leu Ser Lys Ala  His Leu Ser Ala Gly  Leu Val Gly
    1190                1195                1200

Phe Ser  Val Ser Ala Ala Leu  Gln Val Thr Gln Thr  Leu Gln Trp
    1205                1210                1215

Val Val  Arg Asn Trp Thr Asp  Leu Glu Asn Ser Ile  Val Ser Val
    1220                1225                1230

Glu Arg  Met Gln Asp Tyr Ala  Trp Thr Pro Lys Glu  Ala Pro Trp
    1235                1240                1245

Arg Leu  Pro Thr Cys Ala Ala  Gln Pro Pro Trp Pro  Gln Gly Gly
    1250                1255                1260

Gln Ile  Glu Phe Arg Asp Phe  Gly Leu Arg Tyr Arg  Pro Glu Leu
    1265                1270                1275

Pro Leu  Ala Val Gln Gly Val  Ser Phe Lys Ile His  Ala Gly Glu
    1280                1285                1290

Lys Val  Gly Ile Val Gly Arg  Thr Gly Ala Gly Lys  Ser Ser Leu
    1295                1300                1305

Ala Ser  Gly Leu Leu Arg Leu  Gln Glu Ala Ala Glu  Gly Gly Ile
    1310                1315                1320

Trp Ile  Asp Gly Val Pro Ile  Ala His Val Gly Leu  His Thr Leu
    1325                1330                1335

Arg Ser  Arg Ile Ser Ile Ile  Pro Gln Asp Pro Ile  Leu Phe Pro
    1340                1345                1350

Gly Ser  Leu Arg Met Asn Leu  Asp Leu Leu Gln Glu  His Ser Asp
    1355                1360                1365

Glu Ala  Ile Trp Ala Ala Leu  Glu Thr Val Gln Leu  Lys Ala Leu
    1370                1375                1380

Val Ala  Ser Leu Pro Gly Gln  Leu Gln Tyr Lys Cys  Ala Asp Arg
    1385                1390                1395

Gly Glu  Asp Leu Ser Val Gly  Gln Lys Gln Leu Leu  Cys Leu Ala
    1400                1405                1410

Arg Ala  Leu Leu Arg Lys Thr  Gln Ile Leu Ile Leu  Asp Glu Ala
    1415                1420                1425

Thr Ala  Ala Val Asp Pro Gly  Thr Glu Leu Gln Met  Gln Ala Met
    1430                1435                1440

Leu Gly  Ser Trp Phe Ala Gln  Cys Thr Val Leu Leu  Ile Ala His
    1445                1450                1455

Arg Leu  Arg Ser Val Met Asp  Cys Ala Arg Val Leu  Val Met Asp
    1460                1465                1470

Lys Gly  Gln Val Ala Glu Ser  Gly Ser Pro Ala Gln  Leu Leu Ala
    1475                1480                1485

Gln Lys  Gly Leu Phe Tyr Arg  Leu Ala Gln Glu Ser  Gly Leu Val
    1490                1495                1500
```

<210> SEQ ID NO 4
<211> LENGTH: 20
<212> TYPE: DNA
<213> ORGANISM: Artificial
<220> FEATURE:
<223> OTHER INFORMATION: PCR primer for ABCC6

-continued

<400> SEQUENCE: 4

```
agccacgttc tggtgggttt                                               20


<210> SEQ ID NO 5
<211> LENGTH: 20
<212> TYPE: DNA
<213> ORGANISM: Artificial
<220> FEATURE:
<223> OTHER INFORMATION: PCR primer for ABCC6

<400> SEQUENCE: 5

ggaggcttgg gatcaccaat                                               20


<210> SEQ ID NO 6
<211> LENGTH: 20
<212> TYPE: DNA
<213> ORGANISM: Artificial
<220> FEATURE:
<223> OTHER INFORMATION: PCR primer for MRP-1

<400> SEQUENCE: 6

caactgcatc gttctgtttg                                               20


<210> SEQ ID NO 7
<211> LENGTH: 20
<212> TYPE: DNA
<213> ORGANISM: Artificial
<220> FEATURE:
<223> OTHER INFORMATION: PCR primer for MRP-1

<400> SEQUENCE: 7

atactccttg agcctctcca                                               20


<210> SEQ ID NO 8
<211> LENGTH: 4980
<212> TYPE: DNA
<213> ORGANISM: Mus musculus
<220> FEATURE:
<221> NAME/KEY: CDS
<222> LOCATION: (12)..(4508)
<223> OTHER INFORMATION: cDNA for mouse MRP6

<400> SEQUENCE: 8

ccgcgtcgac g atg aac agc ggg cgc tcc atg gcc acg cct gga gag cag      50
             Met Asn Ser Gly Arg Ser Met Ala Thr Pro Gly Glu Gln
             1               5                   10

tgc gcc ggc ctg agg gtc tgg aac cag aca gag cag gag cct gcg gcc       98
Cys Ala Gly Leu Arg Val Trp Asn Gln Thr Glu Gln Glu Pro Ala Ala
    15                  20                  25

tat cac ttg ctc agc ctg tgc ttc gtg aga gcc gcc agc agc tgg gtg      146
Tyr His Leu Leu Ser Leu Cys Phe Val Arg Ala Ala Ser Ser Trp Val
30                  35                  40                  45

ccc ccc atg tac ctc tgg gtc ctc ggc ccc atc tac ctt ctc tac atc      194
Pro Pro Met Tyr Leu Trp Val Leu Gly Pro Ile Tyr Leu Leu Tyr Ile
                50                  55                  60

cat cgc cat ggc cgg tgc tac ctc cgg atg tcc cac ctc ttc aaa acc      242
His Arg His Gly Arg Cys Tyr Leu Arg Met Ser His Leu Phe Lys Thr
            65                  70                  75

aaa atg gtg ctg ggc ttg gcc ctc atc ctt ctg tat acc ttc aac gtg      290
Lys Met Val Leu Gly Leu Ala Leu Ile Leu Leu Tyr Thr Phe Asn Val
        80                  85                  90

gcc gtg cct ctg tgg agg atc cac cag ggc gtg ccc cag gcc cca gag      338
Ala Val Pro Leu Trp Arg Ile His Gln Gly Val Pro Gln Ala Pro Glu
    95                  100                 105
```

-continued

```
ctt cta att cac cct act gtg tgg ctc acc acc atg agc ttt gcc acc      386
Leu Leu Ile His Pro Thr Val Trp Leu Thr Thr Met Ser Phe Ala Thr
110                 115                 120                 125

ttt ctg atc cac atg gag aga agg aag gga gtc cgg tca tcc ggg gtg      434
Phe Leu Ile His Met Glu Arg Arg Lys Gly Val Arg Ser Ser Gly Val
                130                 135                 140

ttg ttc ggg tac tgg ctg ctc tgc tgc atc ttg cca gga atc aac act      482
Leu Phe Gly Tyr Trp Leu Leu Cys Cys Ile Leu Pro Gly Ile Asn Thr
            145                 150                 155

gtg cag cag gcc tct gca ggg aac tta cgt cag gag ccc ctc cac cac      530
Val Gln Gln Ala Ser Ala Gly Asn Leu Arg Gln Glu Pro Leu His His
        160                 165                 170

ctg gcc acc tac ctg tgc ttg tcc ctg gtg gtg gct gag ctg gtg ctg      578
Leu Ala Thr Tyr Leu Cys Leu Ser Leu Val Val Ala Glu Leu Val Leu
    175                 180                 185

tcc tgt ctg gtg gac cag cca ccc ttc ttc tcg gaa gac tcc cag cca      626
Ser Cys Leu Val Asp Gln Pro Pro Phe Phe Ser Glu Asp Ser Gln Pro
190                 195                 200                 205

ttg aat ccg tgt cca gag gct gag gcc tcc ttt ccc tcc aag gcc atg      674
Leu Asn Pro Cys Pro Glu Ala Glu Ala Ser Phe Pro Ser Lys Ala Met
                210                 215                 220

ttc tgg tgg gcc tct gga ctg cta tgg agg ggc tac aaa aag ctg ctg      722
Phe Trp Trp Ala Ser Gly Leu Leu Trp Arg Gly Tyr Lys Lys Leu Leu
            225                 230                 235

gga cca aaa gac ctc tgg tca ctt ggg aga gaa aac tct tca gaa gaa      770
Gly Pro Lys Asp Leu Trp Ser Leu Gly Arg Glu Asn Ser Ser Glu Glu
        240                 245                 250

ctc gtt tcc cag ctg gaa aga gaa tgg agg aga agc tgc aat ggg ctg      818
Leu Val Ser Gln Leu Glu Arg Glu Trp Arg Arg Ser Cys Asn Gly Leu
    255                 260                 265

cca ggg cac aaa ggg cac agt agt gtg ggg gcc cct gag aca gag gcc      866
Pro Gly His Lys Gly His Ser Ser Val Gly Ala Pro Glu Thr Glu Ala
270                 275                 280                 285

ttc ctg cag cca gag agg agt cag agg ggc cca cta ctc agg gct atc      914
Phe Leu Gln Pro Glu Arg Ser Gln Arg Gly Pro Leu Leu Arg Ala Ile
                290                 295                 300

tgg cgc gtg ttc cgg tcc acc ttc ctg ctg ggg acc ctc agc ctg gtc      962
Trp Arg Val Phe Arg Ser Thr Phe Leu Leu Gly Thr Leu Ser Leu Val
            305                 310                 315

att agc gat gcc ttc agg ttt gct gtt ccc aag ctc ctc agt ctg ttt     1010
Ile Ser Asp Ala Phe Arg Phe Ala Val Pro Lys Leu Leu Ser Leu Phe
        320                 325                 330

ctg gag ttc atg ggt gac cgc aac tcc tcg gcg tgg aca ggc tgg ctc     1058
Leu Glu Phe Met Gly Asp Arg Asn Ser Ser Ala Trp Thr Gly Trp Leu
    335                 340                 345

cta gct gtg ctg atg ttc gcg gca gcc tgc cta cag acg ttg ttt gaa     1106
Leu Ala Val Leu Met Phe Ala Ala Ala Cys Leu Gln Thr Leu Phe Glu
350                 355                 360                 365

cag cag cac atg tac aga gcc aag gtc ctg cag atg agg ctg cga aca     1154
Gln Gln His Met Tyr Arg Ala Lys Val Leu Gln Met Arg Leu Arg Thr
                370                 375                 380

gcc atc act ggc ctg gtg tac aga aag gtc ctg gtc ctg tcc agt ggt     1202
Ala Ile Thr Gly Leu Val Tyr Arg Lys Val Leu Val Leu Ser Ser Gly
            385                 390                 395

tcc aga aag tcc agc gca gca gga gac gtg gtc aac ctg gtg tcg gtg     1250
Ser Arg Lys Ser Ser Ala Ala Gly Asp Val Val Asn Leu Val Ser Val
        400                 405                 410

gac atc cag cgg ctg gcc gag agc atc atc tac ctc aac ggg ctg tgg     1298
Asp Ile Gln Arg Leu Ala Glu Ser Ile Ile Tyr Leu Asn Gly Leu Trp
```

-continued

```
    415                 420                 425

ctg ctc ttc ctg tgg atc ttt gtg tgc ttt gtc tac ctg tgg cag ctc      1346
Leu Leu Phe Leu Trp Ile Phe Val Cys Phe Val Tyr Leu Trp Gln Leu
430                 435                 440                 445

ctt gga ccc tct gct ctc aca gcc gtt gct gtc ttc ctg agc ctc ctc      1394
Leu Gly Pro Ser Ala Leu Thr Ala Val Ala Val Phe Leu Ser Leu Leu
                450                 455                 460

cct ctg aac ttc ttc atc acc aag aag agg ggc ttc cat cag gaa gaa      1442
Pro Leu Asn Phe Phe Ile Thr Lys Lys Arg Gly Phe His Gln Glu Glu
            465                 470                 475

cag atg agg cag aag gcc tcc aga gca cgg ctc acc agc tcc atg ctc      1490
Gln Met Arg Gln Lys Ala Ser Arg Ala Arg Leu Thr Ser Ser Met Leu
        480                 485                 490

aga act gtg aga acc atc aag tcc cac ggc tgg gag cat gcc ttc ctg      1538
Arg Thr Val Arg Thr Ile Lys Ser His Gly Trp Glu His Ala Phe Leu
    495                 500                 505

gag cga ctc ctt cac atc cgg ggc cag gag ctc agc gcc ctg aag acc      1586
Glu Arg Leu Leu His Ile Arg Gly Gln Glu Leu Ser Ala Leu Lys Thr
510                 515                 520                 525

tcc acc ctc ctc ttc tct gtg tct ctc gtg tcc ttc caa gtg tct aca      1634
Ser Thr Leu Leu Phe Ser Val Ser Leu Val Ser Phe Gln Val Ser Thr
                530                 535                 540

ttt ctg gtg gcg ctg gtc gtg ttt gct gtc cac acc ctg gtg gca gag      1682
Phe Leu Val Ala Leu Val Val Phe Ala Val His Thr Leu Val Ala Glu
            545                 550                 555

gac aat gcc atg gat gca gag aag gcc ttt gtg acg ctc aca gtg ctc      1730
Asp Asn Ala Met Asp Ala Glu Lys Ala Phe Val Thr Leu Thr Val Leu
        560                 565                 570

agc atc ctt aac aaa gcc cag gcc ttc ctc ccc ttc tct gtg cac tgc      1778
Ser Ile Leu Asn Lys Ala Gln Ala Phe Leu Pro Phe Ser Val His Cys
    575                 580                 585

atc gtt cag gct cga gtg tcc ttt gac cgg ctg gct gcc ttc ctg tgc      1826
Ile Val Gln Ala Arg Val Ser Phe Asp Arg Leu Ala Ala Phe Leu Cys
590                 595                 600                 605

ctg gaa gaa gta gac ccc aat ggc atg atc gcg agt aac tcc agg cgc      1874
Leu Glu Glu Val Asp Pro Asn Gly Met Ile Ala Ser Asn Ser Arg Arg
                610                 615                 620

tcc tcg aag gat cga att tct gta cac aat ggc acc ttc gct tgg tcc      1922
Ser Ser Lys Asp Arg Ile Ser Val His Asn Gly Thr Phe Ala Trp Ser
            625                 630                 635

cag gag agc cca ccc tgc ctg cac ggg atc aac ctc acc gtg ccc cag      1970
Gln Glu Ser Pro Pro Cys Leu His Gly Ile Asn Leu Thr Val Pro Gln
        640                 645                 650

ggc tgt ctg ctg gct gtt gtg ggt cca gtg ggg gct ggg aag tcc tcc      2018
Gly Cys Leu Leu Ala Val Val Gly Pro Val Gly Ala Gly Lys Ser Ser
    655                 660                 665

ctg ctg tct gcc ctg ctt ggg gag ctg ttg aag gta gaa ggg tct gtg      2066
Leu Leu Ser Ala Leu Leu Gly Glu Leu Leu Lys Val Glu Gly Ser Val
670                 675                 680                 685

agc att gag ggt tcc gtg gct tac gtg cct cag gag gcc tgg gtc cag      2114
Ser Ile Glu Gly Ser Val Ala Tyr Val Pro Gln Glu Ala Trp Val Gln
                690                 695                 700

aat acc tct gtg gcg gag aat gtg tgc ttc agg caa gag ctg gac ctg      2162
Asn Thr Ser Val Ala Glu Asn Val Cys Phe Arg Gln Glu Leu Asp Leu
            705                 710                 715

ccc tgg ttg cag aaa gtt cta gac gcc tgt gcc ttg ggg tct gat gtg      2210
Pro Trp Leu Gln Lys Val Leu Asp Ala Cys Ala Leu Gly Ser Asp Val
        720                 725                 730

gcc agc ttc cct gca gga gtt cac acc cca ata ggg gag cag ggc atg      2258
```

-continued

```
Ala Ser Phe Pro Ala Gly Val His Thr Pro Ile Gly Glu Gln Gly Met
    735                 740                 745

aat ctt tct ggg ggc cag aag cag cgg ctg agc ttg gct cgg gct gtg      2306
Asn Leu Ser Gly Gly Gln Lys Gln Arg Leu Ser Leu Ala Arg Ala Val
750                 755                 760                 765

tac aaa aag gct gcc atc tac ttg ctg gat gac ccc ctg gca gcg ctg      2354
Tyr Lys Lys Ala Ala Ile Tyr Leu Leu Asp Asp Pro Leu Ala Ala Leu
                770                 775                 780

gat gcc cac gtc agc cag cag gtc ttc aaa cag gtc atc ggg ccc agt      2402
Asp Ala His Val Ser Gln Gln Val Phe Lys Gln Val Ile Gly Pro Ser
            785                 790                 795

gga ttg ctc cag ggt acg act cgg atc ctt gta aca cac acg ctg cac      2450
Gly Leu Leu Gln Gly Thr Thr Arg Ile Leu Val Thr His Thr Leu His
        800                 805                 810

gtc ctg ccc cag gct gac cgg atc ctg gtg ctg gcc aat ggg acc atc      2498
Val Leu Pro Gln Ala Asp Arg Ile Leu Val Leu Ala Asn Gly Thr Ile
    815                 820                 825

gca gag atg ggc tcc tac cag gac ctt ctg caa agg aac gga gcc ctg      2546
Ala Glu Met Gly Ser Tyr Gln Asp Leu Leu Gln Arg Asn Gly Ala Leu
830                 835                 840                 845

gtg ggt ctt ctg gat gga gcc aga cag cct gca gga aca cac gat gca      2594
Val Gly Leu Leu Asp Gly Ala Arg Gln Pro Ala Gly Thr His Asp Ala
                850                 855                 860

gct acc agt gac gac ctc gga ggc ttt cct gga ggt ggg agg ccc aca      2642
Ala Thr Ser Asp Asp Leu Gly Gly Phe Pro Gly Gly Gly Arg Pro Thr
            865                 870                 875

tgc aga cca gac agg ccc agg ccc acg gag gca gcc cct gtg aag ggc      2690
Cys Arg Pro Asp Arg Pro Arg Pro Thr Glu Ala Ala Pro Val Lys Gly
        880                 885                 890

agg agc aca tct gag gta cag atg gag gct tct ctg gat gac cct gag      2738
Arg Ser Thr Ser Glu Val Gln Met Glu Ala Ser Leu Asp Asp Pro Glu
    895                 900                 905

gcc aca gga ttg aca gca gaa gag gat agt gtg cga tat ggc cgg gtg      2786
Ala Thr Gly Leu Thr Ala Glu Glu Asp Ser Val Arg Tyr Gly Arg Val
910                 915                 920                 925

aag atc acc ata tac ctg agc tac ctg cgg gcg gtg ggc aca ccc ctc      2834
Lys Ile Thr Ile Tyr Leu Ser Tyr Leu Arg Ala Val Gly Thr Pro Leu
                930                 935                 940

tgt acc tac acc ctg ttc ctc ttc ctc tgc cag caa gtg gca tcc ttc      2882
Cys Thr Tyr Thr Leu Phe Leu Phe Leu Cys Gln Gln Val Ala Ser Phe
            945                 950                 955

tcc caa ggc tac tgg ctg agc ctt tgg gcc gat gac ccg gtt gtg gat      2930
Ser Gln Gly Tyr Trp Leu Ser Leu Trp Ala Asp Asp Pro Val Val Asp
        960                 965                 970

ggg cgg cag atg cat gca gcc ctg cgt ggc tgg gtc ttt ggg ctc ctt      2978
Gly Arg Gln Met His Ala Ala Leu Arg Gly Trp Val Phe Gly Leu Leu
    975                 980                 985

ggc tgt ctg caa gcc atc gga ctg ttt gcc tcc  atg gct gcg gtg ttc     3026
Gly Cys Leu Gln Ala Ile Gly Leu Phe Ala Ser  Met Ala Ala Val Phe
990                 995                 1000                1005

ctg ggt gga gcc cgg  gcc tca ggc ctc ctt  ttc cgg agt ctc ctg        3071
Leu Gly Gly Ala Arg  Ala Ser Gly Leu Leu  Phe Arg Ser Leu Leu
                1010                 1015                 1020

tgg gac gtg gct cgc  tct ccc atc ggc ttc  ttt gag cgc acg cca        3116
Trp Asp Val Ala Arg  Ser Pro Ile Gly Phe  Phe Glu Arg Thr Pro
                1025                 1030                 1035

gtc ggg aac ctg ctg  aac cgc ttt tcc aag  gag aca gac aca gtg        3161
Val Gly Asn Leu Leu  Asn Arg Phe Ser Lys  Glu Thr Asp Thr Val
                1040                 1045                 1050
```

-continued

```
gat gtg gac atc ccg  gac aag ctg agg tcc  ctt ctg acc tat gcc       3206
Asp Val Asp Ile Pro  Asp Lys Leu Arg Ser  Leu Leu Thr Tyr Ala
                1055                 1060                 1065

ttt ggg ctc ctg gag  gtc ggc ctg gca gtg  acg atg gcc acg cct       3251
Phe Gly Leu Leu Glu  Val Gly Leu Ala Val  Thr Met Ala Thr Pro
                1070                 1075                 1080

ctg gcc att gtg gcc  atc cta cct ctc atg  gtc ctc tat gct ggg       3296
Leu Ala Ile Val Ala  Ile Leu Pro Leu Met  Val Leu Tyr Ala Gly
                1085                 1090                 1095

ttt cag agc ctc tat  gtg gcc aca tct tgc  cag ctg aga cgt cta       3341
Phe Gln Ser Leu Tyr  Val Ala Thr Ser Cys  Gln Leu Arg Arg Leu
                1100                 1105                 1110

gag tca gcc cgc tac  tca tct gtg tgt tcc  cat atg gct gag acc       3386
Glu Ser Ala Arg Tyr  Ser Ser Val Cys Ser  His Met Ala Glu Thr
                1115                 1120                 1125

ttc cag gga agt ctg  gtg gtc agg gcc ttc  cgg gcc cag gcg tcc       3431
Phe Gln Gly Ser Leu  Val Val Arg Ala Phe  Arg Ala Gln Ala Ser
                1130                 1135                 1140

ttc acg gct cag cac  gat gct ctc atg gat  gag aac cag agg gtc       3476
Phe Thr Ala Gln His  Asp Ala Leu Met Asp  Glu Asn Gln Arg Val
                1145                 1150                 1155

agt ttc ccg aaa ctg  gtg gct gac agg tgg  ctg gct act aac ctg       3521
Ser Phe Pro Lys Leu  Val Ala Asp Arg Trp  Leu Ala Thr Asn Leu
                1160                 1165                 1170

gag ctt cta ggg aat  ggc ttg gta ttc gtg  gct gct aca tgt gct       3566
Glu Leu Leu Gly Asn  Gly Leu Val Phe Val  Ala Ala Thr Cys Ala
                1175                 1180                 1185

gtg ctg agc aag gct  cac cta agt gct ggc  ctc gtg ggc ttc tcg       3611
Val Leu Ser Lys Ala  His Leu Ser Ala Gly  Leu Val Gly Phe Ser
                1190                 1195                 1200

gtc tcc gct gcc ctc  cag gtg aca cag act  ctg cag tgg gtg gtc       3656
Val Ser Ala Ala Leu  Gln Val Thr Gln Thr  Leu Gln Trp Val Val
                1205                 1210                 1215

cgc agc tgg aca gat  ctg gag aac agc atg  gta gcc gtg gag cgc       3701
Arg Ser Trp Thr Asp  Leu Glu Asn Ser Met  Val Ala Val Glu Arg
                1220                 1225                 1230

gtg cag gac tac gct  cgc atc ccc aaa gag  gct ccc tgg agg ctg       3746
Val Gln Asp Tyr Ala  Arg Ile Pro Lys Glu  Ala Pro Trp Arg Leu
                1235                 1240                 1245

ccc acc tgc gca gcc  cag cct ctc tgg cct  tgt ggg gga cag att       3791
Pro Thr Cys Ala Ala  Gln Pro Leu Trp Pro  Cys Gly Gly Gln Ile
                1250                 1255                 1260

gag ttc cgg gac ttt  ggg ctc aga cac cga  cca gag ctg ccc ttg       3836
Glu Phe Arg Asp Phe  Gly Leu Arg His Arg  Pro Glu Leu Pro Leu
                1265                 1270                 1275

gct gtg cag gga gtg  tcc ctg aag atc cat  gca gga gag aag gtg       3881
Ala Val Gln Gly Val  Ser Leu Lys Ile His  Ala Gly Glu Lys Val
                1280                 1285                 1290

ggc atc gtg ggc aga  aca ggg gcc ggg aag  tcc tcc ctg gct tgg       3926
Gly Ile Val Gly Arg  Thr Gly Ala Gly Lys  Ser Ser Leu Ala Trp
                1295                 1300                 1305

ggc ctg ctg cgg ctt  cag gag gct gcc gag  ggt aat atc tgg atc       3971
Gly Leu Leu Arg Leu  Gln Glu Ala Ala Glu  Gly Asn Ile Trp Ile
                1310                 1315                 1320

gat ggg gtc cct atc  acc cat gtg ggg ctg  cac aca ctg agg tcc       4016
Asp Gly Val Pro Ile  Thr His Val Gly Leu  His Thr Leu Arg Ser
                1325                 1330                 1335

cga atc acc atc atc  cct cag gac cct gtc  ctg ttc cca ggc tct       4061
Arg Ile Thr Ile Ile  Pro Gln Asp Pro Val  Leu Phe Pro Gly Ser
                1340                 1345                 1350
```

```
ctg cgg atg aac ctg  gac ctg ctt cag gag  cac aca gat gaa ggc       4106
Leu Arg Met Asn Leu  Asp Leu Leu Gln Glu  His Thr Asp Glu Gly
                1355                 1360                 1365

atc tgg gca gcg ctg  gag aca gtg cag ctc  aag gcc ttc gtg acc       4151
Ile Trp Ala Ala Leu  Glu Thr Val Gln Leu  Lys Ala Phe Val Thr
                1370                 1375                 1380

agc ctg cct ggc cag  ctg caa tat gag tgt  gca ggc cag gga gat       4196
Ser Leu Pro Gly Gln  Leu Gln Tyr Glu Cys  Ala Gly Gln Gly Asp
                1385                 1390                 1395

gac ctg agc gtg ggt  cat aaa cag ctc ctg  tgc ctg gca cga gcc       4241
Asp Leu Ser Val Gly  His Lys Gln Leu Leu  Cys Leu Ala Arg Ala
                1400                 1405                 1410

ctt ctc cgg aaa acc  cag atc ctc atc ctg  gac gag gcg act gcc       4286
Leu Leu Arg Lys Thr  Gln Ile Leu Ile Leu  Asp Glu Ala Thr Ala
                1415                 1420                 1425

tct gtg gac cca ggg  acg gag atg cag atg  cag gcg gcc ctg gag       4331
Ser Val Asp Pro Gly  Thr Glu Met Gln Met  Gln Ala Ala Leu Glu
                1430                 1435                 1440

cgc tgg ttt aca cag  tgt acc tta ctg ctt  atc gct cac cgc ctg       4376
Arg Trp Phe Thr Gln  Cys Thr Leu Leu Leu  Ile Ala His Arg Leu
                1445                 1450                 1455

cgc tcc gtg atg gac  tgt gcc aga gtc cta  gtc atg gat gag ggg       4421
Arg Ser Val Met Asp  Cys Ala Arg Val Leu  Val Met Asp Glu Gly
                1460                 1465                 1470

cag gtg gca gaa agt  ggc aat cct gct cag  ctg ctg gcc cag aaa       4466
Gln Val Ala Glu Ser  Gly Asn Pro Ala Gln  Leu Leu Ala Gln Lys
                1475                 1480                 1485

ggc ctg ttt tac agg  cta gcc cat gag tcg  ggc ctc gct tga           4508
Gly Leu Phe Tyr Arg  Leu Ala His Glu Ser  Gly Leu Ala
                1490                 1495

atgaggattc ttaccaaccc ccgtggagcc agccatagag cctgcagtgg ctggagatgc   4568

cagagactcc aatctaaact cctctttggg agggagatgg cagagaaagt gatggagtat   4628

tgggatacca gacccagaag aacccagcac gcccaggttg gcctgagcaa ggccatgccc   4688

accccaggcc aaagagaatg gtaactctca gcccaagctg tctacttcaa ggccacgccc   4748

actccaggcc aatcagattg gatgccctgg acccaggtga tggtgtgcac atattcccta   4808

actccttatt ttgaagtcat tgtagatttc agtcacagtt ttaagaaata acacggagag   4868

aaactgtgac ccctctgccc tgtttattcc aagggtgaca ccttgtccaa ctctagagca   4928

tcacaccgac tctgaccgac tcgtctttac aactccaaaa aaaaaaaaaa aa           4980


<210> SEQ ID NO 9
<211> LENGTH: 1498
<212> TYPE: PRT
<213> ORGANISM: Mus musculus

<400> SEQUENCE: 9

Met Asn Ser Gly Arg Ser Met Ala Thr Pro Gly Glu Gln Cys Ala Gly
1               5                   10                  15

Leu Arg Val Trp Asn Gln Thr Glu Gln Glu Pro Ala Ala Tyr His Leu
            20                  25                  30

Leu Ser Leu Cys Phe Val Arg Ala Ala Ser Ser Trp Val Pro Pro Met
        35                  40                  45

Tyr Leu Trp Val Leu Gly Pro Ile Tyr Leu Leu Tyr Ile His Arg His
    50                  55                  60

Gly Arg Cys Tyr Leu Arg Met Ser His Leu Phe Lys Thr Lys Met Val
65                  70                  75                  80
```

-continued

```
Leu Gly Leu Ala Leu Ile Leu Leu Tyr Thr Phe Asn Val Ala Val Pro
                85                  90                  95

Leu Trp Arg Ile His Gln Gly Val Pro Gln Ala Pro Glu Leu Leu Ile
            100                 105                 110

His Pro Thr Val Trp Leu Thr Thr Met Ser Phe Ala Thr Phe Leu Ile
        115                 120                 125

His Met Glu Arg Arg Lys Gly Val Arg Ser Ser Gly Val Leu Phe Gly
    130                 135                 140

Tyr Trp Leu Leu Cys Cys Ile Leu Pro Gly Ile Asn Thr Val Gln Gln
145                 150                 155                 160

Ala Ser Ala Gly Asn Leu Arg Gln Glu Pro Leu His His Leu Ala Thr
                165                 170                 175

Tyr Leu Cys Leu Ser Leu Val Val Ala Glu Leu Val Leu Ser Cys Leu
            180                 185                 190

Val Asp Gln Pro Pro Phe Phe Ser Glu Asp Ser Gln Pro Leu Asn Pro
        195                 200                 205

Cys Pro Glu Ala Glu Ala Ser Phe Pro Ser Lys Ala Met Phe Trp Trp
    210                 215                 220

Ala Ser Gly Leu Leu Trp Arg Gly Tyr Lys Lys Leu Leu Gly Pro Lys
225                 230                 235                 240

Asp Leu Trp Ser Leu Gly Arg Glu Asn Ser Ser Glu Glu Leu Val Ser
                245                 250                 255

Gln Leu Glu Arg Glu Trp Arg Arg Ser Cys Asn Gly Leu Pro Gly His
            260                 265                 270

Lys Gly His Ser Ser Val Gly Ala Pro Glu Thr Glu Ala Phe Leu Gln
        275                 280                 285

Pro Glu Arg Ser Gln Arg Gly Pro Leu Leu Arg Ala Ile Trp Arg Val
    290                 295                 300

Phe Arg Ser Thr Phe Leu Leu Gly Thr Leu Ser Leu Val Ile Ser Asp
305                 310                 315                 320

Ala Phe Arg Phe Ala Val Pro Lys Leu Leu Ser Leu Phe Leu Glu Phe
                325                 330                 335

Met Gly Asp Arg Asn Ser Ser Ala Trp Thr Gly Trp Leu Leu Ala Val
            340                 345                 350

Leu Met Phe Ala Ala Ala Cys Leu Gln Thr Leu Phe Glu Gln Gln His
        355                 360                 365

Met Tyr Arg Ala Lys Val Leu Gln Met Arg Leu Arg Thr Ala Ile Thr
    370                 375                 380

Gly Leu Val Tyr Arg Lys Val Leu Val Leu Ser Ser Gly Ser Arg Lys
385                 390                 395                 400

Ser Ser Ala Ala Gly Asp Val Val Asn Leu Val Ser Val Asp Ile Gln
                405                 410                 415

Arg Leu Ala Glu Ser Ile Ile Tyr Leu Asn Gly Leu Trp Leu Leu Phe
            420                 425                 430

Leu Trp Ile Phe Val Cys Phe Val Tyr Leu Trp Gln Leu Leu Gly Pro
        435                 440                 445

Ser Ala Leu Thr Ala Val Ala Val Phe Leu Ser Leu Leu Pro Leu Asn
    450                 455                 460

Phe Phe Ile Thr Lys Lys Arg Gly Phe His Gln Glu Glu Gln Met Arg
465                 470                 475                 480

Gln Lys Ala Ser Arg Ala Arg Leu Thr Ser Ser Met Leu Arg Thr Val
                485                 490                 495
```

-continued

```
Arg Thr Ile Lys Ser His Gly Trp Glu His Ala Phe Leu Glu Arg Leu
            500                 505                 510

Leu His Ile Arg Gly Gln Glu Leu Ser Ala Leu Lys Thr Ser Thr Leu
        515                 520                 525

Leu Phe Ser Val Ser Leu Val Ser Phe Gln Val Ser Thr Phe Leu Val
    530                 535                 540

Ala Leu Val Val Phe Ala Val His Thr Leu Val Ala Glu Asp Asn Ala
545                 550                 555                 560

Met Asp Ala Glu Lys Ala Phe Val Thr Leu Thr Val Leu Ser Ile Leu
                565                 570                 575

Asn Lys Ala Gln Ala Phe Leu Pro Phe Ser Val His Cys Ile Val Gln
            580                 585                 590

Ala Arg Val Ser Phe Asp Arg Leu Ala Ala Phe Leu Cys Leu Glu Glu
        595                 600                 605

Val Asp Pro Asn Gly Met Ile Ala Ser Asn Ser Arg Arg Ser Ser Lys
    610                 615                 620

Asp Arg Ile Ser Val His Asn Gly Thr Phe Ala Trp Ser Gln Glu Ser
625                 630                 635                 640

Pro Pro Cys Leu His Gly Ile Asn Leu Thr Val Pro Gln Gly Cys Leu
                645                 650                 655

Leu Ala Val Val Gly Pro Val Gly Ala Gly Lys Ser Ser Leu Leu Ser
            660                 665                 670

Ala Leu Leu Gly Glu Leu Leu Lys Val Glu Gly Ser Val Ser Ile Glu
        675                 680                 685

Gly Ser Val Ala Tyr Val Pro Gln Glu Ala Trp Val Gln Asn Thr Ser
    690                 695                 700

Val Ala Glu Asn Val Cys Phe Arg Gln Glu Leu Asp Leu Pro Trp Leu
705                 710                 715                 720

Gln Lys Val Leu Asp Ala Cys Ala Leu Gly Ser Asp Val Ala Ser Phe
                725                 730                 735

Pro Ala Gly Val His Thr Pro Ile Gly Glu Gln Gly Met Asn Leu Ser
            740                 745                 750

Gly Gly Gln Lys Gln Arg Leu Ser Leu Ala Arg Ala Val Tyr Lys Lys
        755                 760                 765

Ala Ala Ile Tyr Leu Leu Asp Asp Pro Leu Ala Ala Leu Asp Ala His
    770                 775                 780

Val Ser Gln Gln Val Phe Lys Gln Val Ile Gly Pro Ser Gly Leu Leu
785                 790                 795                 800

Gln Gly Thr Thr Arg Ile Leu Val Thr His Thr Leu His Val Leu Pro
                805                 810                 815

Gln Ala Asp Arg Ile Leu Val Leu Ala Asn Gly Thr Ile Ala Glu Met
            820                 825                 830

Gly Ser Tyr Gln Asp Leu Leu Gln Arg Asn Gly Ala Leu Val Gly Leu
        835                 840                 845

Leu Asp Gly Ala Arg Gln Pro Ala Gly Thr His Asp Ala Ala Thr Ser
    850                 855                 860

Asp Asp Leu Gly Gly Phe Pro Gly Gly Gly Arg Pro Thr Cys Arg Pro
865                 870                 875                 880

Asp Arg Pro Arg Pro Thr Glu Ala Ala Pro Val Lys Gly Arg Ser Thr
                885                 890                 895

Ser Glu Val Gln Met Glu Ala Ser Leu Asp Asp Pro Glu Ala Thr Gly
            900                 905                 910

Leu Thr Ala Glu Glu Asp Ser Val Arg Tyr Gly Arg Val Lys Ile Thr
```

-continued

```
      915                 920                 925

Ile Tyr Leu Ser Tyr Leu Arg Ala Val Gly Thr Pro Leu Cys Thr Tyr
    930                 935                 940

Thr Leu Phe Leu Phe Leu Cys Gln Gln Val Ala Ser Phe Ser Gln Gly
945                 950                 955                 960

Tyr Trp Leu Ser Leu Trp Ala Asp Asp Pro Val Val Asp Gly Arg Gln
                965                 970                 975

Met His Ala Ala Leu Arg Gly Trp Val Phe Gly Leu Leu Gly Cys Leu
            980                 985                 990

Gln Ala Ile Gly Leu Phe Ala Ser  Met Ala Ala Val Phe  Leu Gly Gly
      995                 1000                 1005

Ala Arg  Ala Ser Gly Leu Leu  Phe Arg Ser Leu Leu  Trp Asp Val
    1010                 1015                 1020

Ala Arg  Ser Pro Ile Gly Phe  Phe Glu Arg Thr Pro  Val Gly Asn
    1025                 1030                 1035

Leu Leu  Asn Arg Phe Ser Lys  Glu Thr Asp Thr Val  Asp Val Asp
    1040                 1045                 1050

Ile Pro  Asp Lys Leu Arg Ser  Leu Leu Thr Tyr Ala  Phe Gly Leu
    1055                 1060                 1065

Leu Glu  Val Gly Leu Ala Val  Thr Met Ala Thr Pro  Leu Ala Ile
    1070                 1075                 1080

Val Ala  Ile Leu Pro Leu Met  Val Leu Tyr Ala Gly  Phe Gln Ser
    1085                 1090                 1095

Leu Tyr  Val Ala Thr Ser Cys  Gln Leu Arg Arg Leu  Glu Ser Ala
    1100                 1105                 1110

Arg Tyr  Ser Ser Val Cys Ser  His Met Ala Glu Thr  Phe Gln Gly
    1115                 1120                 1125

Ser Leu  Val Val Arg Ala Phe  Arg Ala Gln Ala Ser  Phe Thr Ala
    1130                 1135                 1140

Gln His  Asp Ala Leu Met Asp  Glu Asn Gln Arg Val  Ser Phe Pro
    1145                 1150                 1155

Lys Leu  Val Ala Asp Arg Trp  Leu Ala Thr Asn Leu  Glu Leu Leu
    1160                 1165                 1170

Gly Asn  Gly Leu Val Phe Val  Ala Ala Thr Cys Ala  Val Leu Ser
    1175                 1180                 1185

Lys Ala  His Leu Ser Ala Gly  Leu Val Gly Phe Ser  Val Ser Ala
    1190                 1195                 1200

Ala Leu  Gln Val Thr Gln Thr  Leu Gln Trp Val Val  Arg Ser Trp
    1205                 1210                 1215

Thr Asp  Leu Glu Asn Ser Met  Val Ala Val Glu Arg  Val Gln Asp
    1220                 1225                 1230

Tyr Ala  Arg Ile Pro Lys Glu  Ala Pro Trp Arg Leu  Pro Thr Cys
    1235                 1240                 1245

Ala Ala  Gln Pro Leu Trp Pro  Cys Gly Gly Gln Ile  Glu Phe Arg
    1250                 1255                 1260

Asp Phe  Gly Leu Arg His Arg  Pro Glu Leu Pro Leu  Ala Val Gln
    1265                 1270                 1275

Gly Val  Ser Leu Lys Ile His  Ala Gly Glu Lys Val  Gly Ile Val
    1280                 1285                 1290

Gly Arg  Thr Gly Ala Gly Lys  Ser Ser Leu Ala Trp  Gly Leu Leu
    1295                 1300                 1305

Arg Leu  Gln Glu Ala Ala Glu  Gly Asn Ile Trp Ile  Asp Gly Val
    1310                 1315                 1320
```

-continued

```
Pro Ile  Thr His Val Gly Leu  His Thr Leu Arg Ser  Arg Ile Thr
    1325                 1330                 1335

Ile Ile  Pro Gln Asp Pro Val  Leu Phe Pro Gly Ser  Leu Arg Met
    1340                 1345                 1350

Asn Leu  Asp Leu Leu Gln Glu  His Thr Asp Glu Gly  Ile Trp Ala
    1355                 1360                 1365

Ala Leu  Glu Thr Val Gln Leu  Lys Ala Phe Val Thr  Ser Leu Pro
    1370                 1375                 1380

Gly Gln  Leu Gln Tyr Glu Cys  Ala Gly Gln Gly Asp  Asp Leu Ser
    1385                 1390                 1395

Val Gly  His Lys Gln Leu Leu  Cys Leu Ala Arg Ala  Leu Leu Arg
    1400                 1405                 1410

Lys Thr  Gln Ile Leu Ile Leu  Asp Glu Ala Thr Ala  Ser Val Asp
    1415                 1420                 1425

Pro Gly  Thr Glu Met Gln Met  Gln Ala Ala Leu Glu  Arg Trp Phe
    1430                 1435                 1440

Thr Gln  Cys Thr Leu Leu Leu  Ile Ala His Arg Leu  Arg Ser Val
    1445                 1450                 1455

Met Asp  Cys Ala Arg Val Leu  Val Met Asp Glu Gly  Gln Val Ala
    1460                 1465                 1470

Glu Ser  Gly Asn Pro Ala Gln  Leu Leu Ala Gln Lys  Gly Leu Phe
    1475                 1480                 1485

Tyr Arg  Leu Ala His Glu Ser  Gly Leu Ala
    1490                 1495

<210> SEQ ID NO 10
<211> LENGTH: 20
<212> TYPE: DNA
<213> ORGANISM: Artificial
<220> FEATURE:
<223> OTHER INFORMATION: primer corresponding to a G to A mutation in
      exon 24 of the ABCC6 gen

<400> SEQUENCE: 10

cagtggtcca ggcattccga                                                20


<210> SEQ ID NO 11
<211> LENGTH: 20
<212> TYPE: DNA
<213> ORGANISM: Artificial
<220> FEATURE:
<223> OTHER INFORMATION: primer corresponding to a C to T mutation in
      exon 24 of the ABCC6 gen

<400> SEQUENCE: 11

cagtggtccg ggcattctga                                                20


<210> SEQ ID NO 12
<211> LENGTH: 26
<212> TYPE: DNA
<213> ORGANISM: Artificial
<220> FEATURE:
<223> OTHER INFORMATION: primer corresponding to a G to C mutation in
      exon 24 of the ABCC6 gen

<400> SEQUENCE: 12

gacccttgga gtcagccagc tactcg                                         26


<210> SEQ ID NO 13
<211> LENGTH: 26
```

-continued

<212> TYPE: DNA
<213> ORGANISM: Artificial
<220> FEATURE:
<223> OTHER INFORMATION: primer corresponding to a C to G mutation in exon 24 of the ABCC6 gen

<400> SEQUENCE: 13
gacgcttgga gtcagccagc tactgg 26

<210> SEQ ID NO 14
<211> LENGTH: 26
<212> TYPE: DNA
<213> ORGANISM: Artificial
<220> FEATURE:
<223> OTHER INFORMATION: primer corresponding to a C to T mutation in exon 26 of the ABCC gen

<400> SEQUENCE: 14
ggatgtagga ctatgcctgg acgccc 26

<210> SEQ ID NO 15
<211> LENGTH: 26
<212> TYPE: DNA
<213> ORGANISM: Artificial
<220> FEATURE:
<223> OTHER INFORMATION: primer corresponding to a G to C mutation in exon 26 of the ABCC6 gen

<400> SEQUENCE: 15
ggatgcagga ctatgcctgc acgccc 26

<210> SEQ ID NO 16
<211> LENGTH: 20
<212> TYPE: DNA
<213> ORGANISM: Artificial
<220> FEATURE:
<223> OTHER INFORMATION: primer corresponding to a C to A mutation in exon 27 of the ABCC6 gen

<400> SEQUENCE: 16
tgcagctaag ccccctggc 20

<210> SEQ ID NO 17
<211> LENGTH: 19
<212> TYPE: DNA
<213> ORGANISM: Artificial
<220> FEATURE:
<223> OTHER INFORMATION: primer corresponding to a deletion of a T in exon 27 of the ABCC6 gen

<400> SEQUENCE: 17
tgcagctcag ccccccggc 19

<210> SEQ ID NO 18
<211> LENGTH: 20
<212> TYPE: DNA
<213> ORGANISM: Artificial
<220> FEATURE:
<223> OTHER INFORMATION: primer corresponding to a G to A mutation in exon 27 of the ABCC6 gen

<400> SEQUENCE: 18
gctccaagct ccctggaggc 20

<210> SEQ ID NO 19
<211> LENGTH: 30
<212> TYPE: DNA

```
<213> ORGANISM: Artificial
<220> FEATURE:
<223> OTHER INFORMATION: primer corresponding to a C to T mutation in
      exon 28 of the ABCC6 gen

<400> SEQUENCE: 19

ctgtggctcc aggaggcagc tgagggtggg                                    30


<210> SEQ ID NO 20
<211> LENGTH: 30
<212> TYPE: DNA
<213> ORGANISM: Artificial
<220> FEATURE:
<223> OTHER INFORMATION: primer corresponding to a G to A mutation in
      exon 28 of the ABCC6 gen

<400> SEQUENCE: 20

ctgcagctcc aggaggcagc tgagggtggg                                    30


<210> SEQ ID NO 21
<211> LENGTH: 30
<212> TYPE: DNA
<213> ORGANISM: Artificial
<220> FEATURE:
<223> OTHER INFORMATION: primer corresponding to a G to A mutation in
      exon 28 of the ABCC6 gen

<400> SEQUENCE: 21

ctgcggctcc aggaggcagc tgagagtggg                                    30


<210> SEQ ID NO 22
<211> LENGTH: 25
<212> TYPE: DNA
<213> ORGANISM: Artificial
<220> FEATURE:
<223> OTHER INFORMATION: primer corresponding to a G to T mutation in
      exon 28 of the ABCC6 gen

<400> SEQUENCE: 22

gtgggcatct ttggcaggac cgggg                                         25


<210> SEQ ID NO 23
<211> LENGTH: 25
<212> TYPE: DNA
<213> ORGANISM: Artificial
<220> FEATURE:
<223> OTHER INFORMATION: primer corresponding to a C to T mutation in
      exon 28 of the ABCC6 gen

<400> SEQUENCE: 23

gtgggcatcg ttggcaggac tgggg                                         25


<210> SEQ ID NO 24
<211> LENGTH: 25
<212> TYPE: DNA
<213> ORGANISM: Artificial
<220> FEATURE:
<223> OTHER INFORMATION: primer corresponding to a G to A mutation in
      exon 28 of the ABCC6 gen

<400> SEQUENCE: 24

gtgggcatcg ttggcaggac caggg                                         25


<210> SEQ ID NO 25
<211> LENGTH: 25
<212> TYPE: DNA
<213> ORGANISM: Artificial
```

-continued

```
<220> FEATURE:
<223> OTHER INFORMATION: primer corresponding to a G to C mutation in
      exon 28 of the ABCC6 gen

<400> SEQUENCE: 25

gtgggcatcg ttggcaggac cgggc                                            25


<210> SEQ ID NO 26
<211> LENGTH: 21
<212> TYPE: DNA
<213> ORGANISM: Homo sapiens
<220> FEATURE:
<221> NAME/KEY: CDS
<222> LOCATION: (1)..(12)
<223> OTHER INFORMATION: Mutation in Exon 24 of human MRP6 gene

<400> SEQUENCE: 26

cgg gca ttc tga acccaggcc                                              21
Arg Ala Phe
1


<210> SEQ ID NO 27
<211> LENGTH: 18
<212> TYPE: DNA
<213> ORGANISM: Homo sapiens
<220> FEATURE:
<221> NAME/KEY: misc_feature
<223> OTHER INFORMATION: mutation in Intron 21 of human MRP6 gene

<400> SEQUENCE: 27

tacggcaggt taaccacc                                                    18
```